(12) United States Patent
Hermiston et al.

(10) Patent No.: US 8,216,819 B2
(45) Date of Patent: Jul. 10, 2012

(54) GENERATION OF ONCOLYTIC ADENOVIRUSES AND USES THEREOF

(75) Inventors: Terry Hermiston, Corte Madera, CA (US); Irene Kuhn, Richmond, CA (US)

(73) Assignee: PsiOxus Therapeutics Limited, London (GB)

( * ) Notice: Subject to any disclaimer, the term of this patent is extended or adjusted under 35 U.S.C. 154(b) by 221 days.

(21) Appl. No.: 12/520,538

(22) PCT Filed: Dec. 20, 2007

(86) PCT No.: PCT/US2007/088415
§ 371 (c)(1),
(2), (4) Date: Nov. 10, 2009

(87) PCT Pub. No.: WO2008/080003
PCT Pub. Date: Jul. 3, 2008

(65) Prior Publication Data
US 2010/0136658 A1 Jun. 3, 2010

Related U.S. Application Data

(60) Provisional application No. 60/876,627, filed on Dec. 22, 2006.

(51) Int. Cl.
*C12N 7/00* (2006.01)
*A61K 48/00* (2006.01)
(52) U.S. Cl. .................. 435/235.1; 424/93.3; 514/44
(58) Field of Classification Search .............. None
See application file for complete search history.

(56) References Cited

U.S. PATENT DOCUMENTS

| | | | |
|---|---|---|---|
| 7,510,868 B2 * | 3/2009 | Harden et al. | 435/320.1 |
| 2004/0136958 A1 * | 7/2004 | Wadell et al. | 424/93.2 |
| 2005/0265973 A1 * | 12/2005 | Harden et al. | 424/93.2 |
| 2006/0121509 A1 * | 6/2006 | Hermiston et al. | 435/6 |
| 2009/0208924 A1 * | 8/2009 | Hermiston et al. | 435/5 |
| 2009/0227000 A1 * | 9/2009 | Harden et al. | 435/239 |
| 2011/0217693 A1 * | 9/2011 | Hermiston et al. | 435/5 |

FOREIGN PATENT DOCUMENTS
WO    WO 02/053759    *    7/2002

OTHER PUBLICATIONS

Christain Meinschad and Ernst-L. Winnacker, Journal of gen. Virol. 1980, vol. 48, pp. 219-224.*
Kuhn et al., "ColoAd1, a Chimeric Ad11p/Ad3 Oncolytic Virus for the Treatment of Colon Cancer," *Mol. Therapy 11*, Suppl. 1, p. S124, abstract No. 319, May 1, 2005.
Yan et al., "Developing Novel Oncolytic Adenoviruses through Bioselection," *J. irol.* 77, 2640-50, Feb. 2003.
Kleinman & Martin, "Matrigel: Basement membrane matrix with biological activity," *Seminars in Cancer Biology 15*, 378-86, Oct. 1, 2005.
Sood et al., "Functional role of matrix metalloproteinases in ovarian tumor cell plasticity," *Am. J. Obstetrics Gynecol. 196*, 899-909, 2004.
Sirena et al., "The nucleotide sequence and a first generation gene transfer vector of species B human adenovirus serotype 4," *Virol. 343*, 283-98, 2005.
EMBL Dabatase Accession No. DQ086466, pp. 1-19, Nov. 23, 2005.
Kuhn et al., "Directed Evolution Generates a Novel Oncolytic Virus for the Treatment of Colon Cancer," *PloS One 3*, 1-11, Jun. 2008.
Hermiston, "A demand for next-generation oncolytic adenoviruses," *Curr. Op. Mol. Therapeutics 8*, 322-30, Aug. 2006.
Hermison & Kuhn, "Armed therapeutic viruses: Strategies and challenges to arming oncolytic viruses with therapeutic genes," *Cancer Gene Therapy 9*, 1022-35, Dec. 1, 2002.
Thorne et al., "Oncolytic Virotherapy: Approaches to Tumor Targeting and Enhancing Antitumor Effects," *Sem. Oncol. 32*, 537-48, Dec. 1, 2005.
International Search Report for PCT/US2007/088415 mailed Nov. 10, 2008, pp. 1-5.

* cited by examiner

*Primary Examiner* — Bao Li
(74) *Attorney, Agent, or Firm* — Banner & Witcoff, Ltd.

(57) ABSTRACT

The present invention relates to a method for the production of onolytic adenoviruses having increased potency and their therapeutic applications for cancer. Recombinant adenoviruses and methods to produce them are provided.

12 Claims, 10 Drawing Sheets

GENERATION OF ONCOLYTIC ADENOVIRUSES AND USES THEREOF

This application is a national phase application of PCT/US2007/088415 filed on Dec. 20, 2007 and published in English as WO 2008/080003 on Jul. 3, 2008. PCT/US2007/088415 claims priority to Ser. No. 60/876,627 filed on Dec. 12, 2006. Each of these applications is incorporated herein by reference in its entirety.

This application incorporates by reference the contents of a 172 KB text file created on Jun. 21, 2009 and named "BSP53600_sequence_listing.txt," which is the sequence listing for this application.

FIELD OF THE INVENTION

The invention described herein relates to a method for generation of oncolytic adenoviruses having an increased potency/increased therapeutic index for use in the treatment of solid tumors.

BACKGROUND OF THE INVENTION

Successful selection of clinically effective oncolytic agents depends on the use of cells or tissues that accurately model target tumors, white being routinely reproducible in the laboratory. Recent work has provided evidence that three dimensional associations of extracellular matrix nanofibrils and the cellular architecture they induce are critical to development of in vitro systems that sufficiently mimic the physiological patterns of cell adhesion, cytoskeletal organization, signal transduction and gene expression, morphogenesis and differentiation in cultures of both normal and transformed cells. A number of analytical methods, including Gene Expression Profiling (GEP), proteomics and analyses of cellular function have demonstrated that 3D cultures are generally better tumor models than are monolayer cultures (Birgersdotter et al. (2005) *Semin Cancer Bio.* 15:405-412; Nelson and Bissell (2005) *Semin Cancer Biol* 15:342-352).

SUMMARY OF THE INVENTION

The present invention provides a method for the isolation of oncolytic adenoviruses useful for viral-based therapy of solid or haemotologic tumors, wherein the isolated adenoviruses display an enhanced potency as compared with a reference virus or viruses.

In one embodiment, the method comprises the steps of
(a) pooling a group of adenoviruses, wherein the adenoviruses are selected from the group consisting of the adenoviral serotypes B, C, D, E and F;
(b) passaging the pooled adenoviral mixture from step (a) on an actively growing culture of tumor cells;
(c) harvesting the supernatant from step (b);
(d) infecting a quiescent culture of tumor cells with the supernatant harvested in step (c);
(e) harvesting the cell culture supernatant from step (d) prior to any sign of CPE;
(f) infecting a quiescent culture of tumor cells with the supernatant harvested in step (e);
(g) harvesting the cell culture supernatant from step (f) prior to any sign of CPE; and
(h) isolating a virus from the supernatant of step (g) by plaque purification,
wherein the tumor cells in steps (b), (d) and (f) are all grown on, or in, an extracellular matrix.

In a preferred embodiment, the extracellular matrix is the reconstituted basement membrane known as MATRIGEL™.

In another embodiment of the invention, the pooled adenoviral mixture further comprises ColoAd1 (SEQ ID NO:3).

In another embodiment of the invention, a portion of the pool of step (a) is mutagenized prior to passaging.

In another embodiment of the invention, the passaging of step (b) is performed twice before the first harvesting of supernatant.

The present invention provides for the isolation of oncolytic adenoviruses that are specifically targeted to tumor cells derived from colon, ovarian, lung, prostate, breast or pancreas.

In one embodiment of the invention, oncolytic adenoviruses isolated by this method target ovarian tumor cells. Two isolated oncolytic adenoviruses of the invention that target ovarian tumor cells are OvAd1 (SEQ ID NO:1) and OvAd2 (SEQ ID NO:2).

In another embodiment of the invention, oncolytic adenoviruses isolated by this method target cancer progenitor cells. One isolated oncolytic adenovirus of the invention that targets ovarian cancer progenitor cells, otherwise known as ovarian cancer stem cells, is OvAd1 (SEQ ID NO:1).

The present invention further encompasses conservatively modified variants of the oncolytic adenoviruses of the invention, where said variant shows equal or greater potency, when compared with the oncolytic adenovirus of which it is a variant.

In another embodiment of the invention, oncolytic adenoviruses of the invention have been modified to produce adenoviral vectors which are replication deficient. In a preferred embodiment, an oncolytic adenovirus of the invention has been rendered replication deficient through deletion of one or more regions of the adenoviral genome, or parts thereof, which encode proteins involved in adenoviral replication, e.g. the E1, E2 or E4 regions. Particularly preferred is deletion of the E1 or E2 regions.

In another embodiment of the invention, the oncolytic adenoviruses of the invention are modified to increase their potency by reducing the size of the adenoviral genome. A preferred modification is deletion of the E3 region or parts thereof. Such a modification can be made either on the original adenovirus of the invention or on a replication deficient derivative thereof.

In another embodiment, the oncolytic adenoviruses of the invention are modified to increase tumor specificity. A preferred modification is production of an adenovirus with a "delta 24" deletion.

The present invention further provides methods for use of the oncolytic adenoviruses of the invention for therapeutic purposes. In one embodiment, the oncolytic adenoviruses of the invention can be used to inhibit the growth of tumor cells, in vitro or in vivo, by infecting the tumor cells with the oncolytic adenovirus.

In a preferred embodiment, the OvAd1 (SEQ ID NO:1) or OvAd2 (SEQ ID NO:2) adenoviruses are useful for inhibiting the growth of ovarian tumor cells (i.e. for the treatment of ovarian cancer in a patient). In a particularly preferred embodiment, the OvAd1 (SEQ ID NO:1) oncolytic adenovirus is useful for inhibiting the growth of ovarian tumor cells, particularly chemotherapy-resistant ovarian tumor cells.

In another embodiment, an oncolytic adenovirus of the invention further comprises a heterologous gene whose expression serves to attenuate adenoviral replication, such that any therapeutic dose of the virus can be eliminated in vivo when desired. In a preferred embodiment, expression of this infection-attenuating gene can be regulated, for example through use of the "tet-on" system of gene expression regulation. In another preferred embodiment, the gene is thymidine kinase, the expression of which leads to the death of infected cells upon administration of gancyclovir, leading to attenuation of viral infection.

In another embodiment, an oncolytic adenovirus of the invention further comprises a heterologous gene, wherein the heterologous gene is expressed within a cell infected with the adenovirus and encodes a therapeutic protein or factor. In a preferred embodiment, the therapeutic protein is selected from the group consisting of cytokines and chemokines, antibodies, known inducers of cell death, pro-drug converting enzymes and immunoregulatory proteins and peptides. Therapeutic factors can be, but are not limited to, small RNAs (e.g. shRNA, miRNA) and aptamers.

BRIEF DESCRIPTION OF THE FIGURES

FIG. 2. Therapeutic Index of bioselected pools.

FIG. 6. In vivo efficacy of OvAd1 and OvAd2 in an intraperitoneal (IP) model.

DETAILED DESCRIPTION OF THE INVENTION

Figure 1:
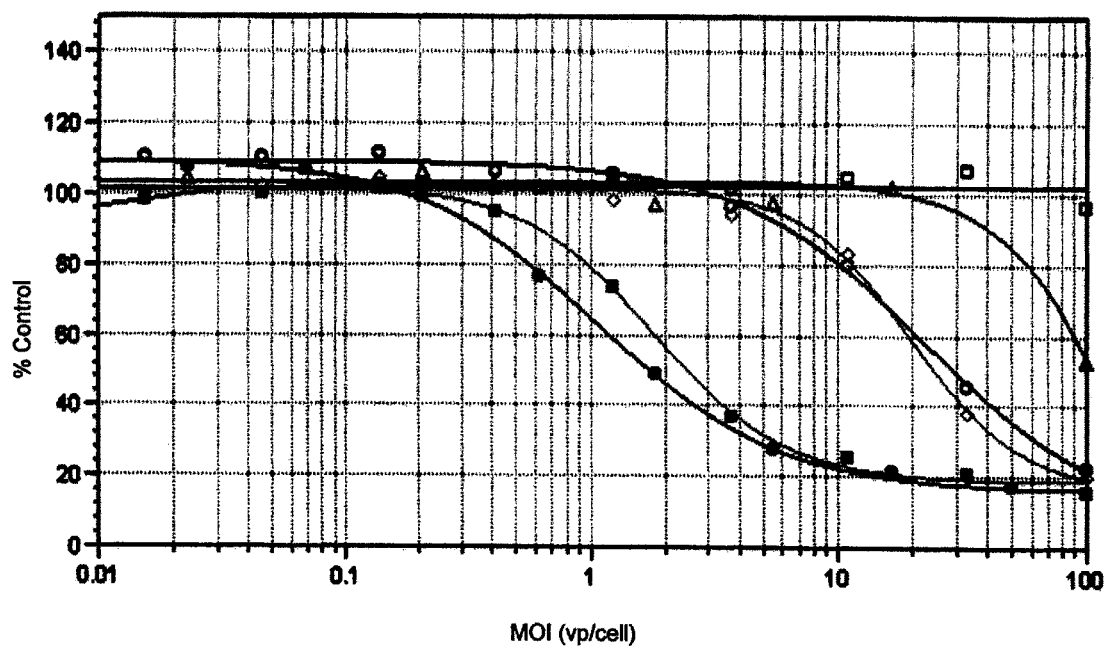
FIG. 1. Potency of bioselected pools. SM10 (-■-) and SP10 (-●-) viral pools, bioselected on MATRIGEL™ and monolayers, respectively, both show an enhanced potency on SKOV3 cells compared to the potencies of viruses in the starting pool: Ad3 (-○-); Ad5 (-□-); Ad11p (-Δ-); and Ad35 (-◇-). MTS assays were read at 7 days post infection.

All publications, including patents and patent applications, mentioned in this specification are herein incorporated by reference to the same extent as if each individual publication was specifically and individually indicated to be incorporated by reference in its entirety.

DEFINITIONS

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

As used herein, the term "adenovirus", "serotype" or "adenoviral serotype" refers to any of the 51 human adenoviral serotypes currently known, or isolated in the future. See, for example, Strauss, "Adenovirus infections in humans," in The Adenoviruses, Ginsberg, ed., Plenum Press, New York, N.Y., pp. 451-596 (1984). These serotypes are classified in the subgroups A-F (see, Shenk, "Adenoviridae: The Viruses and Their Replication," in Fields Virology, Vol. 2, Fourth Edition, Knipe, ea., Lippincott Williams & Wilkins, pp. 2265-2267 (2001), as shown in Table 1.

TABLE 1

| SubGroup | Adenoviral Serotype |
| --- | --- |
| A | 12, 18, 31 |
| B | 3, 7, 11, 14, 16, 21, 34, 35, 51 |
| C | 1, 2, 5, 6 |
| D | 8-10, 13, 15, 17, 19, 20, 22-30, 32, 33, 36-39, 42-49, 50 |
| E | 4 |
| F | 40, 41 |

As used herein, "chimeric adenovirus" refers to an adenovirus whose nucleic acid sequence is comprised of the nucleic acid sequences of at least two of the adenoviral genomes included within the initial adenoviral pool on which selection is performed.

As used herein, the term "homologous recombination" refers to two nucleic acid molecules, each having homologous sequences, where the two nucleic acid molecules cross over or undergo recombination in the region of homology.

As used herein, the term "potency" refers to the lytic potential of a virus and represents its ability to replicate, lyse, and spread. For the purposes of the instant invention, potency is the $IC_{50}$ of any given adenovirus on a given cell line.

As used herein, the term "oncolytic virus" refers to a virus that preferentially kills cancer cells as compared with normal cells.

As used herein, the term "therapeutic index" or "therapeutic window" refers to a number indicating the oncolytic selectivity of a given adenovirus and is determined by dividing the potency of an adenovirus in a normal (i.e. non-cancerous) cell line by the potency of the adenovirus in a chosen cancer cell line.

As used herein, the term "modified" refers to a molecule with a nucleotide or amino acid sequence differing from a naturally-occurring, e.g. a wild-type nucleotide or amino acid sequence or from the nucleotide sequence or amino acid sequence of an adenovirus generated by the methods of the invention. A modified molecule can retain the function or activity of a wild-type molecule, i.e. a modified adenovirus may retain its oncolytic activity. Modifications include mutations to nucleic acids, encompassing deletions, insertions and substitutions, as described below. Polynucleotides and polypeptides having such mutations can be isolated or generated using methods well known in the art.

As used herein, "mutation" with reference to a polynucleotide or polypeptide, refers to a naturally-occurring, synthetic, recombinant, or chemical change or difference to the primary, secondary, or tertiary structure of a polynucleotide or polypeptide, as compared to a reference polynucleotide or polypeptide, respectively (e.g., as compared to a wild-type polynucleotide or polypeptide).

As used herein, "deletion" is defined as a change in either polynucleotide or amino acid sequences in which one or more nucleotides or amino acid residues, respectively, are absent.

As used herein, "insertion" or "addition" is that change in a polynudeotide or amino acid sequence which has resulted in the addition of one or more nucleotides or amino acid residues, respectively, as compared to the naturally occurring polynucleotide or amino acid sequence.

As used herein, "substitution" results from the replacement of one or more nucleotides or amino acids by different nucleotides or amino acids, respectively.

As used herein, the term "adenoviral derivative" refers to an adenovirus of the invention that has been modified such that an addition, deletion or substitution has been made to or in the viral genome, such that the resulting adenoviral derivative exhibits a potency and/or therapeutic index equal to or greater than that of the parent adenovirus, or in some other way is more therapeutically useful (i.e. less immunogenic, improved clearance profile). For example, a derivative of an adenovirus of the invention may have a deletion in one of the early genes of the viral genome, including, but not limited to, the E1A or E2B region of the viral genome.

A used herein, "conservatively modified variants" applies to modifications in both amino acid and nucleic acid sequences of the adenoviruses of the invention. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Nonconservative substitutions include, but are not limited to aspartic acid (D) being replaced with glycine (G); asparagine (N) being replaced with lysine (K); or alanine (A) being replaced with arginine (R). See, e.g., Creighton, *Proteins* (1984).

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, *Proteins-Structure and Molecular Properties,* 2nd Ed., W.H. Freeman and Company, New York, 1993. Many detailed reviews are available on this subject, such as, for example, those provided by Wold, F., in *Post-translational Covalent Modification of Proteins,* B. C. Johnson, Ed., Academic Press, New York, pp 1-12, 1983;

Seifter et al., *Meth. Enzymol.* 182: 626-646, 1990 and Rattan et al., *Protein Synthesis: Posttranslational Modifications and Aging*, Ann. N.Y. Acad. Sci. 663: 48-62, 1992.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translational natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

As used herein, the following terms are used to describe the sequence relationships between two or more polynucleotide or amino acid sequences: "reference sequence", "comparison window", "sequence identity", "percentage of sequence identity", "substantial identity", "similarity", and "homologous". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted, for example, by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wisc.), VectorNTI from Informatix, Geneworks, or MacVector software packages), or by inspection, and the best alignment (i.e., resulting in the highest percentage of homology over the comparison window) generated by the various methods is selected.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. The term "similarity", when used to describe a polypeptide, is determined by comparing the amino acid sequence and the conserved amino acid substitutes of one polypeptide to the sequence of a second polypeptide. The term "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

As used herein, "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

As used herein, "polymerase chain reaction" or "PCR" refers to a procedure wherein specific pieces of DNA are amplified as described in U.S. Pat. No. 4,683,195. Generally, sequence information from the ends of the polypeptide fragment of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, plasmid sequences, etc. (See generally Mullis et al., Cold Spring Harbor Symp. Quant. Biol., 51: 263, 1987; Erlich, ed., PCR Technology, Stockton Press, NY, 1989).

As used herein, "stringency" typically occurs in a range from about $T_m$ (melting temperature)-5° C. (5° below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. As herein used, the term "stringent conditions" means hybridization will occur only if there is at least 95% and preferably at least 97% identity between the sequences.

As used herein, "hybridization" as used herein, shall include "any process by which a polynucleotide strand joins with a complementary strand through base pairing" (Coombs, J., Dictionary of Biotechnology, Stockton Press, New York, N.Y., 1994).

Adenoviruses of the Invention

The present invention provides a novel method that takes advantage of the biodiversity of adenoviral serotypes for the isolation of oncolytic adenoviruses that demonstrate an enhanced potency and/or increased selectivity toward tumors cells derived from tumor types including, but not limited to, colon, ovary, lung, prostate, breast and pancreas.

Isolation of Oncolytic Adenoviruses

The oncolytic adenoviruses of the invention are produced by directed evolution, a method that uniquely combines mutagenesis, serotype biodiversity, and stringent selection conditions to isolate an adenovirus with desired properties, such as enhanced potency or cell type specificity. Directed evolution for adenoviruses targeting particular tissues can be performed using tumor cells derived from the tissue of choice. Preferred tumor cell lines useful in the directed evolution process include, but are not limited to, those derived from breast, colon, pancreas, lung, prostate and ovary. Examples of solid tumor cell lines useful for the "directed evolution" passaging of the adenoviral mixture include, but are not limited to, MDA231, HT29 and PC-3 cells (for targeting tumors derived from breast, colon or pancreas, respectively). Particularly preferred for directed evolution of adenoviruses showing an enhanced potency in ovarian tissues include, but are not limited to, the tumor cell lines SKOV3, OVCAR3 and CaOV3. In a preferred embodiment, SKOV3 tumor cells are used for selection of oncolytic adenoviruses that show efficacy in ovarian tumors which have become resistant to chemotherapy. Any other tumor cell line which is representative of a target tissue of interest, available through such sources as the ATCC, can be used in isolating adenoviruses of the invention.

Alternatively, directed evolution of the adenoviruses of the invention can be done directly on freshly excised human primary or metastatic tumor cells, including tumor cells from haematological malignancies.

In the present invention, adenoviral selection is performed using as the starting material an adenoviral mixture that includes serotypes representative of the adenoviral subgroups B, C, D, E and F. Group A adenoviruses are not included in the mixture as they are associated with tumor formation in rodents. In a preferred embodiment of the invention, the mixture also includes the chimeric adenovirus ColoAd1 (see U.S. patent application Ser. No. 11/136,912).

The pooled adenoviral mixture is passaged once, more preferably at least twice, on a subconfluent culture of tumor cells or on cells grown on in vitro 3D associations of extracellular matrix nanofibrils including, but not limited to, collagen and basement membrane matrix (MATRIGEL™, Becton Dickinson). It has been shown that the cellular architecture induced by such matrices are critical to the reproduction of physiological patterns of cell adhesion, cytoskeletal organization, signal transduction and gene expression, morphogenesis, and differentiation in cultures of both normal and transformed cells and that such extracts induce a cellular architecture important for the creation of model systems that more closely mimic the in vivo characteristics of abnormal cells (Schindler et al. *J Cell Biochem Biophys* (2006) 45:215-227; Birgersdotter et al. (2005) *Semin. Cancer Bio.* 15:405-412; Boyd et al. (2002) *J Gene Med* 4:567-576).

Initial passage of adenovirus is performed at a particle per cell ratio high enough to encourage recombination between serotypes, but not so high as to produce premature cell death. A preferred particle per cell ratio is between approximately 100-500 particles per cell, and is easily determined by one skilled in the art. As used herein, a "subconfluent culture" of cells refers to a culture in which the cells are actively growing. For cells grown as a monolayer, a subconfluent culture would be one in which approximately 50% to 80%, preferably 75%, of the area available for cell growth is covered with cells. For cells grown on a biological matrix material, a "subconfluent culture" would be one in which the cells do not confluently cover the matrix material.

Adenoviruses produced during these initial passages are used to infect quiescent tumor cells at a particle to cell ratio low enough to permit the infection of a cell by no more than one adenovirus and the supernatant for the subsequent passage harvested prior to visible cytopathic effect (CPE, see *Fields Virology*, Vol. 2, Fourth Edition, Knipe, ea., Lippincott Williams & Wilkins, pp. 135-136) to increase selection of highly potent viruses. After up to 20 passages under these conditions, the supernatant from the final passage, is again harvested prior to visible CPE and is then concentrated by techniques well known to those skilled in the art. One method for attaining quiescent cells, i.e. ones in which active cell growth has stopped, in a monolayer culture is to allow the culture to grow for 3 days following confluence, where confluence means that the entire area available for cell growth is occupied (covered with cells). For cultures grown on a 3D matrix, confluence is dependent on the cell type and can easily be determined by one of skill in the art. Suspension cultures can be grown to densities characterized by the absence of active cell growth.

The serotype profile of the concentrated supernatant harvested from the extracellular matrix material, which contains the bioselected adenoviral pool, can be examined by determining the retention times present within the harvested viral pool using an anion exchange column, where different adenoviral serotypes are known to have characteristic retention times (Blanche et al. (2000) *Gene Therapy* 7:1055-1062).

Adenoviruses of the invention can be isolated from the concentrated supernatant by dilution and plaque purification, or other techniques well know in the art, and grown for further characterization. Techniques well known in the art are used to determine the sequences of isolated oncolytic adenoviruses (see Example 5). Examples of oncolytic adenoviruses of the invention with selectivity for ovarian tumor cells derived by this method are OvAd1 (SEQ ID NO:1) and OvAd2 (SEQ ID NO:2), which were bioselected using MATRIGEL™ or a monolayer culture, respectively, during the selection process.

Figure 2A:
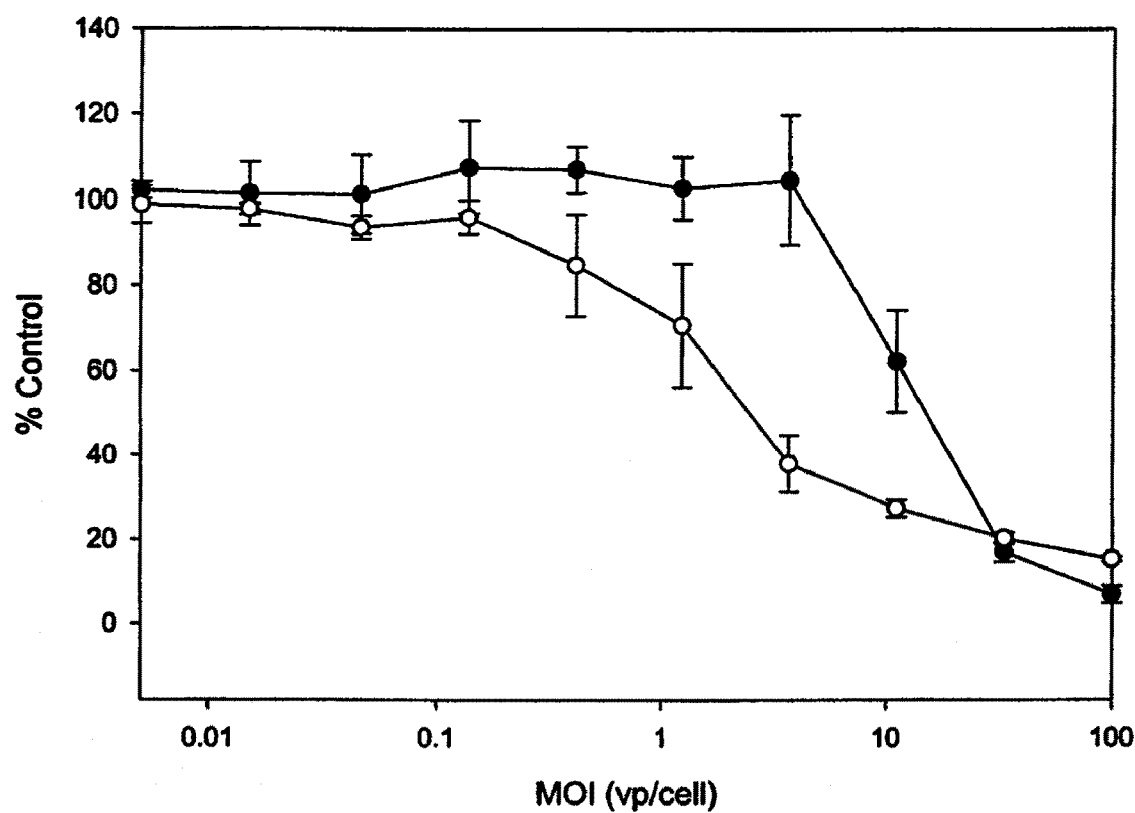
FIG. 2A. The therapeutic index of the adenoviral pool selected on MATRIGEL™ (SM10), is determined by comparing its potency ($IC_{50}$) on HUVEC endothelial cells (-●-) and SKOV3 platinum-resistant ovarian tumor cells (-○-).
Figure 2B:
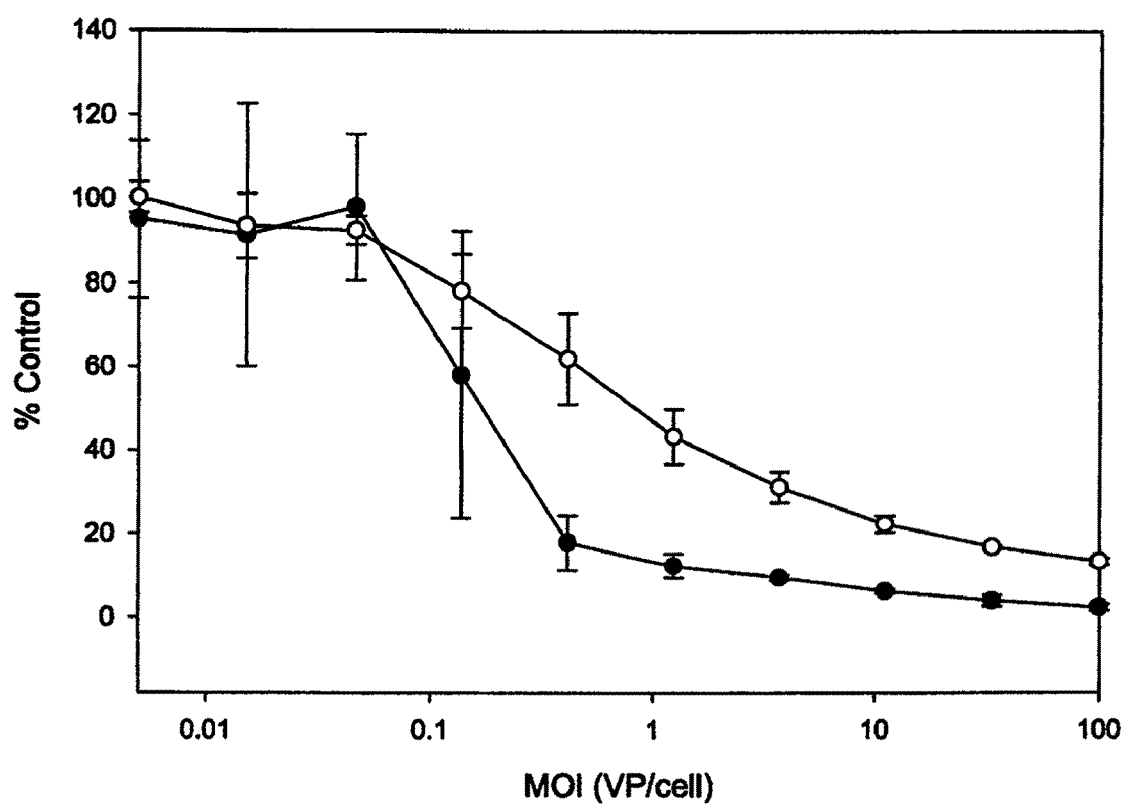
FIG. 2B. The therapeutic index of the adenoviral pool selected on monolayers (SP10), is determined by comparing its potency ($IC_{50}$) on HUVEC endothelial cells (-●-) and SKOV3 platinum-resistant ovarian tumor cells (-○-). MTS assays were read at 7 days post infection.
Figure 3:
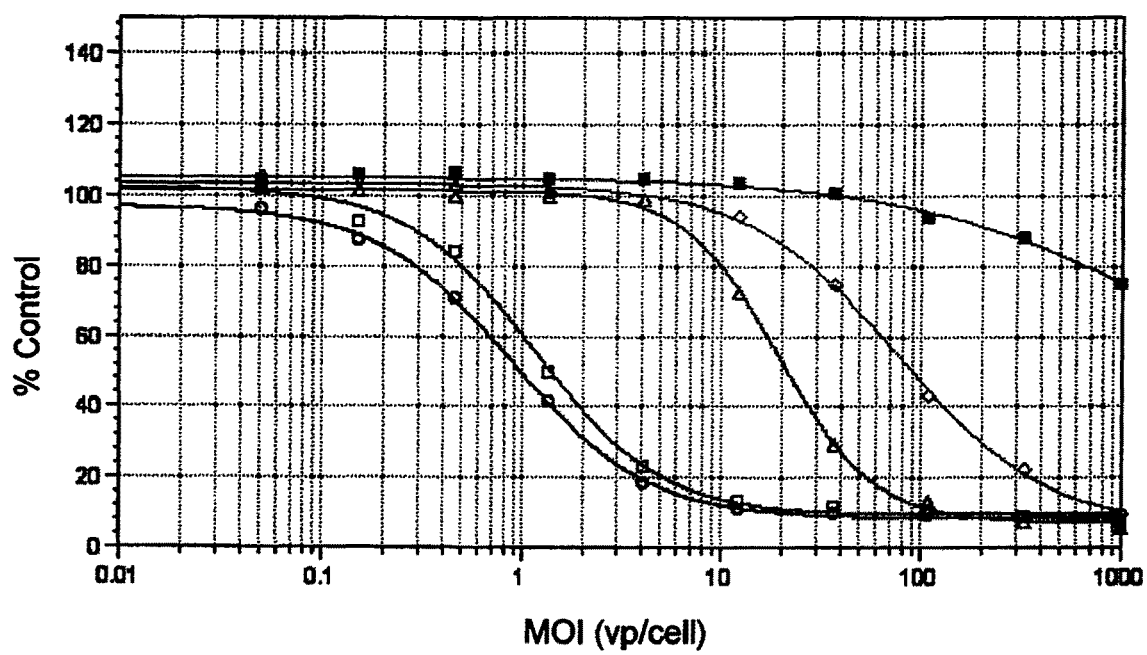
FIG. 3: Potency of adenoviruses OvAd1 and OvAd2. Individual adenoviruses, OvAd1 and OvAd2, were isolated from the SM10 (MATRIGEL™-selected) and SP10 (monolayer-selected) pools, respectively. The potency of the isolates OvAd1 (-○-) and OvAd2 (-□-) on SKOV3 cells was determined using the MTS assay and compared with the potency of the parental adenoviruses ColoAd1 (-Δ-) and Ad3 (-◇-) and the known oncolytic adenovirus, Onyx-015 (-■-). Results are shown at 7 days post infection.
Figure 4:
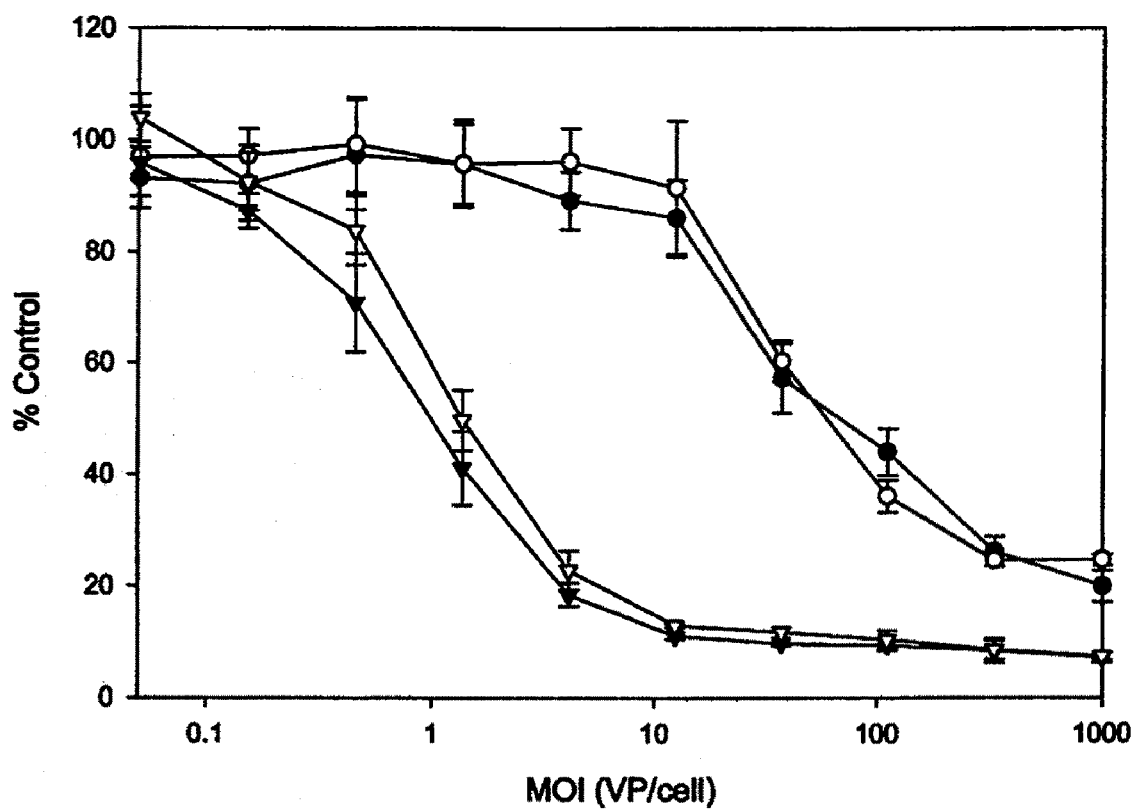
FIG. 4: Therapeutic index of adenoviruses OvAd1 and OvAd2. Individual adenoviruses, OvAd1 and OvAd2, were isolated from the SM10 (MATRIGEL™-selected) and SP10 (monolayer-selected) pools, respectively. The potency of each isolate was determined on SKOV3 and HUVEC cells. The symbols are as follows: OvAd1 on HUVEC (-●-); OvAd1 on SKOV3 (-▼-); OvAd2 on HUVEC (-○-); and OvAd2 on SKOV3 (-Δ-). Therapeutic index is determined by comparing adenoviral potency ($IC_{50}$) on SKOV3 platinum-resistant ovarian tumor cells and on HUVEC primary normal endothelial cells. Results are shown at 7 days post infection. Both OvAd1 and OvAd2 are about 100-fold more potent on SKOV3 cells than on HUVEC cells.

Adenoviruses of the invention have an enhanced potency/therapeutic index as compared with the adenoviral serotypes from which they are derived. FIGS. 1 and 2 demonstrate the potency and therapeutic index, respectively, of the viral pools derived on the MATRIGEL™ 3D extracellular cell matrix and on monolayer cells, while FIG. 4 shows similar data for individual adenoviral isolates from each pool: OvAd1 (from the MATRIGEL™ pool) and OvAd2 (from the monolayer pool).

Adenoviral Derivatives

The invention also encompasses an oncolytic adenovirus of the invention that is modified to provide other therapeutically useful oncolytic adenoviruses. Modifications include, but are not limited to, those described below.

One modification is production of derivatives of the oncolytic adenoviruses of the invention substantially lacking the ability to bind p53, as a result of a mutation in the adenoviral gene that encodes the E1B-55K protein. Such viruses generally have some, or all, of the E1B-55K region deleted. U.S. Pat. No. 6,080,578 describes, among other things, Ad5 mutants that have deletions in the region of the E1B-55K protein that is responsible for binding p53 (see also U.S. Pat. No. 5,677,178). Another preferred modification to the oncolytic adenoviruses of the instant invention are mutations in the E1A region, as described in U.S. Pat. Nos. 5,801,029 and 5,972,706. These types of modifications provide derivatives of the oncolytic adenoviruses of the invention with greater selectivity for tumor cells.

Another example of a modification encompassed by the invention is modification of an oncolytic adenovirus such that it exhibits an enhanced degree of tissue specificity due to placement of viral replication under the control of a tissue specific promoter as described in U.S. Pat. No. 5,998,205. Replication of an oncolytic adenovirus of the invention can also be put under the control of an E2F responsive element as described in U.S. patent application Ser. No. 09/714,409. This modification affords a viral replication control mechanism based on the presence of E2F, resulting in enhanced tumor tissue specificity, and is distinct from the control realized by a tissue specific promoter. In both of these embodiments, the tissue specific promoter and the E2F responsive element are operably linked to an adenoviral gene that is essential for the replication of the adenovirus.

Another modification encompassed by the invention is use of an oncolytic adenovirus of the invention, e.g. OvAd1 (SEQ ID NO:1) or OvAd2 (SEQ ID NO:2), as the backbone for production of novel replication-deficient adenoviral vectors. As described in Lai et al. ((2002) *DNA Cell Bio.* 21:895-913), adenoviral vectors which are replication deficient can be used to deliver and express therapeutic genes. Adenoviral vectors of the invention can be modified to produce replication deficient derivatives by deletion of the E1, E2 or E4 regions of the viral genome. Particularly preferred is deletion of the E1 or E2 regions. Such modified adenoviral vectors are easily produced using techniques well known to those skilled in the art (see Imperiale and Kochanek (2004) *Curr. Top. Microbiol. Immunol.* 273:335-357; Vogels et al. (2003) *J. Virol.* 77:8263-8271).

Similarly, other modifications can be made to the oncolytic adenoviruses of the invention to increase their potency by reducing the size of the viral genome by deletion of one or more regions or parts thereof. Also encompassed within the invention is modification of the adenoviruses of the invention through deletion of a section of the adenoviral genome which binds to the cellular Rb protein, commonly known as a "delta 24" deletion. Such deletions can result in adenoviruses with enhanced tumor specificity (Fueyo et al. (2000) *Oncogene* 19:2-12).

Another modification encompassed by the invention is deletion of the E3 region of the oncolytic adenoviruses of the invention to increase their potency by a mechanism distinct from reduction of genome size.

Methods for the construction of modified adenoviruses are generally known in the art. See, Mittal, S. K. (1993) *Virus Res.* 28:67-90 and Hermiston, T. et al. (1999) *Methods in Molecular Medicine: Adenovirus Methods and Protocols*, W. S. M. Wold, ed, Humana Press. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2nd edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art.

Determination of Therapeutic Potential

Oncolytic adenoviruses of the invention, or variants or derivatives thereof, can be evaluated for their therapeutic utility by examination of their lytic potential in tumor cells derived from tissues of interest as therapeutic targets. Tumor cell lines useful for testing adenoviruses of the invention include, but are not limited to, colon cell lines, including but not limited to, DLD-1, HCT116, HT29, LS1034 and SW48 cell lines; prostate cell lines, including but not limited to DU145 and PC-3 cell lines; pancreatic cell lines, including but not limited to, the Panc-1 cell line; breast tumor cell lines, including but not limited to, the MDA231 cell line; and ovarian cell lines, including but not limited to, the OVCAR-3, CaOV3, BG1, ES-2 and IGROV and SKOV3 cell lines. Any other tumor cell lines, available through sources such as the American Type Culture Collection, which are representative of a tissue target of interest; can be used in identifying and evaluating adenoviruses of the invention for use in the treatment of neoplasia of that tissue type. Alternatively, evaluation of the oncolytic adenoviruses of the invention can also be performed using matched human primary tumor and normal explants, e.g. through quantitation of viral burst (U.S. patent application Ser. No. 11/136,912) or reporter gene expression (Lam et al. (2003) *Cancer Gene Therapy* 10:377-387; Grill et al. (2003) *Mol. Therapy* 6:609-614). See Example 8.

The cytolytic activity of adenoviruses of the invention can be determined in representative tumor cell lines and the data converted to a measurement of potency (i.e. $IC_{50}$). A preferred method for determining cytolytic activity is an MTS assay (see Example 4).

The therapeutic index of an adenovirus of the invention in a particular tumor cell can be calculated by comparison of the potency of the given adenovirus in the tumor cell with the potency of that same adenovirus in a matched normal cell. Preferred non-cancerous cells are SAEC cells (Cambrex/Clonetics, Inc., Walkersville, Md.), which are epithelial in origin, and HUVEC cells (VEC Technologies, Rennselaer, N.Y.), which are endothelial in origin (see FIGS. 2 and 4). These two cell types represent normal cells from which organs and vasculature, respectively, are derived, and are representative of likely sites of toxicity during adenoviral therapy, depending on the mode of delivery of the adenovirus. However, practice of the invention is not limited to the use of these cells, and other non-cancerous cells (e.g. B cells, T cells, macrophages, monocytes, fibroblasts) may also be used.

Figure 6A:
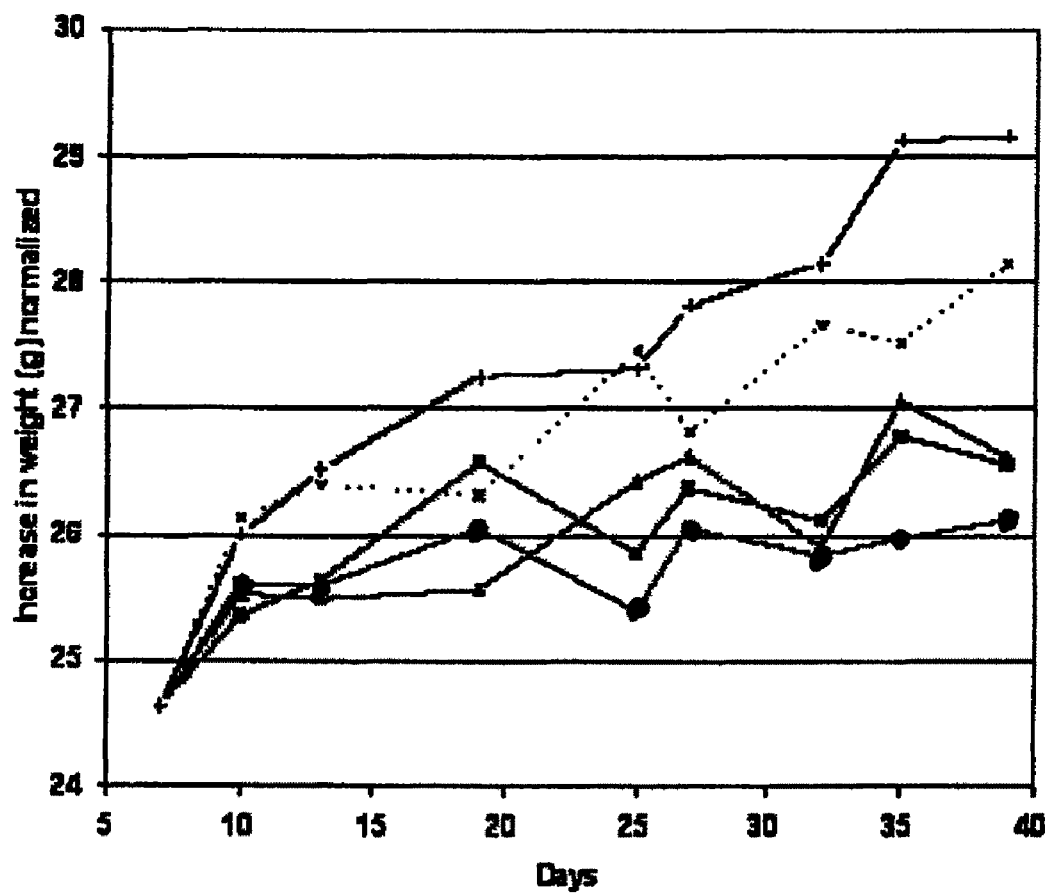
FIG. 6A. SKOV3 tumor cells were seeded to the peritoneal cavity of 25 mice on day 0. Mice were divided into 5 groups, and one of four kinds of virus OvAd1 (-●-), OvAd2 (-■-). ONYX-015 (-×-) and ColoAd1 (-▲-) or the vehicle control (-+-), was injected ip on days 3, 5, and 7 post tumor seeding. Mice were weighed every 4 to 6 days.

The oncolytic adenoviruses of the invention can be further evaluated for their ability to target neoplastic cell growth (i.e. cancer) by their capacity to reduce tumorigenesis or neoplastic cell burden in nude mice harboring a transplant of neoplastic cells, as compared to untreated mice harboring an equivalent neoplastic cell burden (see Example 6, FIGS. 6A and B).

Therapeutic Utility

The present invention provides for the use of the oncolytic adenoviruses of the invention for the inhibition of tumor cell growth, as well as for the use of adenoviral vectors derived from these adenoviruses to deliver therapeutic proteins useful in the treatment of neoplasia.

Pharmaceutical Compositions and Administration

The present invention also relates to pharmaceutical compositions which comprise the chimeric/oncolytic adenoviruses of the invention, including variants and derivatives thereof, formulated for therapeutic administration to a patient. For therapeutic use, a sterile composition containing a pharmacologically effective dosage of adenovirus is administered to a human patient or veterinary non-human patient for treatment, for example, of a neoplastic condition. Generally, the composition will comprise about $10^{11}$ or more adenovirus particles in an aqueous suspension. A pharmaceutically acceptable carrier or excipient is often employed in such sterile compositions. A variety of aqueous solutions can be used, e.g. water, buffered water, 0.4% saline, 0.3%-glycine and the like. These solutions are sterile and generally free of particulate matter other than the desired adenoviral vector. The compositions may contain pharmaceutically acceptable auxiliary substances as required to approximate physiological conditions such as pH adjusting and buffering agents, toxicity adjusting agents and the like, e.g. sodium acetate, sodium chloride, potassium chloride, calcium chloride, sodium lactate, etc. Excipients which enhance infection of cells by adenovirus may be included. (see U.S. Pat. No. 6,392,069).

Adenoviruses of the invention may also be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of adenovirus virions can be encapsulated in micelles to form immunoliposomes by conventional methods (U.S. Pat. No. 5,043,164, U.S. Pat. No. 4,957,735, U.S. Pat. No. 4,925,661; Connor and Huang, (1985) *J. Cell Biol.* 101: 581; Lasic D. D. (1992) *Nature* 355: 279; Novel Drug Delivery (eds. Prescott and Nimmo, Wiley, New York, 1989); Reddy et al. (1992) *J. Immunol.* 148:1585). Immunoliposomes comprising an antibody that binds specifically to a cancer cell antigen (e.g., CALLA, CEA) present on the cancer cells of the individual may be used to target virions to those cells (Fisher (2001) *Gene Therapy* 8:341-348).

To further increase the efficacy of the adenoviruses of the invention, they may be modified to exhibit enhanced tropism for particular tumor cell types. For example, as shown in PCT/US98/04964, a protein on the exterior coat of an adenovirus may be modified to display a chemical agent, preferably a polypeptide, that binds to a receptor present on tumor cells to a greater degree than normal cells. (See also, U.S. Pat. Nos. 5,770,442 and 5,712,136). The polypeptide can be an antibody, and preferably is a single chain antibody.

Adenoviral Therapy

The adenoviruses of the invention, or pharmaceutical compositions thereof, can be administered for therapeutic treatment of neoplastic disease or cancer. In therapeutic applications, compositions are administered to a patient already affected by the particular neoplastic disease, in an amount sufficient to cure or at least partially arrest the condition and its complications. An amount adequate to accomplish this is defined as a "therapeutically effective dose" or "efficacious dose". Amounts effective for this use will depend upon the severity of the condition, the general state of the patient, and the route of administration.

For example, but not by way of limitation, a human patient or non-human mammal having a solid or haemotologic neoplastic disease, (e.g. pancreatic, colon, ovarian, lung, or breast carcinoma, leukemia or multiple myeloma) may be treated by administering a therapeutically effective dosage of an appropriate oncolytic adenovirus of the invention, i.e. one which has been shown to have an improved therapeutic index for that tissue type. A preferred oncolytic adenovirus for the treatment of ovarian cancer would be the adenovirus OvAd2 (SEQ ID NO: 2). A particularly preferred oncolytic adenovirus for the treatment of ovarian cancer would be OvAd1 (SEQ ID NO:1).

Suspensions of infectious adenovirus particles may be delivered to neoplastic tissue by various routes, including intravenous, intraperitoneal, intramuscular, intratumoral, subdermal, and topical. An adenovirus suspension containing about $10^3$ to $10^{12}$ or more virion particles per ml may be administered by infusion (e.g., into the peritoneal cavity for treating ovarian cancer).

Adenoviral therapy using the adenoviruses of the instant invention may be combined with other antineoplastic protocols, such as conventional chemotherapy or x-ray therapy to treat a particular cancer.

Adenoviral therapy using the adenoviruses of the instant invention as adenoviral vectors may also be combined with other genes known to be useful in viral based therapy. See U.S. Pat. No. 5,648,478. In such cases, the chimeric/oncolytic adenovirus further comprises a heterologous gene that encodes a therapeutic protein, incorporated within the viral genome, such that the heterologous gene is expressed within an infected cell. A therapeutic protein, as used herein, refers to a protein that would be expected to provide some therapeutic benefit when expressed in a given cell.

In one embodiment, the heterologous gene can be the thymidine kinase (TK) gene, which is useful as a pro-drug converting enzyme (Freeman, S. M. (2000) *Adv Exp Med Biol* 465:411-422). TK can also be used as a marker or reporter for tracking the efficiency of viral infection (Sangro et al. (2002) *Mol. Imaging Biol.* 4:27-33).

In one embodiment, the heterologous gene is a pro-drug activator gene, such as cytosine deaminase (CD) (See, U.S. Pat. Nos. 5,631,236; 5,358,866; and 5,677,178). In other embodiments, the heterologous gene is a known inducer of cell-death, e.g. apoptin or adenoviral death protein (ADP), or a fusion protein, e.g. fusogenic membrane glycoprotien (Danen-Van Oorschot et al. (1997) *Proc. Nat. Acad. Sci.* 94:5843-5847; Tollefson et al. (1996) *J. Virol.* 70:2296-2306; Fu et al. (2003) *Mol. Therapy* 7: 48-754, 2003; Ahmed et al. (2003) *Gene Therapy* 10:1663-1671; Galanis et al. (2001) *Human Gene Therapy* 12(7): 811-821).

Further examples of heterologous genes, or fragments thereof, include those that encode immunomodulatory proteins, such as cytokines or chemokines. Examples include interleukin 2, U.S. Pat. Nos. 4,738,927 or 5,641,665; interleukin 7, U.S. Pat. Nos. 4,965,195 or 5,328,988; and interleukin 12, U.S. Pat. No. 5,457,038; tumor necrosis factor alpha, U.S. Pat. Nos. 4,677,063 or 5,773,582; interferon gamma, U.S. Pat. Nos. 4,727,138 or 4,762,791; or GM CSF, U.S. Pat. Nos. 5,393,870 or 5,391,485, Mackensen et al. (1997) *Cytokine Growth Factor Rev.* 8:119-128). Additional immunomodulatory proteins include macrophage inflammatory proteins, including MIP-3. Monocyte chemotactic protein (MCP-3 alpha) may also be used; a preferred embodiment of a heterologous gene is a chimeric gene consisting of a gene that encodes a protein that traverses cell membranes, for example, VP22 or TAT, fused to a gene that encodes a protein that is preferably toxic to cancer but not normal cells.

Another example of a heterologous gene is an antibody or antibody fragment. Preferred antibodies are targeted against epidermal growth factor (EGF) or tissue factor (TF) (Jiang et al. (2006) *Clin Cancer Res* 12:6179-6185; Kasuya et al. (2005) *Mol Ther* 11:237-244)

The oncolytic adenoviruses of the invention can also be used as vectors to deliver genes encoding therapeutically useful RNA molecules, i.e. siRNA (Dorsett and Tuschl (2004) *Nature Rev Drug Disc* 3:318-329), shRNA, or miRNA or aptamers.

In some cases, genes can be incorporated into an oncolytic adenovirus of the invention to further enhance the ability of the oncolytic virus to eradicate the tumor, although not having any direct impact on the tumor itself—these include genes encoding proteins that compromise MHC class I presentation (Hewitt et al. (2003) *Immunology* 110: 163-169), block complement, inhibit IFNs and IFN-induced mechanisms, chemokines and cytokines, NK cell based killing (Orange et al., (2002) *Nature Immunol.* 3: 1006-1012; Mireille et al. (2002) *Immunogenetics* 54: 527-542; Alcami (2003) *Nature Rev. Immunol.* 3: 36-50; down regulate the immune response (e.g. IL-10, TGF-Beta, Khong and Restifo (2002) *Nature Immunol.* 3: 999-1005; 2002) and metalloproteases which can breakdown the extracelluar matrix and enhance spread of the virus within the tumor (Bosman and Stamenkovic (2003) *J. Pathol.* 2000: 423-428; Visse and Nagase (2003) *Circulation Res.* 92: 827-839).

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

The present invention is further described by the following examples, which are illustrative of specific embodiments of the invention, and various uses thereof. These exemplifications, which illustrating certain specific aspects of the invention, do not portray the limitations or circumscribe the scope of the disclosed invention.

Unless otherwise indicated, the practice of the present invention employs conventional techniques of cell culture, molecular biology, microbiology, recombinant DNA manipulation, immunology science, which are within the skill of the art. Such techniques are explained fully in the literature. See, e.g. Cell Biology: a Laboratory Handbook: J. Celis (Ed). Academic Press. N.Y. (1996); Graham, F. L. and Prevec, L. Adenovirus-based expression vectors and recombinant vaccines. In: Vaccines: New Approaches to Immunological Problems. R. W. Ellis (ed) Butterworth. Pp 363-390; Grahan and Prevec Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109-128, 1991; Sambrook et al. (1989), Molecular Cloning, A Laboratory Manual, 2nd ed., Cold Spring Harbor Laboratory Press; Sambrook et al. (1989), and Ausubel et al. (1995), Short Protocols in Molecular Biology, John Wiley and Sons.

EXAMPLES

Methods

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., Molecular Cloning: A Laboratory Manual, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation and delivery, and treatment of patients. Methods for the construction of adenoviral mutants are generally known in the art. See, Mittal, S. K. *Virus Res.,* 1993, vol: 28, pages 67-90; and Hermiston, T. et al., Methods in Molecular Medicine: Adenovirus Methods and Protocols, W. S. M. Wold, ed., Humana Press, 1999. The adenovirus 5 genome is registered as Genbank 10 accession #M73260, and the virus is available from the American Type Culture Collection, Rockville, Md., U.S.A., under accession number VR-5.

Viruses and Cell Lines

The human Ad serotypes Ad3 (GB strain), Ad4 (RI-67 strain), Ad5 (Adenoid 75 strain), Ad9 (Hicks strain), Ad16 (Ch. 79 strain); and the SKOV3, OVCAR3, CaOV3, IGROV, BG1, ES-2, PC-3, and HT-29 cell lines used were all purchased from the ATCC. The chimeric adenovirus ColoAd1 is described in U.S. patent application Ser. No. 11/136,912. Ad35, Ad11p (Slobitski strain), and Ad40 were kind gifts from Dr. William S. M. Wold at St Louis University. Other cells used were MDA-231mt1 (a cell line derivative isolated by Dr. Deb Zajchowski, Berlex Laboratories, from a rapidly growing subcutaneously implanted xenograft of MDA-231 cells) and Panc1-sct (derived by Dr. Sandra Biroc, Berlex Laboratories, from a rapidly growing subcutaneously implanted xenograft of Panc1 cells), HUVEC (Vec Technologies, Rensselaer, N.Y.), and SAEC (Clonetics, Walkersville, Md.).

Example 1

Viral Purification and Quantitation

Viral stocks were propagated on either 293 cells or SKOV3 cells, purified on CsCI gradients, and titered (viral particles per ml, vp/ml, is the unit used throughout this report) by spectroscopy (Tollefson, A., Hermiston, T. W., and Wold, W. S. M.; "Preparation and Titration of CsCI-banded Adenovirus Stock" in *Adenovirus Methods and Protocols*, Humana Press, 1999, pp 1-10, W. S. M. Wold, Ed) and by anion-exchange (AIEX) chromatography (Kuhn et al. (2006) *Gene Therapy*). Most Ad serotypes have distinct, characteristic retention profiles when analyzed by the AIEX method used, and viral purification is not necessary to determine an accurate titer by AIEX, allowing accurate quantification of crude lysates as described (ibid.). Therefore AIEX chromatography was used to verify the spectroscopic titer of pure viral stocks, to determine the titer of crude viral lysates, and to partially characterize the serotype-relatedness of all viral stocks.

The method used to quantitate viral particles is as described in Kuhn et al. (2006) *Gene Therapy* published on-line. In brief, a 1.25 ml column was packed with Q Sepharose XL Media (Pharmacia). HPLC separation was performed on an Agilent HP 1100 HPLC using the following conditions: Buffer A=20 mM TrisHCl, pH 7.5; Buffer B=1.0 M NaCl in Buffer A; flow rate of 1 ml per minute. After column equilibration for not less than 30 minutes in Buffer A, approximately $10^9$-$10^{11}$ viral particles of sample were loaded onto the column in 10-100 ul volume, followed by 4 column volumes of Buffer A. A linear gradient extending over 16 column volumes and ending in 100% Buffer B was applied.

The column effluent was monitored at A260 and A280 nm, peak areas calculated, and the 260 to 280 nm ratio determined. Viral peaks were identified as those narrow, sharp peaks having a A260/A280 ratio close to 1.33. A virus standard was included with each sample series. The number of viral particles per ml of the standard had been determined using the method of Lehmberg et al. (1999) *J. Chrom. B*, 732:411-423}. In the viral concentration range used, the A260 nm peak area of each sample is directly proportional to the number of viral particles in the sample. The number of viral particles per ml in each test sample was calculated by multiplying the known number of viral particles per ml in the standard by the ratio of the A260 nm viral peak area of the sample to the A260 nm viral peak area of the standard.

The column was regenerated after each sample gradient by washing with at least two column volumes of 0.1-0.5 N NaOH followed by two column volumes of 100% Buffer A, 3 column volumes of 100% Buffer B, and then 4 column volumes of 100% Buffer A.

Example 2

Directed Evolution

Viral serotypes representing subgroup Ads B-F, namely Ad3, Ad4, Ad5, Ad9, Ad11p, Ad16, Ad35, Ad40, and the chimeric virus ColoAd1 (U.S. patent application Ser. No. 11/136,912)) were assembled into the starting viral pool. A portion of the starting pool, containing $10^{12}$ viral particles of each viral type, was subjected to random mutagenesis by nitrous acid (Williams et al. (1971) *J Gen Virol* 11:95-101; Klessig, D. F. (1977) *J. Viral.* 21:1243-1246). The reaction was stopped by neutralization of the nitrous acid after 2.5-3 logs of kill. A 356 by region of the 19 K protein was amplified from each of 10 viral isolates from a parallel Ad5 mutagenized stock and sequenced. Sequencing showed that one in ten isolates carried a point mutation. Extrapolation from this result indicates that approximately 10 mutations were introduced on average per viral genome. The pool of mutagenized virus serotypes was called the mutagenized pool. Another portion of the starting pool, containing $10^9$ viral particles of each viral type, was then added to the mutagenized pool, resulting in a combined pool containing approximately equal numbers of mutagenized and non-mutagenized viral particles of each viral type. This combined pool was used to infect, at a multiplicity of infection (MOI)=10, subconfluent monolayers of SKOV3, HT-29, and OVCAR3 cells. These infection conditions were chosen to invite recombination between all viral types present in the combined (mutagenized and non-mutagenized) viral pool. Viral lysates were harvested from these infected cultures at 24 and 48 hours post infection (hpi), then mixed together to produce the "recombined pool." A fresh aliquot of the combined pool was then added to this recombined pool to generate the viral pool used for directed evolution. The titer of this pool was determined by anion exchange chromatography as described above.

Directed Evolution on monolayer cultures: The biodiverse viral pool was passaged once on a sub-confluent culture of SKOV3 cells at MOI=10, a high particle-per-cell ratio again used to invite recombination between all viruses present in the biodiverse pool. The titer of the viral lysate supernatant from this round of high viral particle-per-cell infection of subconfluent SKOV3 monolayer cells was determined by AIEX chromatography, then used in a 10-fold dilution series, starting at an MOI=0.1, to infect a series of over-confluent SKOV3 cultures grown in 6-well plates. To achieve over-confluency, SKOV3 cells were seeded at split ratios that allowed that cell line to reach confluency between 24 and 40 hours post seeding, and the cells were allowed to grow a total of 72 hours post seeding prior to infection. This cell density was 150,000 cells per $cm^2$. This high cell density and prolonged growth was used to maximize confluency at time of infection, with the goal of mimicking growth conditions in human solid tumors. Cell culture supernatant was harvested from the well infected with the most concentrated innocula in the 10-fold dilution series that did not show any sign of CPE at day 3 or 4 post-infection. Each harvest served as the starting material for the next passage of the virus. This process was repeated until the viral pool achieved 10 passages.

Directed evolution on MATRIGEL™ cultures: Directed evolution using SKOV3 cells grown on growth factor reduced MATRIGEL™ (Becton Dickinson Labware, Bedford, Mass.) coated tissue cultures plates as the target cell culture was done generally as described for directed evolution on monolayer cultures, with the exceptions that the culture dishes or wells were coated, following manufacturer's directions, with MATRIGEL™ at 150 ul/$cm^2$ prior to seeding the cells. SKOV3 cells were seeded onto MATRIGEL™-coated plates at about 150,000 cells per $cm^2$, a density that generated obvious three-dimensional growth patterns in these cells by 24 hours post seeding (hps). The cells were infected 24-36 hours post seeding, i.e. soon after the three-dimensional growth patterns induced by MATRIGEL™ had become apparent in the cultures. One passage at MOI=10 was done to invite recombination between all the viral genomes in the pool before starting selective passaging. Selective passaging on MATRIGEL™ was done, as described for monolayer directed evolution, starting at an MOI of less than one viral particle per cell (to avoid complementation between genotypes), followed by three 10-fold serial dilutions. In this way, 10-fold serial dilutions (starting at an MOI=0.1) of the previous selective passage supernatant were used to infect a series of SKOV3 cultures grown on MATRIGEL™. At each passage, culture supernatant was harvested from the culture infected with the most concentrated inoculates in the 10-fold dilution series that did not show any sign of CPE at day 3 or 4 post-infection. A total of 10 passages were performed before individual viruses were isolated and characterized from each selected pool.

The selected pools were analyzed by ion exchange chromatography, which demonstrated that the viral pool selected on SKOV3 monolayers was composed of Ad-3 related viruses, while the pool derived on MATRIGEL™ contains both Ad3 and Ad11p/35-related viruses.

Example 3

Isolation and Characterization of Selected Viruses

Individual viruses were isolated from each selected pool by two rounds of plaque purification on SKOV3 cells using standard methods (Tollefson, A., Hermiston, T. W., and Wold, W. S. M.; "Preparation and Titration of CsCI-banded Adenovirus Stock" in *Adenovirus Methods and Protocols*, Humana Press, 1999, pp 1-10, W. S. M. Wold, Ed). In brief, dilutions of the supernatant harvested from the $10^{th}$ passage on SKOV3 cells grown either as monolayers, or on top of MATRIGEL™, were used to infect SKOV3 cells in a standard plaque assay. Individual plaques were harvested, and the same plaque assay method was used to generate a second round of individual plaques from these harvests. Plaques from the second round of plaque purification were deemed pure, infected cultures of A549 cells were prepared using these purified plaques, and the oncolytic potency of these culture lysates determined by MTS assay as described.

Example 4

Cytolytic Assay

Viral lytic capacity was measured using a modification of the MTT assay (Yan et al. (2003) *J Virol* 77:2640-2650). Briefly, the MTS assay (Promega, CellTiter 96® Aqueous Non-Radioactive Cell Proliferation Assay) was used in place of the MTT assay because conversion of MTS into cells into aqueous, soluble formazan reduces time and eliminates the use of a volatile organic solvent associated with the MTT assay.

To perform the MTS assay, cells were seeded at a density determined for each tumor cell line to generate a confluent monolayer within 24 hours. These densely seeded cells were allowed to grow for 2 additional days prior to exposure to the test virus(es). Viral lysates or stocks to be assayed for potency by MTS assay were titered by anion exchange (AIEX) chromatography as described above. Infections of both tumor and primary normal cells were carried out in quadruplicate, using serial three fold dilutions of the viruses starting at a particle per cell ratio of 100 and ending at a particle per cell ratio of 0.005. Infected cells were incubated at 37° C. and the MTS assay was performed at the time points indicated for the individual primary cells or tumor cell lines. Mock-infected cells served as negative controls and established the 100% survival point for the given assay. Each data point in any given MTS assay was assessed in quadruplicate, and $IC_{50}$ values were derived from dose response curves with $R^2v$ value of 0.9 or greater. Each MTS assay was repeated at least twice, with consistent results.

When performed on MATRIGEL™-grown cell cultures, the MTS assay method was modified as follows. 96-well plates were coated with Growth Factor Reduced MATRIGEL™ (Becton-Dickinson) at 0.15 ml/cm². Cells were seeded on top of the MATRIGEL™ at densities that generated 3-dimensional growth within 24 hours post seeding. For SKOV3 cells, the seeding density was 150,000 cells/cm². For HUVEC cells, the seeding density was 100,000 cells/cm². Viruses were added to cells at 24 hours post seeding, using 3-fold serial dilutions of the viruses starting at a particle per cell ratio of 1,000 and ending at a particle per cell ratio of 0.05.

Example 5

DNA Sequencing

Sequencing of the isolated adenoviruses OvAd1 (SEQ ID NO:1) and OvAd2 (SEQ ID NO:2) was accomplished as follows. A shotgun library was prepared using sheared purified template DNA. The sheared DNA was size-selected for the range 2-4 kb before insertion into the pUC18 vector. Library construction was done by the double-adapter method described in Anderson et al. (1996) *Anal. Biochem.* 236:107-113. DNA cycle sequencing was performed on the PCR products using Big Dye Terminator v3.1 chemistry in conjunction with primers provided to SeqWright (M13 forward primer, 5'-GTAAAACGACGGCCAGT-3' (SEQ ID NO:5); M13 reverse primer, 5'-CAGGAAACAGCTATGAC (SEQ ID NO:6)). Sequence delineation and base-calling was performed using automated fluorescent DNA sequencers, ABI model 3730xl. All data including the final contig assembly was evaluated using a Phred20 scoring criteria Sequence assembly and editing was carried out using Sequencher 4.5 Software (GeneCodes, Inc.). Sequence information was analyzed using the Vector NTI program (Informatix).

Figure 5:
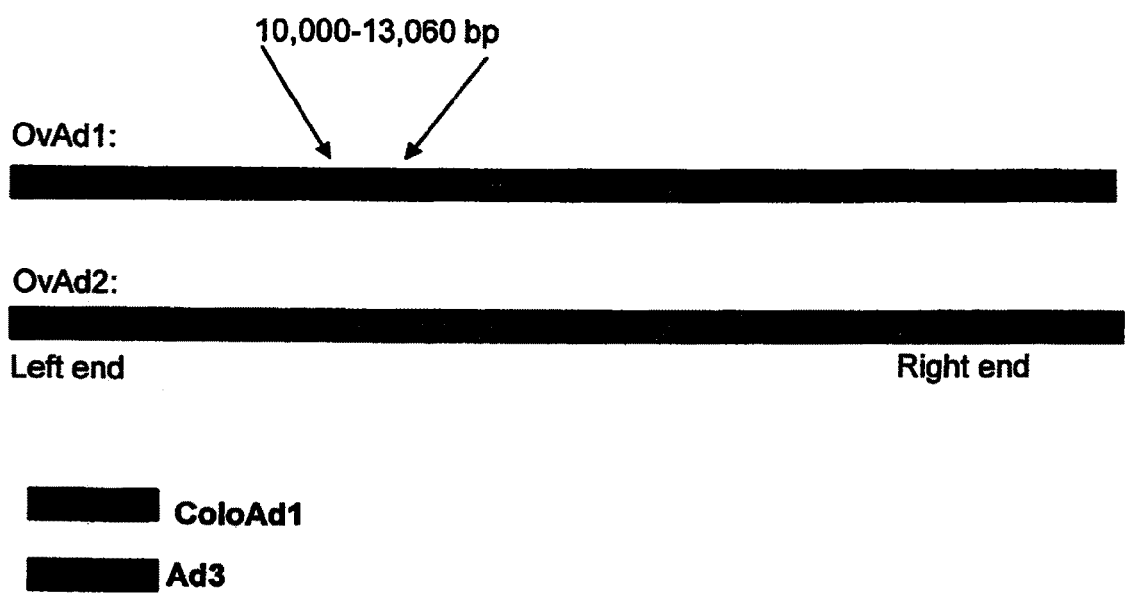
FIG. 5. Relationship of OvAd1 and OvAd2 sequences to ColoAd1 and Ad3. DNA sequence analysis of OvAd1 (SEQ ID NO:1) and OvAd2 (SEQ ID NO:2) revealed that both viruses are chimeras of the sequences ColoAd1 (SEQ ID NO:3) and Ad3 (SEQ ID NO:4). The region between 10,000 bp and 13,060 bp on the OvAd1 sequence is an area of non-homology between OvAd1 and OvAd2.

The sequences of OvAd1 (SEQ ID NO:1) and OvAd2 (SEQ ID NO:2) were compared to the DNA sequence of ColoAd1 (SEQ ID NO:3; see U.S. patent application Ser. No. 11/136,912) and to the DNA sequences of each of the other serotypes included in the starting viral pool. These analyses showed that OvAd1 and OvAd2 are chimeras of ColoAd1 (including the ColoAd1 chimeric E2B region) and serotype Ad3 (right end) (SEQ ID NO:4). See FIG. 5.

Example 6

In Vivo Efficacy of Adenoviruses

Figure 6B:
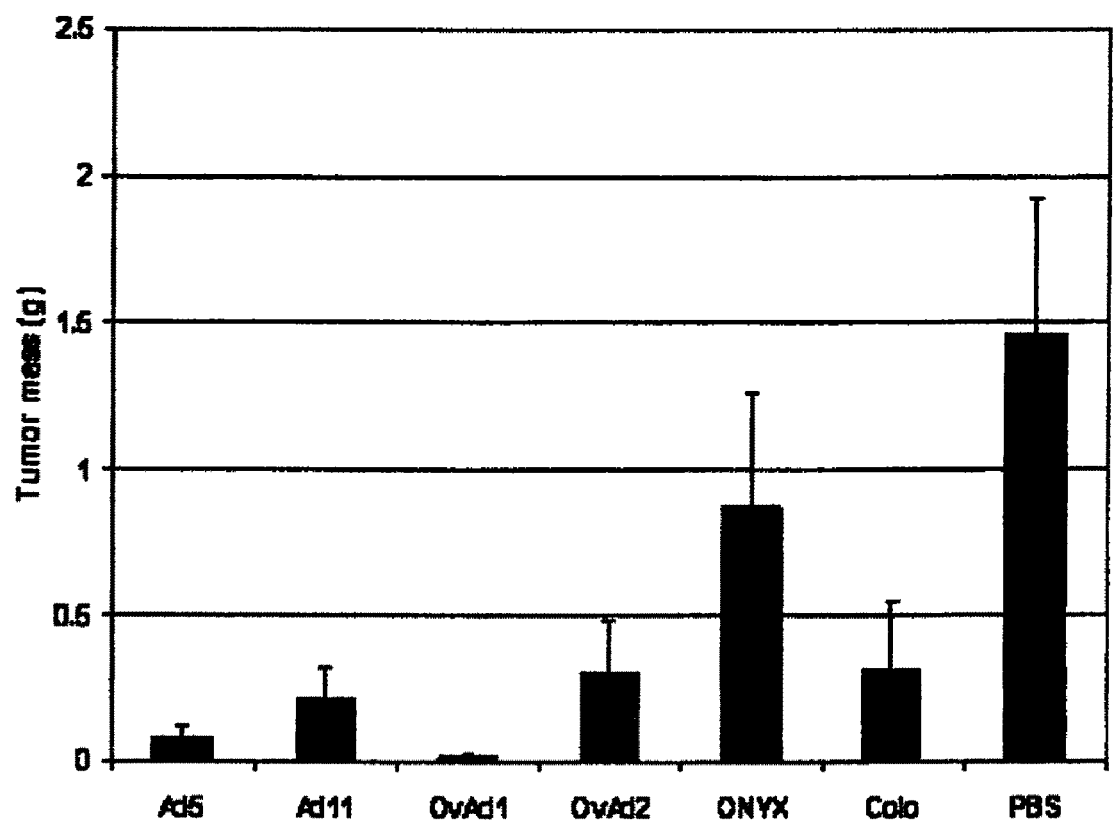
FIG. 6B. On day 41, mice were euthanized, the tumors dissected out and weighed (n=5).
Figure 7A:
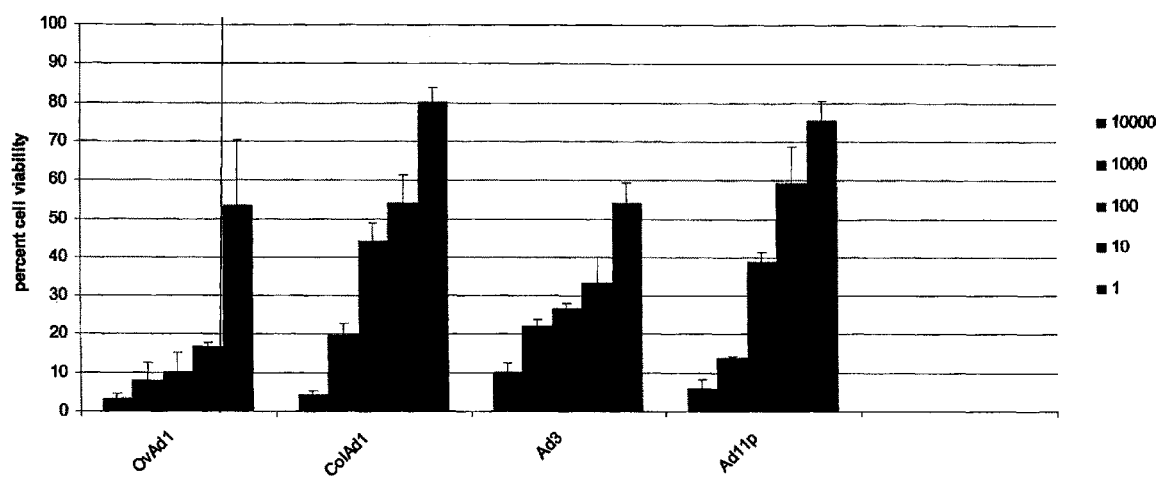
FIG. 7: From Lieber and Strauss; potency of OvAd1 against ovarian cancer progenitor, or stem, cells from a Stage 4 ovarian cancer patient.
Figure 7B:
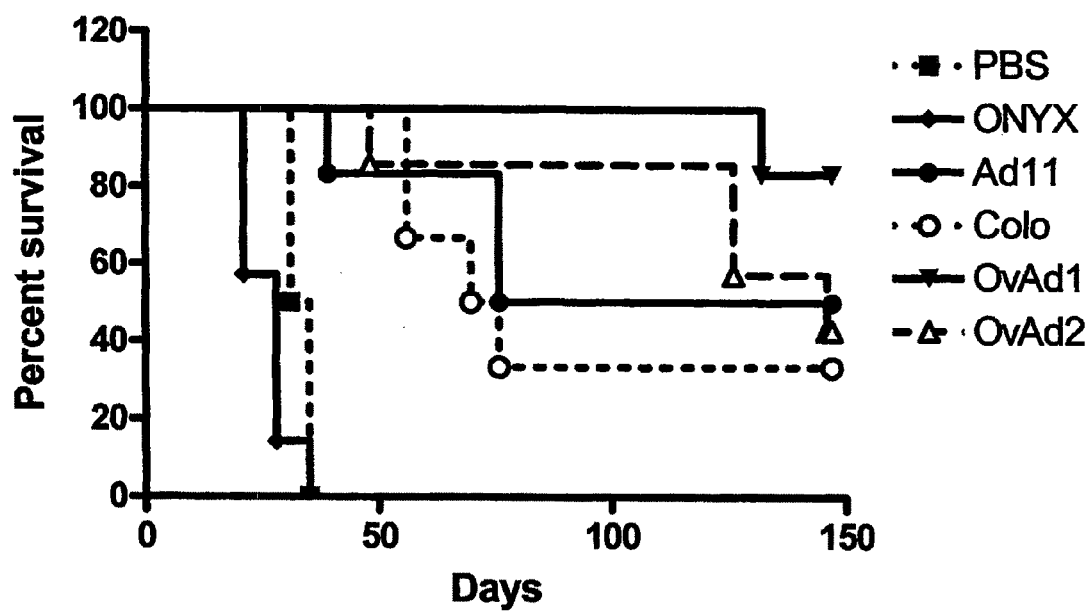

Efficacy of OvAd1 and OvAd2 in reducing tumor burden was shown in SKOV3 intraperitoneal tumour burden studies comparing anti cancer efficacy of Ad5, Onyx-015, OvAd1, OvAd2, ColoAd1 and PBS. The studies were done using MF1 nude mice (5 per group first run; 7 per group on the repeat experiment). SKOV3 cells were administered into the peritoneal cavity of each mouse, 5×10e6 cells per mouse, on day 0. The viruses were administered intraperitoneally, 5×10e10 virus particles or vehicle administered on days 3, 5, and 7 in 0.5 ml PBS. There were no signs of acute toxicity (breathing difficulties, hunch, death, starry coat) observed following administration of any vector. Extensive peritoneal organ adhesions were observed in mice treated with either Ad5 or ONYX-015 viruses. These adhesions can be fatal. None of the non Ad5-based viruses (OvAd1, OvAd2, ColoAd1, or Ad11p) showed any signs of adhesions. Blood samples were taken 1 hour following the final vector administration; no vectors were detected in the blood stream, indicating that there is no peritoneal leakage of these viruses. All mice were euthanized and tumor burden measured after 18 days (the day on which the tumor burden in control mice became excessive). In this model the OvAd1 virus was the most effective in reducing tumor burden, followed in efficacy by OvAd2 and the parental virus ColoAd1 and Ad11p. Ad5 was effective at reducing tumor burden but also caused extensive adhesions. Onyx-015 was ineffective. (See FIGS. 6A and 6B).

This study was repeated, except that SKOV3-luciferase cells were used and the mice were not euthanized until they acquired excessive tumor burdens. Tumor burden was followed during the study using whole-mouse imaging after luciferin injection. The imaging results were consistent with the tumor burdens measured in the in vivo SKOV3 study described above. Further, survival of mice in the various treatment groups showed that mice in the Onyx-015 group died within the first 21 days while OvAd1 treated mice were still alive after 45 days.

Example 7

Ex vivo Efficacy of Adenoviruses

Ovarian ascites tumor cell samples removed during surgery were placed in culture media and infected with equal numbers of OvAd1, OvAd2, ColoAd1, Ad3 or Onyx-015 adenoviral particles. Cell viability is measured after 5 days using MTS assay (described under cytolytic assay).

Example 8

Activity of OvAd1 on Primary Human Pluripotent Ovarian Cancer Progenitor Cells

Ovarian tumor and matched normal tissue samples are removed during surgery, cultured separately and infected with equal numbers of OvAd1, OvAd2, Ad5, or Onyx-015 adenoviral particles. After 2-6 days the culture supernatant and the cells are harvested, DNA purified from each sample, and the number of viral genomes measured in each sample by Taqman assay using genome-specific probes.

We claim:

1. An oncolytic isolated adenovirus which comprises a nucleotide sequence selected from the group consisting of SEQ ID NO:1 and SEQ ID NO:2.

2. The adenovirus of claim 1, wherein the adenovirus comprises SEQ ID NO:1.

3. The adenovirus of claim 2, wherein the adenovirus comprises SEQ ID NO:2.

4. The adenovirus of claim 1, further comprising a heterologous gene, wherein said heterologous gene is expressed within a cell infected with said adenovirus.

5. The adenovirus of claim 4, wherein said heterologous gene is thymidine kinase.

6. The adenovirus of claim 4, wherein said heterologous gene encodes a therapeutic protein selected from the group consisting of cytokines and chemokines, antibodies, factors known to induce cell death, pro-drug converting enzymes and immunoregulatory proteins.

7. The oncolytic adenovirus of claim 1, further comprising a heterologous gene encoding an immunoregulatory protein.

8. A method of inhibiting growth of a cancer cell, comprising infecting said cancer cell with the oncolytic adenovirus of claim 1.

9. The method of claim 8, wherein said cancer cell is an ovarian cancer cell.

10. The method of claim 9, wherein said cancer cell is a drug-resistant ovarian cancer cell.

11. The method of claim 8, wherein the adenovirus comprises SEQ ID NO:1.

12. The method of claim 8, wherein the adenovirus comprises SEQ ID NO:2.

* * * * *

```
                        SEQUENCE LISTING

<160> NUMBER OF SEQ ID NOS: 6

<210> SEQ ID NO 1
<211> LENGTH: 35130
<212> TYPE: DNA
<213> ORGANISM: adenovirus

<400> SEQUENCE: 1
tctatctata taatatacct tatagatgga atggtgccaa tatgtaaatg aggtgatttt      60
aaaaagtgtg gatcgtgtgg tgattggctg tggggttaac ggctaaaagg ggcggtgcga     120
ccgtgggaaa atgacgtttt gtggggggtgg agtttttttg caagttgtcg cgggaaatgt    180
gacgcataaa aaggcttttt tctcacggaa ctacttagtt ttcccacggt atttaacagg    240
aaatgaggta gttttgaccg gatgcaagtg aaaattgttg attttcgcgc gaaaactgaa    300
tgaggaagtg tttttctgaa taatgtggta tttatggcag ggtggagtat ttgttcaggg    360
ccaggtagac tttgacccat tacgtggagg tttcgattac cgtgtttttt acctgaattt    420
ccgcgtaccg tgtcaaagtc ttctgttttt acgtaggtgt cagctgatcg ctagggtatt    480
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agcttttga gcctcctacg cttcaggaac tgtatgattt     720
agaggtagag ggatcggagg attctaatga ggaagctgta aatggcttt ttaccgattc      780 tatgctttta gctgctaatg aagggttaga attagatccg cctttggaca cttttgatac    840 tccagggta attgtgaaa gcggtacagg tgtaagaaaa ttacctgatt tgagttccgt      900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat tcacaggaa    1080 aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
```

```
atctcctgat tctactacct cacctcctga gattcaagca cctgttcctg tggacgtgcg   1320
caagcccatt cctgtgaagc ttaagcctgg gaaacgtcca gcagtggaaa aacttgagga   1380
cttgttacag ggtggggacg gacctttgga cttgagtaca cggaaacgtc caagacaata   1440
agtgttccat atccgtgttt acttaaggtg acgtcaatat ttgtgtgaca gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagaacgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga cttttttgaag  1800 ctcttaattt gggccatcag gttcacttta aagaaaaagt tttatcagtt ttagactttt   1860
caaccccagg tagaactgct gctgctgtgg ctttttcttac ttttatatta gataaatgga  1920
tcccgcagac tcatttcagc aggggatacg ttttggattt catagccaca gcattgtgga   1980
gaacatggaa ggttcgcaag atgaggacaa tcttaggtta ctggccagtg cagccttggg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt aagtttaat    2280 gagtcgcaga cgtcctgaaa ccatttggtg gcatgaggtt cagaaagagg aagggatga    2340 agtttctgta ttgcaggaga atattcact ggaacaggtg aaaacatgtt ggttggagcc    2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata tcaagacaa ggcagttatt agatgctgca tgatggatat    2580
gtggcctggg gtagtcggta tggaagcagt aacttttgta aatgttaagt ttaggggaga   2640
tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca   2880
ctgcgcttct acagatactg gatgttttat tttgattaag ggaaatgcca gcgtaaagca   2940
taacatgatt tgcggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgccttttc   3180
cagaatgagc ctaacaggaa ttttttgacat gaacatgcaa atctggaaga tcctgaggta  3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gttttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
```

```
gcagctgcag ctgccgccgc cgcttctgtt gccgctaaca ctgtgcttgg aatgggttac    3720
tatggaagca tcatggctaa ttccacttcc tctaataacc cttctaccct gactcaggac    3780
aagttacttg tccttttggc ccagctggag gctttgaccc aacgtctggg tgaactttct    3840
cagcaggtgg tcgagttgcg agtacaaact gagtctgctg tcggcacggc aaagtctaaa    3900
taaaaaaatc ccagaatcaa tgaataaata acaagcttg ttgttgattt aaaatcaagt     3960 gttttattt cattttcgc gcacggtatg ccctagacca ccgatctcta tcattgagaa      4020
ctcggtggat tttttccagg atcctataga ggtgggattg aatgtttaga tacatgggca    4080
ttaggccgtc tttggggtgg agatagctcc attgaaggga ttcatgctcc ggggtagtgt    4140
tgtaaatcac ccagtcataa caaggtcgca gtgcatggtg ttgcacaata tcttttagaa    4200
gtaggctgat tgccacagat aagcccttgg tgtaggtgtt tacaaaccgg ttgagctggg    4260
atgggtgcat tcggggtgaa attatgtgca ttttggattg gattttttaag ttggcaatat   4320 tgccgccaag atcccgtctt gggttcatgt tatgaaggac caccaagacg tgtatccgg     4380 tacatttagg aaatttatcg tgcagcttgg atggaaaagc gtggaaaaat tggagacac     4440 ccttgtgtcc tccaagattt tccatgcact catccatgat aatagcaatg gggccgtggg    4500
cagcggcgcg ggcaaacacg ttccgtgggt ctgacacatc atagttatgt tcctgagtta    4560
aatcatcata agccatttta atgaatttgg ggcgagagt accagattgg ggtatgaatg     4620
ttccttcggg ccccggagca tagttcccct cacagatttg catttcccaa gctttcagtt    4680
ccgagggtgg aatcatgtcc acctgggggg ctatgaaaaa caccgtttct ggggcggggg    4740
tgattaattg tgatgatagc aaatttctga gcaattgaga tttgccacat ccggtggggc    4800
cataaatgat tccgattacg ggttgcaggt ggtagtttag ggaacggcaa ctgccgtctt    4860
ctcgaagcaa gggggccacc tcgttcatca tttcccttac atgcatattt tcccgcacca   4920
aatccattag gaggcgctct cctcctagtg atagaagttc ttgtagtgag gaaaagtttt    4980
tcagcggttt cagaccgtca gccatgggca ttttggagag agtttgctgc aaaagttcta    5040
gtctgttcca cagttcagtg atgtgttcta tggcatctcg atccagcaga cctcctcgtt    5100
tcgcgggttt ggacggctcc tggaataggg tatgagacga tgggcgtcca gcgctgccag    5160
ggttcggtcc ttccagggtc tcagtgttcg agtcagggtt gtttccgtca cagtgaaggg    5220
gtgtgcgcct gcttgggcgc ttgccagggt gcgcttcaga ctcatcctgc tggtcgaaaa    5280
cttctgtcgc ttggcgccct gtatgtcggc caagtagcag tttaccatga gttcgtagtt    5340
gagcgcctcg gctgcgtggc ctttggcgcg gagcttacct ttggaagttt tcttgcatac    5400
cgggcagtat aggcatttca gcgcatacaa cttgggcgca aggaaaacgg attctgggga    5460
gtatgcatct gcgccgcagg aggcgcaaac agtttcacat tccaccagcc aggttaaatc    5520
cggttcattg gggtcaaaaa caagtttttcc gccatatttt ttgatgcgtt tcttaccttt   5580
ggtctccatg agttcgtgtc ctcgttgagt gacaaacagg ctgtccgtgt ccccgtagac    5640
tgattttaca ggcctcttct ccagtggagt gcctcggtct tcttcgtaca ggaactctga    5700
ccactctgat acaaaggcgc gcgtccaggc cagcacaaag gaggctatgt gggagggta    5760 gcgatcgttg tcaaccaggg ggtccacctt ttccaaagta tgcaaacaca tgtcaccctc    5820
ttcaacatcc aggaatgtga ttggcttgta ggtgtatttc acgtgacctg ggtccccgc    5880 tgggggggta taaaaggggg cggttctttg ctcttcctca ctgtcttccg gatcgctgtc    5940
caggaacgtc agctgttggg gtaggtattc cctctcgaag gcgggcatga cctctgcact    6000
caggttgtca gtttctaaga acgaggagga tttgatattg acagtgccgg ttgagatgcc    6060
```

```
tttcatgagg ttttcgtcca tctggtcaga aaacacaatt tttttattgt caagtttggt    6120
ggcaaatgat ccatacaggg cgttggataa aagtttggca atggatcgca tggtttggtt    6180
cttttccttg tccgcgcgct ctttggcggc gatgttgagt tggacatact cgcgtgccag    6240
gcacttccat tcggggaaga tagttgttaa ttcatctggc acgattctca cttgccaccc    6300
tcgattatgc aaggtaatta aatccacact ggtggccacc tcgcctcgaa ggggttcatt    6360
ggtccaacag agcctacctc ctttcctaga acagaaaggg ggaagtgggt ctagcataag    6420
ttcatcggga gggtctgcat ccatggtaaa gattcccgga agtaaatcct tatcaaaata    6480
gctgatggga gtggggtcat ctaaggccat ttgccattct cgagctgcca gtgcgcgctc    6540
atatgggtta aggggactgc cccatggcat gggatgggtg agtgcagagg catacatgcc    6600
acagatgtca tagacgtaga tgggatcctc aaagatgcct atgtaggttg atagcatcg    6660
ccccctctg atacttgctc gcacatagtc atatagttca tgtgatggcg ctagcagccc    6720
cggacccaag ttggtgcgat tgggtttttc tgttctgtag acgatctggc gaaagatggc    6780
gtgagaattg aagagatgg tgggtctttg aaaaatgttg aaatgggcat gaggtagacc    6840
tacagagtct ctgacaaagt gggcataaga ttcttgaagc ttggttacca gttcggcggt    6900
gacaagtacg tctagggcgc agtagtcaag tgtttcttga atgatgtcat aacctggttg    6960
gttttctttt tcccacagtt cgcggttgag aaggtattct tcgcgatcct tccagtactc    7020
ttctagcgga aacccgtctt tgtctgcacg gtaagatcct agcatgtaga actgattaac    7080
tgccttgtaa gggcagcagc ccttctctac gggtagagag tatgcttgag cagcttttcg    7140
tagcgaagcg tgagtaaggg caaaggtgtc tctgaccatg actttgagga attggtattt    7200
gaagtcgatg tcgtcacagg ctccctgttc ccagagttgg aagtctaccc gtttcttgta    7260
ggcggggttg ggcaaagcga agtaacatc attgaagaga atcttgccgg ccctgggcat    7320
gaaattgcga gtgatgcgaa aaggctgtgg tacttccgct cggttattga taacctgggc    7380
agctaggacg atctcgtcga aaccgttgat gttgtgtcct acgatgtata attctatgaa    7440
acgcggcgtg cctctgacgt gaggtagctt actgagctca tcaaaggtta ggtctgtggg    7500
gtcagataag gcgtagtgtt cgagagccca ttcgtgcagg tgaggattcg ctttaaggaa    7560
ggaggaccag aggtccactg ccagtgctgt ttgtaactgg tcccggtact gacgaaaatg    7620
ccgtccgact gccatttttt ctggggtgac gcaatagaag gtttgggggt cctgccgcca    7680
gcgatcccac ttgagtttta tggcgaggtc ataggcgatg ttgacgagcc gctggtctcc    7740
agagagtttc atgaccagca tgaagggat tagctgcttg ccaaaggacc ccatccaggt    7800
gtaggtttcc acatcgtagg tgagaaagag cctttctgtg cgaggatgag agccaatcgg    7860
gaagaactgg atctcctgcc accagttgga ggaatggctg ttgatgtgat ggaagtagaa    7920
ctccctgcga cgcgccgagc attcatgctt gtgcttgtac agacggccgc agtagtcgca    7980
gcgttgcacg ggttgtatct cgtgaatgag ttgtacctgg cttcccttga cgagaaattt    8040
cagtgggaag ccgaggcctg gcgattgtat ctcgtgcttt actatgttgt ctgcatcggc    8100
ctgttcatct tctgtctcga tggtggtcat gctgacgagc cctcgcggga ggcaagtcca    8160
gacctcggcg cggcagggc ggagctcgag gacgagagcg cgcaggctgg agctgtccag    8220
ggtcctgaga cgctgcggac tcaggttagt aggcagtgtc aggagattaa cttgcatgat    8280
cttttggagg gcgtgcggga ggttcagata gtacttgatc tcaacgggtc cgttggtgga    8340
gatgtcgatg gcttgcaggg ttccgtgtcc cttgggcgct accaccgtgc ccttgttttt    8400
catttggac ggcggtggct ctgttgcttc ttgcatgttt agaagcggtg tcgagggcgc    8460
```

```
gcaccgggcg gcaggggcgg ctcgggaccc ggcggcatgg ctggcagtgg tacgtcggcg    8520
ccgcgcgcgg gtaggttctg gtactgcgcc ctgagaagac tcgcatgcgc gacgacgcgg    8580
cggttgacat cctggatctg acgcctctgg gtgaaagcta ccggcccgt gagcttgaac     8640 ctgaaagaga gttcaacaga atcaatctcg gtatcgttga cggcggcttg cctaaggatt    8700
tcttgcacgt caccagagtt gtcctggtag gcgatctccg ccatgaactg ctcgatctct    8760
tcctcttgaa gatctccgcg gcccgctctc tcgacggtgg ccgcgaggtc gttggagatg    8820
cgcccaatga gttgagagaa tgcattcatg cccgcctcgt tccagacgcg gctgtagacc    8880
acggccccca cgggatctct cgcgcgcatg accacctggg cgaggttgag ctccacgtgg    8940
cgggtgaaga ccgcatagtt gcataggcgc tggaaaaggt agttgagtgt ggtggcgatg    9000
tgctcggtga cgaagaaata catgatccat cgtctcagcg gcatctcgct gacatcgccc    9060
agagcttcca agcgctccat ggcctcgtag aagtccacgg caaaattaaa aaactgggag    9120
tttcgcgcgg acacggtcaa ctcctcttcc agaagacgga taagttcggc gatggtggtg    9180
cgcacctcgc gctcgaaagc ccctgggatt tcttcctcaa tctcttcttc ttccactaac    9240
atctcttcct cttcaggtgg ggctgcagga ggaggggaa cgcggcgacg ccggcggcgc     9300
acgggcagac ggtcgatgaa tctttcaatg acctctccgc ggcggcggcg catggtttca    9360
gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540
aacctttcga cgaaagcgtc taaccagtca cagtcacaag gtaggctgag tacggcttct    9600
tgtgggcggg ggtggttatg tgttcggtct gggtcttctg tttcttcttc atctcgggaa    9660
ggtgagacga tgctgctggt gatgaaatta agtaggcag ttctaagacg gcggatggtg     9720
gcgaggagca ccaggtcttt gggtccggct tgctggatac gcaggcgatt ggccattccc    9780
caagcattat cctgacatct agcaagatct ttgtagtagt cttgcatgag ccgttctacg    9840
ggcacttctt cctcacccgt tctgccatgc atacgtgtga gtccaaatcc gcgcattggt    9900
tgtaccagtg ccaagtcagc tacgactctt tcggcgagga tggcttgctg tacttgggta    9960
agggtggctt gaaagtcatc aaaatccaca aagcggtggt aagctcctgt attaatggtg   10020
taagcacagt tggccatgac tgaccagtta actgtctggt gaccagggcg cacgagctcg   10080
gtgtatttaa ggcgcgaata ggcgcgggtg tcaaagatgt aatcgttgca ggtgcgcacc   10140
agatactggt accctataag aaaatgcggc ggtggttggc ggtagagagg ccatcgttct   10200
gtagctggag cgccaggggc gaggtcttcc aacataaggc ggtgatagcc gtagatgtac   10260
ctggacatcc aggtgattcc tgcggcggta gtagaagccc gaggaaactc gcgtacgcgg   10320
ttccaaatgt tgcgtagcgg catgaagtag ttcattgtag gcacggtttg accagtgagg   10380
cgcgcgcagt cattgatgct ctatagacac ggagaaaatg aaagcgttca gcgactcgac   10440
tccgtagcct ggaggaacgt gaacgggttg ggtcgcggtg taccccggtt cgagacttgt   10500
actcgagccg gccggagccg cggctaacgt ggtattggca ctcccgtctc gacccagcct   10560
acaaaaatcc aggatacgga atcgagtcgt tttgctggtt ccgaatggca agggaagtga   10620
gtcctatttt ttttttttgc cgctcagatg catcccgtgc tgcgacagat gcgccccaa    10680 caacagcccc cctcgcagca gcagcagcag caatcacaaa aggctgtccc tgcaactact   10740
gcaactgccg ccgtgagcgg tgcgggacag cccgcctatg atctggactt ggaagagggc   10800
gaaggactgg cacgtctagg tgcgccttca cccgagcggc atccgcgagt tcaactgaaa   10860
```

```
aaagattctc gcgaggcgta tgtgccccaa cagaacctat ttagagacag aagcggcgag    10920
gagccggagg agatgcgagc ttcccgcttt aacgcgggtc gtgagctgcg tcacggtttg    10980
gaccgaagac gagtgttgcg ggacgaggat ttcgaagttg atgaaatgac agggatcagt    11040
cctgccaggg cacacgtggc tgcagccaac cttgtatcgg cttacgagca gacagtaaag    11100
gaagagcgta acttccaaaa gtctttaat aatcatgtgc gaaccctgat tgcccgcgaa     11160
gaagttaccc ttggtttgat gcatttgtgg gatttgatgg aagctatcat tcagaaccct    11220
actagcaaac ctctgaccgc ccagctgttt ctggtggtgc aacacagcag agacaatgag    11280
gctttcagag aggcgctgct gaacatcacc gaacccgagg ggagatggtt gtatgatctt    11340
atcaacattc tacagagtat catagtgcag gagcggagcc tgggcctggc cgagaaggtg    11400
gctgccatca attactcggt tttgagcttg ggaaaatatt acgctcgcaa aatctacaag    11460
actccatacg ttcccataga caaggaggtg aagatagatg ggttctacat gcgcatgacg    11520
ctcaaggtct tgaccctgag cgatgatctt ggggtgtatc gcaatgacag aatgcatcgc    11580
gcggttagcg ccagcaggag gcgcgagtta agcgacaggg aactgatgca cagtttgcaa    11640
agagctctga ctggagctgg aaccgagggt gagaattact tcgacatggg agctgacttg    11700
cagtggcagc ctagtcgcag ggctctgagc gccgcgacgg caggatgtga gcttccttac    11760
atagaagagg cggatgaagg cgaggaggaa gagggcgagt acttggaaga ctgatggcac    11820
aacccgtgtt ttttgctaga tggaacagca agcaccggat cccgcaatgc gggcggcgct    11880
gcagagccag ccgtccggca ttaactcctc ggacgattgg acccaggcca tgcaacgtat    11940
catggcgttg acgactcgca accccgaagc ctttagacag caaccccagg ccaaccgtct    12000
atcggccatc atgaagctg tagtgccttc ccgctctaat cccactcatg agaaggtcct     12060
ggccatcgtg aacgcgttgg tggagaacaa agctattcgt ccagatgagg ccggactggt    12120
atacaacgct ctcttagaac gcgtggctcg ctacaacagt agcaatgtgc aaaccaattt    12180
ggaccgtatg ataacagatg tacgcgaagc cgtgtctcag cgcgaaaggt tccagcgtga    12240
tgccaacctg ggtcgctgg tggcgttaaa tgctttcttg agtactcagc ctgctaatgt     12300
gccgcgtggt caacaggatt atactaactt tttaagtgct ttgagactga tggtatcaga    12360
agtacctcag agcgaagtgt atcagtccgg tcctgattac ttctttcaga ctagcagaca    12420
gggcttgcag acggtaaatc tgagccaagc ttttaaaaac cttaaaggtt tgtggggagt    12480
gcatgccccg gtaggagaaa gagcaaccgt gtctagcttg ttaactccga actcccgcct    12540
attattactg ttggtagctc cttttcaccga cagcggtagc atcgaccgta attcctatt     12600 gggttaccta ctaaacctgt atcgcgaagc catagggcaa agtcaggtgg acgagcagac    12660
ctatcaagaa attcccaag tcagtcgcgc tttgggacag gaagacactg gcagtttgga     12720
agccactctg aacttcttgc ttaccaatcg gtctcaaaag atccctcctc aatatgctct    12780
tactgcggag gaggagcgga tcctcagata cgtgcaacag agcgttggac tgttcctgat    12840
gcaggagggg gcgacaccta ccgccgcgct ggacatgaca gctcgaaaca tggagcccag    12900
catgtatgct agtaacaggc ctttcattaa caaactgctg gactacctgc acagggcggc    12960
cgccatgaac tctgattatt tcaccaatgc tatcctgaac ccacactggc tgcccccacc    13020
tggtttctac actggcgagt acgacatgcc cgaccccaat gacgggttcc tgtgggacga    13080
tgtggacagc agcatatttt ccccgcctcc cggttataca gtttggaaga aggaagggg     13140 cgatagaaga cactcttccg tgtcgctatc cggaacggct ggtgctgccg cgaccgtgcc    13200
cgaagctgca agtcctttcc ctagcttgcc ctttcacta aacagcgttc gcagcagtga      13260
```

```
actggggaga ataacccgcc cgcgcttgat gggcgaggat gagtacttga atgactcttt    13320
gctgaggcca gagagggaaa agaacttccc caacaatgga atagagagtc tggtggataa    13380
gatgagtaga tggaagacct atgcgcagga tcacagagac gagcccagga tcttgggggc    13440
tacaagcaga ccgatccgta gacgccagcg ccacgacagg cagatgggtc ttgtgtggga    13500
cgatgaggac tctgccgatg atagcagcgt gttggacttg ggtggaagag gaggggcaa    13560 cccgttcgct catctgcgtc ccagattcgg gcgcatgttg taaaagtgaa agtaaaataa    13620
aaaggcaact caccaaggcc atggcgaccg agcgtgcgtt cgttcttttt tgttatctgt    13680
gtctagtacg atgaggagac gagccgtgct aggcggagcg gtggtgtatc cggagggtcc    13740
tcctccttct tacgagagcg tgatgcagca acaggcggcg atgatacagc ccccactgga    13800
ggctcccttc gtaccccac ggtacctggc gcctacggaa gggagaaaca gcattcgtta    13860
ctcggagctg tcgcccctgt acgataccac caagttgtat ctggtggaca acaagtcggc    13920
ggacatcgcc tccctgaact atcagaacga ccacagcaac ttcctgacca cggtggtgca    13980
gaacaatgac tttacccca cggaggctag cacccagacc atcaactttg acgagcggtc    14040
gcgatggggc ggtcagctga agaccatcat gcacaccaac atgcccaacg tgaacgagta    14100
catgttcagc aacaagttca aggcgagggt gatggtgtcc agaaaagctc ctgaaggtgt    14160
tacagtaaat gacacctatg atcataaaga ggatatcttg aagtatgagt ggtttgagtt    14220
cattttacca gaaggcaact tttcagccac catgacgatc gacctgatga acaatgccat    14280
cattgacaac tacctggaaa ttggcagaca gaatggagtg ctggaaagtg acattggtgt    14340
taagtttgac actagaaatt tcaggctcgg gtgggacccc gaaactaagt tgattatgcc    14400
aggtgtctac acttatgagg cattccatcc tgacattgta ttgctgcctg gttgcggggt    14460
agactttact gaaagccgac ttagcaactt gcttggcatc aggaagagac atccattcca    14520
ggagggtttc aaaatcatgt atgaagatct tgaagggggt aatattcctg ccctttttgga    14580 tgtcactgcc tatgaggaaa gcaaaaagga taccactact gaaacaacca cactggctgt    14640
tgcagaggaa actagtgaag atgatgatat aactagagga gatacctata taactgaaaa    14700
acaaaaacgt gaagctgcag ctgctgaagt taaaaaagag ttaaagatcc aacctctaga    14760
aaaagacagc aagagtagaa gctacaatgt cttggaagac aaaatcaaca cagcctaccg    14820
cagttggtac ctgtcctaca attacggtaa ccctgagaaa ggaataaggt cttggacact    14880
gctcaccact tcagatgtca cctgtggggc agagcaggtc tactggtcgc tccctgacat    14940
gatgcaagac ccagtcacct tccgctccac aagacaagtc aacaactacc cagtggtggg    15000
tgcagagctt atgcccgtct tctcaaagag tttctacaat gagcaagccg tgtactctca    15060
gcagctccga caggccactt cgctcacgca cgtcttcaac cgcttccctg agaaccagat    15120
cctcatccgc ccgccggcgc ccacaattac caccgtcagt gaaaacgttc ctgctctcac    15180
agatcacggg accctgccgt tacgcagcag tatccgggga gtccagcgcg tgaccgttac    15240
tgacgccaga cgccgcacct gtccctacgt ttacaaggcc ctgggcatag tcgcgccgcg    15300
cgttctttca agccgcactt tctaaaaaaa aaaaaatgt ccattctcat ctcgcccagt    15360
aataataccg gttggggact gtatgcgccc accaagatgt atggaggcgc ccgcaagcgc    15420
tctacccagc atcctgtgcg cgttcgcggt catttccgcg ctccctgggg cgcactcaag    15480
ggtcgtaccc gcactcggac cacggtcgat gatgtgatcg accaggtggt cgccgatgct    15540
cgtaattata ctcctactgc gcctacatct actgtggatg cagttattga cagtgtggtg    15600
gcagacgccc gcgcctatgc tcgccggaag agccgaagga ggcgcatcgc caggcgccac    15660
```

```
agggctactc ccgccatgcg agccgcaaaa gctattctgc ggagggccaa acgtgtgggg    15720
cgaagagcca tgcttagagc ggccagacgc gcggcttcag gtgccagcag cggcaggtcc    15780
cgcaggcgcg cggccacggc ggcagcagcg gccattgcca acatggccca accgcgaaga    15840
ggcaatgtgt actgggtgcg tgatgccact accggccagc gcgtgcccgt gcgcacccgc    15900
cccctcgca cttagaagat actgagcagt ctccgatgtt gtgtcccagc ggcaagtatg     15960
tccaagcgca aatacaagga agagatgctc caggtcatcg cgcctgaaat ctacggtccg    16020
ccggtgaagg atgaaaaaaa gccccgcaaa atcaagcggg tcaaaaataa caaaaaggaa    16080
gaagatgacg atgatgggct ggtggagttt gtgcgcgagt tcgccccaag acggcgcgtg    16140
cagtggcgcg ggcgcaaagt gcgtcaagtg ctcagacccg ggaccactgt ggttttaca    16200
cctggcgagc gttccagcac tacttttaaa cggtcctatg atgaggtgta cggggatgac    16260
gatattcttg agcaggcggc agaccgcctt gacgagtttg cttatggcaa gcgcactaga    16320
tccagtccca aagaggaggc tgtgtccatt cctttggatc atggaaatcc caccccagc    16380
ctcaaaccag tcaccctgca gcaagtgctg cccgtgcctg cgcggagagg cgtaaagcgc    16440
gagggtgagg acctatatcc caccatgcag ctaatggtgc ccaagcgcca gaggctagaa    16500
gacgtactgg agaaaatgaa agtggatgcc gatatccagc ctgaggtcaa agtaagacct    16560
atcaaggaag tggcgccagg tttgggagta caaaccttcg acatcaagat tcccaccgag    16620
tccatggaag tgcagaccga acctgcaaaa cccaccacct caattgaggt gcaaacggaa    16680
ccctggatgc ccgcgcccgt tgccgccccc agcaccactc gaagatcacg acgaaagtac    16740
ggcccagcaa gtctgctaat gcccaactat gctctgcacc catccatcat tcccactccg    16800
ggttacagag gcactcgcta ctatcgaaac cggagcaaca cctctcgccg ccgcaaacca    16860
cctgcaagtc gcactcgccg tcgccgccgc cgcaacactg ccagcaaatt gactcccgcc    16920
gccctggtgc ggagagtgta ccgcgatggt gcgctgaac ctctgacgct gccgcgcgcg     16980
cgctaccatc caagcatcac cacttaatga ctgttgacgc tgcctccttg cagatatggc    17040
cctcacttgc cgccttcgcg tccccattac tggctaccga ggaagaaact cgcgccgtag    17100
aaggatgttg gggcgaggga tgcgccgcca cagacgaagg cgcgctatca gcagacgatt    17160
aggggggtggc ttttgccag ctcttatacc catcatcgcc gcagcgatcg gggcgatacc    17220
aggcatagct tcagtggcgg ttcaggcctc gcagcgccac taacattgga aaaaacttat    17280
aaataaaaaa tagaatggac tctgacgctc ctggtcctgt gactatgttt ttgtagagat    17340
ggaagacatc aattttcat ccctggctcc gcgacacggc acgaggccgt acatgggcac     17400
ctggagcgac atcggcacga gccaactgaa cgggggcgcc ttcaattgga gcagtatctg    17460
gagcgggctt aaaaattttg gctcgaccgt aaaaacctat gggaacaaag cttggaacag    17520
cagcacaggg caggctctga gaaataagct taaggaacaa aacttccaac agaaggtggt    17580
cgatgggatc gcctctggta ttaacggcgt agtggatctg gccaaccagg ctgtacaaaa    17640
acagataaac agccgcctgg acccgccgcc cgcaacccct ggtgaaatgg aagtggagga    17700
agaacttcct ccgctggaaa agcggggcga caagcgtccg cgacccgagc tagagcagac    17760
gctggtgacg cgcgcagacg agccccttc atatgaggag gcagtaaagc tcggaatgcc    17820
cactaccagg cctgtagctc acatggctac cggggtgatg aaaccttctc agtcacatcg    17880
acccgccacc ttggacttgc ctcctccccc tgcttctgcg gcgcctgttc ccaaacctgt    17940
cgctaccaga aagcccaccg ccgtacagcc cgtcgccgta ccagaccgc gtcctggggg     18000
cacaccgcgc ccgaaagcaa actggcaaag tactctgaac agcatcgtgg gtctgggcgt    18060
```

```
gcagagtgta aagcgccgtc gctgctatta attaaatatg gagtagcgct taacttgctt   18120
gtctgtgtgt atgtatcatc accacgccgc cgcagcagag gagaaaggaa gaggtcgcgc   18180
gccgaggctg agttgctttc aagatggcca ccccatcgat gatgcccaa tgggcataca    18240 tgcacatcgc cggacaggat gcttcggagt acctcagtcc gggtctggtg cagttcgccc   18300
gtgcaacaga cacctacttc agtatgggga acaaatttag aaaccccaca gtggcgccca   18360
cccacgatgt gaccaccgac cgtagccagc gcctgatgct gcgcttcgtg cccgttgacc   18420
gggaagacaa tacctactct tacaaagttc gctacacgct ggctgtaggc gacaacagag   18480
tgcttgacat ggccagcaca ttctttgaca ttcgggggt gcttgataga ggtcctagct     18540
tcaagccata ttccggcaca gcttacaatt cactcgctcc taagggcgcg cccaatacat   18600
ctcagtggat agttacaaca aatggggaca atgcagtaac taccaccaca aacacatttg   18660
gcattgcttc catgaaggga gacaatatta ctaaagaagg tttgcaaatt gggaaagaca   18720
ttaccactac tgaaggagaa gaaaagccca tttatgccga taaacatat cagccagagc     18780 ctcaagttgg agaagaatca tggactgata ctgatggaac aaatgaaaag tttggtggaa   18840
gagcccttaa accagctacc aacatgaagc catgctacgg gtcttttgca agacctacaa    18900
acataaaagg gggccaagct aaaaacagaa agtaaaacc aacaaccgaa ggaggggttg     18960
aaactgagga accagatatt gatatggaat ttttcgatgg tagagatgct gttgcaggag    19020
ctttagcgcc tgaaattgtg ctttatacgg aaaatgtaaa tttggaaact ccagacagtc   19080
atgtggtata taaccagaa acgtctaata actctcatgc aaatttgggt caacaagcca    19140
tgcctaacag acccaattac attggcttca gggataactt cgtaggccta atgtactaca   19200
acagtactgg aaatatggga gttttggctg gccaagcatc acaactgaat gcagtggttg   19260
acttgcagga cagaaatact gaactgtcat atcagctttt gcttgattct ctgggagaca   19320
gaaccagata cttcagcatg tggaatcagg ctgtggacag ttacgatccc gatgttcgca   19380
ttattgaaaa tcatggcatc gaggatgaac tgcctaatta ctgttttcct ctgaatggca   19440
taggaccagg gcacacatat caaggcatta agttaaaac cgatgacact aatggatggg    19500
aaaaagatgc taatgttgct ccagctaatg aaataaccat aggcaacaac ctggctatgg    19560
aaattaatat ccaagctaac cttttggagaa gttttctgta ctctaatgtg gcttgtacc    19620 ttccagatgt ttacaagtac acgccaccta acattacttt gcccactaac accaacacct   19680
atgagtacat gaacgggcga gtggtatccc catccctggt tgattcatac atcaacattg    19740
gcgccaggtg gtctcttgac ccaatggaca atgtgaatcc attcaaccac caccgcaatg   19800
ctggtctgcg ctacaggtcc atgcttctgg gaaatggtcg ttatgtgcct ttccacatac    19860
aagtgcctca gaaattcttt gctgtcaaga acctacttct tctacctggc tcctacacct    19920
acgagtggaa cttccgaaag gatgtgaaca tggtcctgca aagttccctt ggaaatgacc   19980
tcagaacgga tggtgctacc ataagtttca ccagcatcaa tctctatgcc accttcttcc   20040
ccatggctca caacacagct tccacccttg aagccatgct gcgcaacgat accaatgatc   20100 agtcattta cgactacctc tctgcagcta acatgcttta ccccattcct gccaatgcaa     20160
ccaacattcc aatttccatc ccatctcgca actgggcagc cttcaggggc tggtccttca   20220
ccagactcaa aaccaaggag actccatctc ttggatcagg gttcgatccc tacttcgtat   20280
attctggatc tattccctac ctggatggca ccttttacct taaccacact ttcaagaagg   20340
tctccatcat gtttgactcc tcagtcagct ggcctggcaa tgacaggctg ttgagtccaa    20400
atgagtttga aatcaagcgc actgtggacg gggaaggata caacgtggca caatgcaaca   20460
```

```
tgaccaaaga ctggttcctg gttcagatgc ttgccaatta caacattggc taccagggct    20520
tttacatccc tgagggatac aaggatcgca tgtactcctt tttcagaaac ttccagccta    20580
tgagcaggca ggtggttgat gaggttaatt acactgacta caaagccgtc accttaccat    20640
accaacacaa caactctggc tttgtagggt accttgcacc tactatgaga caaggggaac    20700
cttacccagc caattatcca tacccgctca tcggaactac tgccgttaag agtgtcaccc    20760
agaaaaagtt cctgtgcgac aggaccatgt ggcgcattcc cttctccagc aacttcatgt    20820 ccatggggc ccttaccgac ctgggacaga acatgctcta tgccaactca gcccatgcgc    20880
tggacatgac ttttgaggtg gatcccatgg atgagcccac cctgctttat cttcttttcg    20940
aagtcttcga cgtggtcaga gtgcaccagc cacaccgcgg cgtcatcgag gccgtctacc    21000
tgcgcacacc gttctcggcc ggcaacgcca ccacataaga agcctcttgc ttcttgcaag    21060
cagcagctgc agccatgaca tgcgggtccg gaaacggctc cagcgagcaa gagctcaaag    21120
ccatcgtccg agacctgggc tgcggaccct atttcctggg aacctttgac aagcgtttcc    21180
cggggttcat ggcccccgac aagctcgcct gcgccatagt caacactgcc ggacgcgaga    21240
cggggggaga gcactggctg gcttttggtt ggaacccgcg ctacaacacc tgctacccttt    21300 ttgatccttt tggggttctcg gatgagcggc tcaaacagat ttaccagtttt gagtacgagg    21360 ggctcctgcg tcgcagtgcc cttgctacca agaccgctg catcaccctg gagaagtcta    21420
cccaaagcgt gcagggtccg cgctcagccg cctgtggact tttttgctgt atgttccttc    21480
atgcctttgt gcactggccc gaccgcccca tggacgaaaa ccccaccatg aagttgctga    21540
ctggggtgtc caacagcatg ctccaatcac cccaagtcca gcccacctg cgccgcaacc    21600 aggaggtgct ataccgcttc ctaaacaccc actcatctta ctttcgttct caccgcgcgc    21660
gcattgaaag ggccaccgcg tttgaccgta tggatatgca ataagtcatg taaaaccgtg    21720
ttcaataaac agcactttat ttttacatgc actgaggctc tggttttgct catttgtttc    21780
atcatttact cagaagtcga atgggttctg gcgggagtca gagtgacccg cgggcaggga    21840
tacgttgcgg aactgtaacc tgttctgcca cttgaactcg gggattacca gcttgggaac    21900
tggaatctcg ggaaaggtgt cttgccacaa cttttctggtc agttgcatag cgccaagcag    21960
gtcaggagca gagatcttga aatcacagtt ggggccggca ttctggacac gggagttgcg    22020
atacactggg ttgcaacact ggaacactat caacgctggg tgtcttacgc ttgccaacac    22080
ggttgggtca ctgatggtag tcacatccaa gtcttcagca ttggccatcc caaaggggt    22140 catcttacat gtctgcctgc ccatcacggg agcgcagcct ggcttgtggt tgcaatcaca    22200
atgaatgggg atcagcatca tcctggcttg gtcgggagtt atccctgggt acacagcctt    22260
catgaaggct tcgtactgct taaaagcttc ctgggcctta cttccctcgg tgtagaacat    22320
cccacaggac ttgctggaaa attgattagt agtacagttg gcatcattca cacaacagcg    22380
ggcatcgttg ttgccaact gaaccacatt tctgccccag cggttttggg tgatcttggc    22440
tctgtctgga ttctccttca tagcgcgctg cccgttctcg ctcgccacat ccatctcgat    22500
aatgtggtcc ttctggatca tgatagtgcc atgcaggcat ttcaccttgc cttcataatc    22560
ggtgcatcca tgagcccaca gagcgcaccc ggtgcactcc caattattgt gggcgatctc    22620
agaataataa tgtaccaatc cctgcatgaa tcttcccatc attgttgtca aggtcttcat    22680
gctggtaaat gtcagcggga tgccacggtg ctcctcgttc acatactggt ggcagatacg    22740
cttgtattgc tcgtgctgct ctggcatcag cttgaaagag gttctcagat cattatccag    22800
cctgtacctt tccattagca cagccatcac ttccatgccc ttctcccagg cagataccag    22860
```

```
gggcagactc aaaggattcc taacagcaat aaaagtagct cctttagcta tagggtcatt   22920
cttgtcgatc ttctcaacac ttctcttgcc atccttctca atgatgcgca ccggggggta   22980
gctgaagccc acggccacca actgagcctg ttctcttttct tcttcactat cctggctgat   23040
gtcttgcaga gggacatgct tggtcttcct gggcttcttc ttgggaggga tcggggagg    23100
actgttgctc cgctccggag acagggatga ctgcgaagtt tcgcttacca ataccacctg   23160
gctctcggta gaagaaccgg accccacacg acggtaggtg ttcctcttcg ggggcagagg   23220
tggaggcgac tgagatgggc tgcggtctgg ccttggaggc ggatggctgg cagagctcat   23280
tccgcgttcg ggggtgtgct cccggtggcg gtcgcttgac tgatttcctc cgcggctggc   23340
cattgtgttc tcctaggcag agaaacaaca gacatggaaa ctcagccatc actgccaaca   23400
tcgctgcaag caccatcaca cctcgccccc agcagcgacg aggaggagag cttaaccacc   23460
ccaccaccca gtcccgctac caccacctct accctcgatg atgaggagga ggtcgacgca   23520
gcccaggaga tgcaggcgca ggataatgtg aaaacgaag agattgaggc agatgtcgag     23580
caggacccgg gctatgtgac gccggcggag caccaggagg agctgaaacg cttctctagac  23640
agagaggatg acgaccgccc agagcatcaa gcagatggcg tttaccagga ggctgggatc   23700
agggatcatg tcgccgacta cctcaccggc cttggtgggg aggacgtgct cctcaaacat   23760
ctagcaaggc agtcgatcat agttaaagac gcattgctcg atctcactga agtgccatc    23820
agtgtggaag agcttagccg cgcctacgag ctgaacctct tttcgcctca ggtaccccc    23880
aagcggcagc caaacggcac ctgcgaggcc aaccctcgac tcaacttcta tccagctttt   23940
actatccccg aagtgttggc cacctaccac atctttttca agaaccaaaa gattccagtc   24000
tcctgccgcg ccaaccgcac ccgcgccgat gccctgctca acttgggtcc gggagctcgc   24060
ttacctgata tagcttcctt ggaagaggtt ccaaagatct ttgagggtct gggaagtgat   24120
gagacacggg ccgcaaatgc tctgcaacag ggagagaatg acatggatga acaccacagc   24180
gctctggtgg aactggaggg tgacaatgcc cggattgcag tgctcaagcg cagtatcgtg   24240
gtcacccatt ttgcctaccc cgctgttaac ctgccccccca aagttatgag cgctgtcatg   24300
gaccatctgc tcatcaaacg agcaagacct cttttcagaaa accagaacat gcaggatcca   24360
gacgcctcgg acgagggcaa gccggtagtc agtgacgagc agctatctcg ctggctgggt    24420
accaactccc cccgagattt ggaagagagg cgcaagctta tgatggctgt agtgctagta   24480
actgtggagc tggagtgtct gcgccgcttt ttcaccgacc ctgagaccct cgcaagcta    24540
gaggagaacc tgcactacac ctttagacat ggcttcgtgc ggcaggcatg caagatctcc   24600
aacgtggagc ttaccaacct ggtttcttac atgggcattt tgcatgagaa ccgactaggg   24660
cagagcgtcc tgcacaccac ccttaaaggg gaggcccgcc gtgactacat ccgagactgt   24720
gtctacctct acctctgcca tacctggcaa actggtatgg gtgtgtggca acagtgtttg   24780
gaagagcaga acctaaaaga gctggacaag ctcttgcaga gatccctcaa agccctgtgg   24840
acaggttttg atgagcgcac cgtcgcctcg gacctggcag acatcatctt ccccgagcgt   24900
ctcagggtta ctctgcgaaa cggcctgcca gactttatga ccagagcat gcttaacaac    24960
tttcgctctt tcatcctgga acgctccggt atcctgcctg ccacctgctg tgcgctgccc   25020
tccgactttg tgcctctcac ctaccgcgag tgcccaccgc cgctatgag ccactgctac     25080
ctgttccgcc tggccaacta ccctctcctac cactcggatg ttatagagga tgtgagcgga   25140
gacgcctgc tggaatgcca ctgccgctgc aatctttgca cacccacccg ctcccttgcc    25200
tgcaaccccc agttgctgag cgagacccag attatcggca ccttcgagct gcagggtccc   25260
```

```
agaagtaaag gcgaggggtc ttctccgggg cagagtttga aactgacacc ggggctgtgg   25320
acctccgcct acctgcgcaa gtttcacccc gaggactacc atccctatga gatcaggttc   25380
tatgaggacc aatcacatcc tcccaaagtc gagctctcag cctgcgtcat cacccaggga   25440
gcaattctgg cccaattgca agccatccaa aaatctcgcc aagaatttct gctaaaaaag   25500
ggaaacgggg tctaccttga ccctcagacc ggtgaggagc tcaacacaag gttccccccag  25560 gatgtcccat cgccgaggaa gcaagaagtt gaaggtgcag ctgtcgcccc cagaggatat   25620
gaaggaagac tgggacagtc aggcagagga ggagatggaa gattgggaca gccaggcaga   25680
ggaggtggac agcctggagg aagacagttt ggaggaggaa gacgaggagg cagaggaggt   25740
ggaagaagca accgccgcca aacagttgtc atcggcggcg gagacaagca agtccccaga   25800
cagcagcacg gctaccatct ccgctccggg tcgggggggcc cagcggcggc ccaacagtag  25860
atgggacgag accgggcgat tcccaaaccc gaccaccgct ccaagaccg gtaagaagga    25920 gcgacaggga tacaagtcct ggcgtggaca taaaaacgct atcatctcct gcttgcatga   25980 atgcggggc aacatatcct tcacccggcg atacctgctc ttccaccacg gtgtaaactt    26040
cccccgcaat atcttgcatt actaccgtca cctccacagc ccctactgca gtcagcaagt   26100
cccggcaacc ccgacagaaa aatacagcag cgacaacggt gaccagaaaa ccagcagtta   26160
gaaaatccac aacaagtgca ccaggaggag gactgaggat cacagcgaac gagccagcgc   26220
agaccagaga gctgaggaac cggatctttc caaccctcta tgccattttc cagcagagtc   26280
gggggcaaga gcaggaactg aaagtaaaaa accgatctct gcgctcgctc accagaagtt   26340
gtttgtatca caagagcgaa gaccaacttc agcgcactct cgaggacgcc gaggctctct   26400
tcaacaagta ctgcgcgctg actcttaaag agtagccctt gcccgcgctc attttgaaaa   26460
cggcgggaat cacgtcaccc ttggcacctg tcctttgccc ttgtcatgag taaagagatt   26520
cccacgcctt acatgtggag ctatcagccc caaatggggt tggcagcagg cgcttcccag   26580
gactactcca cccgcatgaa ttggcttagc gccgggccct caatgatatc acgggttaat   26640
gatatacgag cttatcgaaa ccagttactc ctagaacagt cagctctcac caccacaccc   26700
cgtcaacacc ttaatccccg aaattggccc gccaccctgg tgtaccagga aaatcccgct   26760
cccaccaccg tactacttcc tcgagacgcc caggccgaag ttcagatgac taacgcaggt   26820
gtacagctgg cgggcggttc cgccctatgt cgtcaccgac ctcaacagag tataaaacgc   26880
ctggtgatta gaggccgagg tatccagctc aacgacgagt cggttagctc ttcgcttggt   26940
ctgcgaccag acggagtctt ccaaatcgcc ggctgtggga gatcttcctt cactcctcgt   27000
caggctgtgc tgactttgga gagttcgtcc tcgcagcccc gctcgggcgg cattggaact   27060
ctccagtttg tggaggagtt tactccctct gtctacttca accccttctc cggctctcct   27120
ggccagtacc cggacgagtt cataccaaac ttcgacgcaa tcagcgagtc agtggatggc   27180
tatgattgat gtctaatggt ggtgcggctg agctagctcg actgcgacac ctagaccact   27240
gccgccgctt tcgctgcttc gcccgggaac tcaccgagtt catctacttc gaactctccg   27300
aggagcaccc tcagggtccg gcccacgag tgcggattac catcgaaggg ggaatagact    27360
ctcgcctgca tcgcatcttc tcccagcggc ccgtgctaat tgaacgcgac cagggaaata   27420
caaccatctc catctactgc atctgtaacc accccggatt gcatgaaagc ctttgctgtc   27480
ttgtttgtgc tgagttaat aaaaaactgag ttaagaccct cctacggact accgcttctt    27540
caatcaggac tttacaacac caaccagatc ttccagaaga cccagaccct tcctcctttc   27600
atccaggact ctaactctac cttaccagca ccctccacta ctaaccttcc cgaaacaaac   27660
```

```
aagcttgcat ctcatctgca acaccgcctt tcacgaagcc ttctttctgc caatactacc  27720
actcccaaaa ccggaggtga gctccgcggt cttcctactg acgaccctg ggtggtagcg   27780 ggttttgtaa cgttaggagt agttgcgggt gggcttgtgc tgatcctttg ctacctatac  27840
acaccttgct gtgcatattt agtcatattg tgctgttggt ttaagaaatg ggggccatac  27900
tagtcgtgct tgctttactt tcgcttttgg gtctgggctc tgctaatctc aatcctctcg  27960
atcacgatcc atgtttagac ttcgacccag aaaactgcac acttactttt gcacccgaca  28020
caagccgtct ctgtggagtt cttattaagt gcggatggga ctgcaggtcc gttgaaatta  28080
cacataataa caaaacatgg aacaatacct tatccaccac atgggagcca ggagttcccc  28140
agtggtatac tgtctctgtc cgaggtcctg acggttccat ccgcattagt aacaacactt  28200
tcattttttc tgaaatgtgc gatctggcca tgttcatgag cagacagtat gacctatggc  28260
ctcccagcaa agagaacatt gtggcatttt ccattgctta ttgcttggta acatgcatca  28320
tcactgctat catttgtgtg tgcatacact tgcttatagt tattcgccct agacaaagca  28380
atgaggaaaa agagaaaatg ccttaacctt tttcctcata cctttctttt acagcatggc  28440
ttctgttaca gctctaatta ttgccagcat tgtcactgtc gctcacgggc aaacaattgt  28500
ccatattacc ttaggacata atcacactct tgtagggccc ccaattactt cagaggttat  28560
ttggaccaaa cttggaagtg ttgattattt tgatataatt tgcaacaaaa ctaaccaat   28620 atttgtaatc tgtaacagac aaaatctcac gttaattaat gttagcaaaa tttataacgg  28680
ttactattat ggttatgaca gatccagtag tcaatataaa aattacttag ttcgcataac  28740
tcagcccaaa ttaacagtgc caactatgac aataattaaa atggctaata aagcattaga  28800
aaattttaca tcaccaacaa cacccaatga aaaaaacatt ccaaattcaa tgattgcaat  28860
tattgcggcg gtggcattgg gaatggcact aataataata tgcatgctcc tatatgcttg  28920
ttactataaa aagtttcaac ataaacagga tccactacta aattttaaca tttaattttt  28980
tatacagatg atttccacta caattttat cattactagc cttgcagctg taacttatgg    29040
ccgttcacac ctaactgtac ctgttggctc aacatgtaca ctacaaggac cccaagaagg   29100
ctatgtcact tggtggagaa tatatgataa tggagggttc gctagaccat gtgatcagcc   29160
tggtacaaaa ttttcatgca acggaagaga cttgaccatt attaacataa catcaaatga   29220
gcaaggcttc tattatggaa ccaactataa aaatagttta gattacaaca ttattgtagt   29280
gccagccacc acttctgctc cccgcaaatc cactttctct agcagcagtg ccaaagcaag   29340
cacaattcct aaaacagctt ctgctatgtt aaagcttcca aaaatcgctt taagtaattc   29400
cacagccgct cccaatacaa ttcctaaatc aacaattggc atcattactg ccgtggtagt   29460
gggattaatg attatatttt tgtgtataat gtactacgcc tgctgctata gaaaacatga   29520 acaaaaggt gatgcattac taaattttga tatttaattt tttatagaat tatgatattg    29580
tttcaatcaa ataccactac ctcctatgca tacacaaaca ttcagcctaa atacgctatg   29640
caactagaaa tcacaatact aattgtaatt ggaattctta tactatctgt tattctttat   29700
tttatattct gccgtcaaat acccaatgtt catagaaatt ctaaaagacg tcccatctat   29760
tctcctatga ttagtcgtcc ccatatggct ctgaatgaaa tctaagatct ttttttttt    29820 ctcttacagt atggtgaaca tcaatcatga tccctagaaa tttcttcttc accatactca   29880
tctgtgcttt taatgtctgt gctactttca cagcagtagc cactgcaagc ccagactgta   29940
taggaccatt tgcttcctat gcactttttg ccttcgttac ttgcatctgc gtgtgtagca   30000
tagtctgcct ggttattaat tttttccaac tggtagactg gatctttgtg cgaattgcct   30060
```

```
acctacgtca ccatcccgaa taccgcaatc aaaatgttgc ggcacttctt aggcttattt   30120
aaaaccatgc aggctatgct accagtcatt ttaattttgc tactaccctg cattcccta    30180 gcttccaccg ccactcgcgc tacacctgaa caacttagaa aatgcaaatt tcaacaacca   30240
tggtcatttc ttgattgcta ccatgaaaaa tctgattttc ccacatactg gatagtgatt   30300
gttggaataa ttaacatact ttcatgtacc tttttctcaa tcacaatata ccccacattt   30360
aattttgggt ggaattctcc caatgcactg ggttacccac aagaaccaga tgaacatatt   30420
ccactacaac acatacaaca accactagca ctggtacagt atgaaaatga gccacaacct   30480
tcactgcccc ctgccattag ttacttcaac ctaaccggcg gagatgactg acccaatcgc   30540
cacatcatcc accgctgcca aggagctgct ggacatggac ggacgtgcct cagaacagcg   30600
actcatccaa ctacgcattc gtcagcagca ggaacgagca gtaaaagagc taagggatgc   30660
cattgggatt caccagtgca aaaaaggcat attctgctta gtaaaacaat ccaaaatctc   30720
ctacgagatc accgctactg accatcgtct ctcatacgag ctcggtccgc agcgacaaaa   30780
attcacctgc atggtgggaa tcaaccccat agttatcacc cagcagtctg gagatactaa   30840
gggttgtatc cagtgttcct gtgattccac cgagtgcatc tacacactgc tgaagaccct   30900
ctgcggcctt cgagacctcc tacccatgaa ctaatcattg ccctacctt acccaatcaa    30960 aatattaata aagacactta cttgaaatca gcaatacagt ctttgtcaaa actttctacc   31020
agcagcacct caccctcttc ccaactctgg tactctaaac gtcggagggt ggcatacttt   31080
ctccacactt tgaaagggat gtcaaatttt atttcctctt ctttgcccac aatcttcatt   31140
tctttatccc cagatggcca agcgagctcg gctaagcact tccttcaacc cggtgtaccc   31200
ttatgaagat gaaagcagct cacaacaccc atttataaat cctggtttca tttcccctga   31260
cgggttcaca caaagtccaa acggggtttt aagtcttaaa tgtgttaatc cacttaccac   31320
tgcaagcggc tccctccaac ttaaagtggg aagtggtctt acagtagaca ctactgatgg   31380
atccttagaa gaaaacatca aagttaacac cccctaaca aagtcaaacc attctataaa     31440
tttaccaata ggaaacggtt tgcaaataga acaaaacaaa ctttgcagta aactcggaaa   31500
tggtcttaca tttgactctt ccaattctat tgcactgaaa aataacactt tatggacagg   31560
tccaaaacca gaagccaact gcataattga atacgggaaa caaaacccag atagcaaact   31620
aactttaatc cttgtaaaaa atggaggaat tgttaatgga tatgtaacgc taatgggagc   31680
ctcagactac gttaacacct tatttaaaaa caaaaatgtc tccattaatg tagaactata   31740
ctttgatgcc actggtcata tattaccaga ctcatcttct cttaaaacag atctagaact   31800
aaaatacaag caaaccgctg actttagtgc aagaggtttt atgccaagta ctacagcgta   31860
tccatttgtc cttcctaatg cgggaacaca taatgaaaat tatattttg gtcaatgcta    31920 ctacaaagca agcgatggtg ccctttttcc gttggaagtt actgttatgc ttaataaacg   31980
cctgccagat agtcgcacat cctatgttat gacttttta tggtccttga atgctggtct    32040
agctccagaa actactcagg caaccctcat aacctcccca tttaccttt cctatattag    32100 agaagatgac tgcaacaaa aataaagttc aacattttt attgaaattc cttttacagt     32160
attcgagtag ttattttgcc tccccttcc catttaacag aatacaccaa tctctcccca    32220
cgcacagctt taaacatttg gataccatta gagatagaca tagttttaga ttccacattc   32280
caaacagttt cagagcgagc caatctgggg tcagtaatac ataaaaatgc atcgggatag   32340
tcttttaaag cgctttcaca gtccaactgt tgcggatgcg actccggagt ctgaatcacg   32400
gtcatctgga agaagaacga tgggaatcat aatccgaaaa cggaatcggg cgattgtgtc   32460
```

```
tcatcaaacc cacaagcaac cgctgtctgc gtcgctccgt gcgactgctg tttatgggat    32520
cggggtccgc agtgtcctga agcatgattt aatagccct taacattaac tttctggtgc    32580
gatgcgcgca gcaacgcatt ctgatttcac ttagattact acagtaggta cagcacatta    32640
tcacaatatt gtttaataaa ccataattaa aagcgctcca gccaaaactc atatctgata    32700
taatcgcccc tgcatgacca tcataccaaa gtttaatata aattaaatgt cgttccctca    32760
aaaacacact acccacatac atgatctctt ttggcatgtg catattaaca atttgtctgt    32820
accatggaca acgttggtta atcatgcaac ccaatataac cttccggaac cacactgcca    32880
acaccgctcc cccagccatg cattgaagtg aaccctgctg attacaatga caatgaagaa    32940
cccaattctc tcgaccatga atcacttgag actgaaaaat atctatagta gcacaacaaa    33000
gacataaatg catgcatctt ctcataattt ttaactcctc tggatttaaa aacatatccc    33060
aaggaatggg aaactcttgc agaacagtaa agctggcaga acaaggaaga ccacgaacac    33120
aacttacact atgcatagtc atagtatcac aatctggcaa cagcgggtgg tcttcagtca    33180
tagaagctcg ggtttcattt tcctcacatc gtggtaattg ggctctggtg taagggtgat    33240
gtctggcgca tgatgtggag cgtgcgcgca accttgtcat aatggagttg cttcctgaca    33300
ttctcgtatt ttgtatagca aaacgctgcc ctggcacaac acactcttct tcgtcttcta    33360
tcctgccgct tagtgtgttc cgtctgataa ttcaagtaca gccacactct taagttggtc    33420
aaaagaatgc tggcttcagt tgtaatcaaa actccatcat atttaattgt tctaaggaaa    33480
tcatccacgg tagcatatgc aaatcccaac caagcaatgc aactggattg cgtttcaagc    33540
agcagaggag agggaagaga cggaagaatc atgttaattt ttattccaaa cgatctcgca    33600
gtacttcaaa ttgtagatcg cgcagatggc atctatcgcc cccactgtgt tggtgaaaaa    33660
gcacagctaa atcaaaagaa atgcgatttt caaggtgctc aacggtggct tccaacaaag    33720
cctccacgcg cacatccaaa aacaaaagaa taccaaaaga aggagcattt tctaactcct    33780
caaacatcat attacattcc tgcaccattc ccagataatt ttcagctttc cagccttgaa    33840
ttattcgtgt cagttcttgt ggtaaatcca aaccacacat tacaaacagg tcccggaggg    33900
cgccctccac caccattctt aaacacaccc tcataatgac aaaatatctt gctcctgtgt    33960
cacctgtagc aaattaagaa tggcatcatc aattgacatg cccttggctc taagttcttc    34020
tctaagttct agttgtagat actctctcat attatcacca aactgcttag ccagaagccc    34080
cccgggaaca atagcagggg acgctacagt gcagtacaag cgcagacctc cccaattggc    34140
tccagcaaaa acaagattag aataagcata ctgggaacca ccagtaatat catcaaagtt    34200
gctgaaaata taatcaggca gagtttcttg taaaaattga ataaaagaaa aattttccaa    34260
agaaacattc aaaaccgttg ggatgcaaat acaataggtt accgcgctgc gctccaacat    34320
tgttagtttt gaattagtct gcaaaataaa agaaacaagc gtcatatcat agtagcctgt    34380
cgaacaggtg gaaaaatcag tctttccatc acaagacaag ccacagggtc tccagctcga    34440
ccctcgtaaa acctgtcatt gtgattaaac aacagcaccg aaagttcctc gcggtggcca    34500
gcatgaataa ttcttgatga agcatacaat ccagacatgt tagcatcagt taaagagaaa    34560
aaacagccaa catagcctct gggtataatt atgcttaatt ttaagtatag caaagccacc    34620
cctcgcggat acaaagtaaa aggcacagga gaataaaaaa tataattatt tctctgctgc    34680
tgttcaggca acgttgctcc cggtccctct aaatagacat acaaagcctc atcagccatg    34740
gcttaccagg caaagtacag cgggcgcaca aagcacaagc tctaaagaag ctctaaaaac    34800
actctccaac ctctccacaa tatatacaca agccctaaac tgacgtaatg ggagtaaagt    34860
```

-continued

| | |
|---|---|
| gaaaaaaaaa taccgccaag cccaacacac accccgaaac tgcgtcagca ggaaaaagta | 34920 |
| cagtttcact tccgcattcc caacaagcgt aacttcctct ttctcatggt acgtcacatc | 34980 |
| cgattaactt gcaacgtcat tttcccacgg tcgcgccgcc ccttttagcc gttaaccccg | 35040 |
| cagccaatca ccacacagcg cgcactttt taaattacct catttacatg ttggcaccat | 35100 |
| tccatctata aggtatatta tatagataga | 35130 |

<210> SEQ ID NO 2
<211> LENGTH: 35355
<212> TYPE: DNA
<213> ORGANISM: adenovirus
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t

<400> SEQUENCE: 2

| | |
|---|---|
| tctatctata atatacct tatagatgga atggtgccaa tatgtaaatg aggtgatttt | 60 |
| aaaaagtgng gatcgtgtgg tgattggctg nggggttaac ggctaaaagg ggcggtgcga | 120 |
| ccgtgggaaa atgacgtttt gtgggggtgg agtttttttg caagttgtcg cgggaaatgt | 180 |
| gacgcataaa aaggcttttt tctcacggaa ctacttagtt ttcccacggt atttaacagg | 240 |
| aaatgaggta gttttgaccg gatgcaagtg aaaattgttg attttcgcgc gaaaactgaa | 300 |
| tgaggaagtg ttttctgaa taatgtggta tttatggcag ggtggagtat tgttcaggg | 360 |
| ccaggtagac tttgacccat tacgtggagg tttcgattac cgtgttttt acctgaatt | 420 |
| ccgcgtaccg tgtcaaagtc ttctgttttt acgtaggtgt cagctgatcg ctagggtatt | 480 |
| tatacctcag ggtttgtgtc aagaggccac tcttgagtgc cagcgagaag agttttctcc | 540 |
| tctgcgccgg cagtttaata ataaaaaaat gagagatttg cgatttctgc ctcaggaaat | 600 |
| aatctctgct gagactggaa atgaaatatt ggagcttgtg gtgcacgccc tgatgggaga | 660 |
| cgatccggag ccacctgtgc agcttttga gcctcctacg cttcaggaac tgtatgattt | 720 |
| agaggtagag ggatcggagg attctaatga ggaagctgta aatggctttt ttaccgattc | 780 |
| tatgcttta gctgctaatg aagggttaga attgatccg cctttggaca cttttgatac | 840 |
| tccaggggta attgtggaaa gcggtacagg tgtaagaaaa ttacctgatt tgagttccgt | 900 |
| ggactgtgat ttgcactgct atgaagacgg gtttcctccg agtgatgagg aggaccatga | 960 |
| aaaggagcag tccatgcaga ctgcagcggg tgagggagtg aaggctgcca atgttggttt | 1020 |
| tcagttggat tgcccggagc ttcctggaca tggctgtaag tcttgtgaat ttcacaggaa | 1080 |
| aaatactgga gtaaaggaac tgttatgttc gctttgttat atgagaacgc actgccactt | 1140 |
| tatttacagt aagtgtgttt aagttaaaat ttaaggaat atgctgtttt tcacatgtat | 1200 |
| attgagtgtg agttttgtgc ttcttattat aggtcctgtg tctgatgctg atgaatcacc | 1260 |
| atctcctgat tctactacct cacctcctga gattcaagca cctgttcctg tggacgtgcg | 1320 |
| caagcccatt cctgtgaagc ttaagcctgg gaaacgtcca gcagtggaaa aacttgagga | 1380 |
| cttgttacag ggtgggacg gacctttgga cttgagtaca cggaaacgtc caagacaata | 1440 |
| agtgttccat atccgtgttt acttaaggtg acgtcaatat ttgtgtgaca gtgcaatgta | 1500 |
| ataaaaatat gttaactgtt cactggtttt tattgcttt tgggcgggga ctcaggtata | 1560 |
| taagtagaag cagacctgtg tggttagctc ataggagctg gctttcatcc atggaggttt | 1620 |

```
gggccatttt ggaagacctt aggaagacta ggcaactgtt agagaacgct tcggacggag    1680
tctccggttt ttggagattc tggttcgcta gtgaattagc tagggtagtt tttaggataa    1740
aacaggacta taaacaagaa tttgaaaagt tgttggtaga ttgcccagga cttttttgaag   1800 ctcttaattt gggccatcag gttcactta aagaaaaagt tttatcagtt ttagacttttt   1860 caaccccagg tagaactgct gctgctgtgg cttttcttac ttttatatta gataaatgga    1920
tcccgcagac tcatttcagc aggggatacg ttttggattt catagccaca gcattgtgga    1980
gaacatggaa ggttcgcaag atgaggacaa tcttaggtta ctggccagtg cagccttttgg  2040 gtgtagcggg aatcctgagg catccaccgg tcatgccagc ggttctggag gaggaacagc    2100
aagaggacaa cccgagagcc ggcctggacc ctccagtgga ggaggcgag tagctgactt     2160 gtctcctgaa ctgcaacggg tgcttactgg atctacgtcc actggacggg ataggggcgt    2220
taagagggag agggcatcta gtggtactga tgctagatct gagttggctt aagtttaat     2280 gagtcgcaga cgtcctgaaa ccatttggtg gcatgaggtt cagaaagagg gaagggatga    2340
agtttctgta ttgcaggaga aatattcact ggaacaggtg aaaacatgtt ggttggagcc    2400
tgaggatgat tgggaggtgg ccattaaaaa ttatgccaag atagctttga ggcctgataa    2460
acagtataag attactagac ggattaatat ccggaatgct tgttacatat ctggaaatgg    2520
ggctgaggtg gtaatagata ctcaagacaa ggcagttatt agatgctgca tgatggatat    2580
gtggcctggg gtagtcggta tggaagcagt aacttttgta aatgttaagt ttagggagga   2640
tggttataat ggaatagtgt ttatggccaa taccaaactt atattgcatg ttgtagctt    2700 ttttggtttc aacaatacct gtgtagatgc ctggggacag gttagtgtac ggggatgtag    2760
tttctatgcg tgttggattg ccacagctgg cagaaccaag agtcaattgt ctctgaagaa    2820
atgcatattt caaagatgta acctgggcat tctgaatgaa ggcgaagcaa gggtccgcca    2880
ctgcgcttct acagatactg gatgttttat tttgattaag ggaaatgcca gcgtaaagca    2940
taacatgatt tgcggtgctt ccgatgagag gccttatcaa atgctcactt gtgctggtgg    3000
gcattgtaat atgctggcta ctgtgcatat tgtttcccat caacgcaaaa atggcctgt    3060 ttttgatcac aatgtgatga cgaagtgtac catgcatgca ggtgggcgta gaggaatgtt    3120
tatgccttac cagtgtaaca tgaatcatgt gaaagtgttg ttggaaccag atgccttttc    3180
cagaatgagc ctaacaggaa tttttgacat gaacatgcaa atctggaaga tcctgaggta    3240
tgatgatacg agatcgaggg tacgcgcatg cgaatgcgga ggcaagcatg ccaggttcca    3300
gccggtgtgt gtagatgtga ctgaagatct cagaccggat catttggtta ttgcccgcac    3360
tggagcagag ttcggatcca gtggagaaga aactgactaa ggtgagtatt gggaaaactt    3420
tggggtggga ttttcagatg gacagattga gtaaaaattt gtttttttctg tcttgcagct    3480 gtcatgagtg gaaacgcttc ttttaagggg ggagtcttca gcccttatct gacagggcgt    3540
ctcccatcct gggcaggagt tcgtcagaat gttatgggat ctactgtgga tggaagaccc    3600
gtccaacccg ccaattcttc aacgctgacc tatgctactt taagttcttc acctttggac    3660
gcagctgcag ctgccgccgc cgcttctgtt gccgctaaca ctgtgcttgg aatgggttac    3720
tatgaaagca tcatggctaa ttccacttcc tctaataacc cttctaccct gactcaggac    3780
aagttacttg tccttttggc ccagctggag gctttgaccc aacgtctggg tgaactttct    3840
cagcaggtgg tcgagttgcg agtacaaact gagtctgctg tcggcacggc aaagtctaaa    3900
taaaaaaatc ccagaatcaa tgaataaata aacaagcttg ttgttgattt aaaatcaagt    3960
gttttatttt cattttttcgc gcacggtatg ccctagacca ccgatctcta tcattgagaa    4020
```

```
ctcggtggat ttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gattttaag ttggcaatat   4320
tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgtttct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaataggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc cttttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
cggttcattg gggtcaaaaa caagtttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt tccaaagta tgcaaacaca tgtcaccctc   5820
ttcaacatcc aggaatgtga ttggcttgta ggtgtatttc acgtgacctg ggtccccgc   5880
tgggggggta taaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt tttttattgt caagtttggt   6120
ggcaaatgat ccatacaggg cgttggataa agtttggca atggatcgca tggtttggtt   6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctaccct ctttcctaga acagaaaggg ggaagtgggt ctagcataag   6420
```

```
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg gatagcatcg   6660
cccccctctg atacttgctc gcacatagtc atatagttca tgtgatggcg ctagcagccc   6720
cggacccaag ttggtgcgat tgggtttttc tgttctgtag acgatctggc gaaagatggc   6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960 gttttttcttt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtattt   7200
gaagtcgatg tcgtcacagg ctccctgttc ccagagttgg aagtctaccc gtttcttgta   7260
ggcggggttg ggcaaagcga aagtaacatc attgaagaga atcttgccgg ccctgggcat   7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaaggggat tagctgcttg ccaaaggacc ccatccaggt   7800
gtaggtttcc acatcgtagg tgagaaagag cctttctgtg cgaggatgag agccaatcgg   7860
gaagaactgg atctcctgcc accagttgga ggaatggctg ttgatgtgat ggaagtagaa   7920
ctccctgcga cgcgccgagc attcatgctt gtgcttgtac agacggccgc agtagtcgca   7980
gcgttgcacg ggttgtatct cgtgaatgag ttgtacctgg cttcccttga cgagaaattt   8040
cagtgggaag ccgaggcctg gcgattgtat ctcgtgcttt actatgttgt ctgcatcggc   8100
ctgttcatct tctgtctcga tggtggtcat gctgacgagc cctcgcggga ggcaagtcca   8160
gacctcggcg cggcagggc ggagctcgag gacgagagcg cgcaggctgg agctgtccag   8220
ggtcctgaga cgctgcggac tcaggttagt aggcagtgtc aggagattaa cttgcatgat   8280
cttttggagg gcgtgcggga ggttcagata gtacttgatc tcaacgggtc cgttggtgga   8340
gatgtcgatg gcttgcaggg ttccgtgtcc cttgggcgct accaccgtgc ccttgttttt   8400
cattttggac ggcggtggct ctgttgcttc ttgcatgttt agaagcggtg tcgagggcgc   8460
gcaccgggcg gcaggggcgg ctcgggaccc ggcggcatgg ctggcagtgg tacgtcggcg   8520
ccgcgcgcgg gtaggttctg gtactgcgcc ctgagaagac tcgcatgcgc gacgacgcgg   8580
cggttgacat cctggatctg acgcctctgg gtgaaagcta ccggcccgt gagcttgaac   8640 ctgaaagaga gttcaacaga atcaatctcg gtatcgttga cggcggcttg cctaaggatt   8700
tcttgcacgt caccagagtt gtcctggtag gcgatcccg ccatgaactg ctcgatctct   8760
tcctcttgaa gatctccgcg gcccgctctc tcgacggtgg ccgcgaggtc gttggagatg   8820
```

```
cgcccaatga gttgagagaa tgcattcatg cccgcctcgt tccagacgcg gctgtagacc    8880
acggccccca cgggatctct cgcgcgcatg accacctggg cgaggttgag ctccacgtgg    8940
cgggtgaaga ccgcatagtt gcataggcgc tggaaaaggt agttgagtgt ggtggcgatg    9000
tgctcggtga cgaagaaata catgatccat cgtctcagcg gcatctcgct gacatcgccc    9060
agagcttcca agcgctccat ggcctcgtag aagtccacgg caaaattaaa aaactgggag    9120
tttcgcgcgg acacggtcaa ctcctcttcc agaagacgga taagttcggc gatggtggtg    9180
cgcacctcgc gctcgaaagc ccctgggatt tcttcctcaa tctcttcttc ttccactaac    9240
atctcttcct cttcaggtgg ggctgcagga ggaggggaa cgcggcgacg ccggcggcgc     9300
acgggcagac ggtcgatgaa tctttcaatg acctctccgc ggcggcgcg catggtttca     9360
gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540
aacctttcga cgaaagcgtc taaccagtca cagtcacaag gtaggctgag tacggcttct    9600
tgtgggcggg ggtggttatg tgttcggtct gggtcttctg tttcttcttc atctcgggaa    9660
ggtgagacga tgctgctggt gatgaaatta aagtaggcag ttctaagacg gcggatggtg    9720
gcgaggagca ccaggtcttt gggtccggct tgctggatac gcaggcgatt ggccattccc    9780
caagcattat cctgacatct agcaagatct ttgtagtagt cttgcatgag ccgttctacg    9840
ggcacttctt cctcacccgt tctgccatgc atacgtgtga gtccaaatcc gcgcattggt    9900
tgtaccagtg ccaagtcagc tacgactctt tcggcgagga tggcttgctg tacttgggta    9960
agggtggctt gaaagtcatc aaaatccaca aagcggtggt aagctcctgt attaatggtg   10020
taagcacagt tggccatgac tgaccagtta actgtctggt gaccagggcg cacgagctcg   10080
gtgtatttaa ggcgcgaata ggcgcggtg tcaaagatgt aatcgttgca ggtgcgcacc    10140
aggtactggt agccaatgag aaagtgtggc ggtggctggc ggtacagggg ccatcgctct   10200
gtagccgggg ctccgggggc gaggtcttcc agcatgaggc ggtggtagcc gtagatgtac   10260
ctggacatcc aggtgatacc ggaggcggtg gtggatgcac gtgggaactc gcgcacgcgg   10320
ttccagatgt tgcgcagcgg catgaagtag ttcatggtag gcacggtctg gccagtgagg   10380
cgcgcgcagt cattgacgct ctgtagacac ggagaaaacg aaagcgatga gcggctcgac   10440
tccgtggtct gggggaacgt gaacgggttg ggtcgcggtg taccccggtt cgagtccaaa   10500
gctaagcgat cacgctcgga tcggccggag ccgcggctaa cgtggtattg gctatcccgt   10560
ctcgacccag ccgacgaata tccagggtac ggagtagagt cgttttttgct gcttttttcct  10620
ggacgtgtgc cattgccacg tcaagcttta gaacgctcag ttctcgggcc gtgagtggct   10680
cgcgcccgta gtctggagaa tcagtcgcca gggttgcgtt gcggtatgcc ccggttggag   10740
cctaagcgcg gctcgtatcg gccggtttcc gcgacaagcg agggtttggc agcccgtta    10800
tttccaagac cccgccagcc gacttctcca gtttacggga gcgagcccctt ttttttttt   10860
ttttgttttt gtcgcccaga tgcatccagt gctgcgacag atgcgccccc agcaacaggc   10920
cccttctcag caacagccac aaaaggctct tcttgctcct gcaactactg cagctgcagc   10980
cgtgagcggc gcgggacagc ccgcctatga tctggacttg gaagagggcg agggattggc   11040
gcgcctgggg gctccatcgc ccgagcggca cccgcgggtg caactaaaaa aggactctcg   11100
cgaggcgtac gtgccccagc agaacctgtt cagggacagg agcggcgagg agccaggaga   11160
gatgcgagca tctcgattta acgcgggtcg cgagctgcgc cacggtctgg atcgaagacg   11220
```

```
ggtgctgcaa gacgaggatt ttgaggtcga tgaagtcaca gggatcagcc cagctagggc    11280
acatgtggcc gcggccaacc tagtctcggc ctacgagcag accgtgaagg aggagcgcaa    11340
cttccaaaaa tcttttaaca accatgtgcg caccctgatc gcccgcgagg aagtgaccct    11400
gggtctgatg catctgtggg acctgatgga ggctatcgcc caaaaccccca ctagcaaacc    11460 actgacagct cagctgtttc tggtggttca acatagcagg gacaacgagg cattcaggga    11520
ggcgttgttg aacatcaccg agcctgatgg gagatggctg tatgatctga tcaacatcct    11580
gcaaagtatt atagtgcagg aacgtagcct gggtttggct gagaaagtgg cagctatcaa    11640
ctactcggtc ttgagcctgg gcaaatacta cgctcgcaag atctacaaga cccctacgt    11700 acccatagac aaggaggtga agatagatgg gttttacatg cgcatgactc tgaaggtgct    11760
gactctgagc gacgatctgg gggtgtatcg caatgacaga atgcaccgcg cggtgagcgc    11820
cagcaggagg cgcgagctga gcgacagaga acttatgcac agcttgcaaa gagctctaac    11880
gggggccggg actgatgggg agaactactt tgacatggga gcggatttgc aatggcaacc    11940
cagtcgcagg gccatggagg ctgcagggtg tgagcttcct tacatagaag aggtggatga    12000
agtcgaggac gaggagggcg agtacttgga agactgatgg cgcgacccgt atttttgcta    12060
gatggaacag cagcaggcac cggaccccgc aatgcgggcg gcgctgcaga gccagccgtc    12120
cggcattaac tcctcggacg attggaccca ggccatgcaa cgcataatgg cgctgacgac    12180
ccgcaacccc gaagccttta gacagcaacc ccaggccaac cgcctttctg ccatactgga    12240
ggccgtagtg ccctcccgct ccaacccccac ccacgagaag gtcctggcta tcgtgaacgc    12300
gctggtggag aacaaggcca tccgtcccga tgaggccggg ctggtataca atgctctctt    12360
ggagcgcgtg gcccgttaca acagcagcaa cgtgcaaacc aacctggacc ggatggtgac    12420
cgatgtgcgc gaggccgtgt ctcagcgcga gcgattccag cgcgacgcca acttggggtc    12480
gttggtagcg ctaaacgctt tcctcagcac ccagcccgcc aacgtgcccc gtggtcagca    12540
agactataca aacttttttga gtgcattgag actcatggta gctgaggtgc cccagagcga    12600
ggtgtaccag tccgggccag attacttctt ccagaccagc agacagggct tgcagacagt    12660
gaacctgact caggctttca agaacctgaa gggtctgtgg ggagtgcacg ccccagtagg    12720
ggatcgcgcg accgtgtcta gcttgctgac tcccaactcc cgcctgctgc tgctgctggt    12780
atcccccttt actgacagcg gtagcattga ccgcaactcg tacttgggct acctgcttaa    12840
cctgtatcgc gaggccatag gacagagcca ggtggacgag cagacctatc aagaaatcac    12900
ccaagtgagc cgcgccctgg gtcaggaaga cacgggcagt ttggaagcca ccctgaactt    12960
cttgctaacc aaccggtcac agaagatccc tcctcagtat gcgcttaccg ctgaggagga    13020
gcggatcctc agatacgtgc aacagagcgt tggactgttc ctgatgcagg aggggcgac    13080 acctaccgcc gcgctggaca tgacagctcg aaacatggag cccagcatgt atgctagtaa    13140
caggcctttc attaacaaac tgctggacta cctgcacagg gcggccgcca tgaactctga    13200
ttatttcacc aatgctatcc tgaacccaca ctggctgccc ccacctggtt tctacactgg    13260
cgagtacgac atgcccgacc ccaatgacgg gttcctgtgg gacgatgtgg acagcagcat    13320
attttccccg cctcccggtt atacagtttg aagaaggaa gggggcgata aagacactc    13380 ttccgtgtcg ctatccggaa cggctggtgc tgccgcgacc gtgcccgaag ctgcaagtcc    13440
tttccctagc ttgccctttt cactaaacag cgttcgcagc agtgaactgg ggagaataac    13500
ccgcccgcgc ttgatgggcg aggatgagta cttgaatgac tctttgctga ggccagagag    13560
ggaaaagaac ttccccaaca atggaataga gagtctggtg gataagatga gtagatggaa    13620
```

```
gacctatgcg caggatcaca gagacgagcc caggatcttg ggggctacaa gcagaccgat    13680
ccgtagacgc cagcgccacg acaggcagat gggtcttgtg tgggacgatg aggactctgc    13740
cgatgatagc agcgtgttgg acttgggtgg aagaggaggg ggcaacccgt tcgctcatct    13800
gcgtcccaga ttcggcgca tgttgtaaaa gtgaaagtaa aataaaaagg caactcacca    13860
aggccatggc gaccgagcgt gcgttcgttc ttttttgtta tctgtgtcta gtacgatgag    13920
gagacgagcc gtgctaggcg gagcggtggt gtatccggag ggtcctcctc cttcttacga    13980
gagcgtgatg cagcaacagg cggcgatgat acagccccca ctggaggctc ccttcgtacc    14040
cccacggtac ctggcgccta cggaagggag aaacagcatt cgttactcgg agctgtcgcc    14100
cctgtacgat accaccaagt tgtatctggt ggacaacaag tcggcggaca tcgcctccct    14160
gaactatcag aacgaccaca gcaacttcct gaccacggtg gtgcagaaca atgactttac    14220
ccccacggag gctagcaccc agaccatcaa ctttgacgag cggtcgcgat ggggcggtca    14280
gctgaagacc atcatgcaca ccaacatgcc caacgtgaac gagtacatgt tcagcaacaa    14340
gttcaaggcg agggtgatgg tgtccagaaa agctcctgaa ggtgttacag taaatgacac    14400
ctatgatcat aaagaggata tcttgaagta tgagtggttt gagttcattt taccagaagg    14460
caacttttca gccaccatga cgatcgacct gatgaacaat gccatcattg acaactacct    14520
ggaaattggc agacagaatg gagtgctgga agtgacatt ggtgttaagt ttgacactag    14580
aaatttcagg ctcgggtggg accccgaaac taagttgatt atgccaggtg tctacactta    14640
tgaggcattc catcctgaca ttgtattgct gcctggttgc ggggtagact ttactgaaag    14700
ccgacttagc aacttgcttg gcatcaggaa gagacatcca ttccaggagg gtttcaaaat    14760
catgtatgaa gatcttgaag ggggtaatat tcctgcccctt ttggatgtca ctgcctatga    14820
ggaaagcaaa aaggatacca ctactgaaac aaccacactg gctgttgcag aggaaactag    14880
tgaagatgat gatataacta gaggagatac ctatataact gaaaaacaaa aacgtgaagc    14940
tgcagctgct gaagttaaaa aagagttaaa gatccaacct ctagaaaaag acagcaagag    15000
tagaagctac aatgtcttgg aagacaaaat caacacagcc taccgcagtt ggtacctgtc    15060
ctacaattac ggtaaccctg agaaaggaat aaggtcttgg acactgctca ccacttcaga    15120
tgtcacctgt ggggcagagc aggtctactg gtcgctccct gacatgatgc aagacccagt    15180
caccttccgc tccacaagac aagtcaacaa ctacccagtg gtgggtgcag agcttatgcc    15240
cgtcttctca aagagttct acaatgagca agccgtgtac tctcagcagc tccgacaggc    15300
cacttcgctc acgcacgtct tcaaccgctt ccctgagaac cagatcctca tccgcccgcc    15360
ggcgcccaca attaccaccg tcagtgaaaa cgttcctgct ctcacagatc acgggaccct    15420
gccgttacgc agcagtatcc ggggagtcca gcgcgtgacc gttactgacg ccagacgccg    15480
cacctgtccc tacgtttaca aggccctggg catagtcgcg ccgcgcgttc tttcaagccg    15540
cactttctaa aaaaaaaaaa aatgtccatt ctcatctcgc ccagtaataa taccggttgg    15600
ggactgtatg cgcccaccaa gatgtatgga ggcgcccgca agcgctctac ccagcatcct    15660
gtgcgcgttc gcggtcattt ccgcgctccc tgggcgcac tcaagggtcg tacccgcact    15720
cggaccacgg tcgatgatgt gatcgaccag gtggtcgccg atgctcgtaa ttatactcct    15780
actgcgccta catctactgt ggatgcagtt attgacagtg tggtggcaga cgcccgcgcc    15840
tatgctcgcc ggaagagccg aaggaggcgc atcgccagge gccacaggge tactcccgcc    15900 atgcgagccg caaaagctat tctgcggagg gccaaacgtg tggggcgaag agccatgctt    15960
agagcggcca gacgcgcggc ttcaggtgcc agcagcggca ggtcccgcag gcgcgcggcc    16020
```

```
acggcggcag cagcggccat tgccaacatg gcccaaccgc gaagaggcaa tgtgtactgg    16080
gtgcgtgatg ccactaccgg ccagcgcgtg cccgtgcgca cccgccccc tcgcacttag     16140 aagatactga gcagtctccg atgttgtgtc ccagcggcaa gtatgtccaa gcgcaaatac    16200
aaggaagaga tgctccaggt catcgcgcct gaaatctacg gtccgccggt gaaggatgaa    16260
aaaaagcccc gcaaaatcaa gcgggtcaaa aataacaaaa aggaagaaga tgacgatgat    16320
gggctggtgg agtttgtgcg cgagttcgcc ccaagacggc gcgtgcagtg gcgcgggcgc    16380
aaagtgcgtc aagtgctcag acccgggacc actgtggttt ttacacctgg cgagcgttcc    16440
agcactactt ttaaacggtc ctatgatgag gtgtacgggg atgacgatat tcttgagcag    16500
gcggcagacc gccttgacga gtttgcttat ggcaagcgca ctagatccag tcccaaagag    16560
gaggctgtgt ccattccttt ggatcatgga aatcccaccc ccagcctcaa accagtcacc    16620
ctgcagcaag tgctgcccgt gcctgcgcgg agaggcgtaa agcgcgaggg tgaggaccta    16680
tatcccacca tgcagctaat ggtgcccaag cgccagaggc tagaagacgt actggagaaa    16740
atgaaagtgg atgccgatat ccagcctgag gtcaaagtaa gacctatcaa ggaagtggcg    16800 ccaggttttgg gagtacaaac cttcgacatc aagattccca ccgagtccat ggaagtgcag    16860
accgaacctg caaacccac cacctcaatt gaggtgcaaa cggaaccctg gatgcccgcg    16920
cccgttgccg cccccagcac cactcgaaga tcacgacgaa agtacggccc agcaagtctg    16980
ctaatgccca actatgctct gcacccatcc atcattccca ctccgggtta cagaggcact    17040
cgctactatc gaaaccggag caacacctct cgccgccgca aaccacctgc aagtcgcact    17100
cgccgtcgcc gccgccgcaa cactgccagc aaattgactc ccgccgccct ggtgcggaga    17160
gtgtaccgcg atggtcgcgc tgaacctctg acgctgccgc gcgcgcgcta ccatccaagc    17220
atcaccactt aatgactgtt gacgctgcct ccttgcagat atggccctca cttgccgcct    17280
tcgcgtcccc attactggct accgaggaag aaactcgcgc cgtagaagga tgttggggcg    17340
agggatgcgc cgccacagac gaaggcgcgc tatcagcaga cgattagggg gtggcttttt    17400
gccagctctt atacccatca tcgccgcagc gatcggggcg ataccaggca tagcttcagt    17460
ggcggttcag gcctcgcagc gccactaaca ttggaaaaaa cttataaata aaaaatagaa    17520
tggactctga cgctcctggt cctgtgacta tgttttttgta gagatggaag acatcaattt    17580
ttcatccctg gctccgcgac acggcacgag gccgtacatg ggcacctgga gcgacatcgg    17640
cacgagccaa ctgaacgggg gcgccttcaa ttggagcagt atctggagcg ggcttaaaaa    17700
ttttggctcg accgtaaaaa cctatgggaa caaagcttgg aacagcagca cagggcaggc    17760
tctgagaaat aagcttaagg aacaaaactt ccaacagaag gtggtcgatg ggatcgcctc    17820
tggtattaac ggcgtagtgg atctggccaa ccaggctgta caaaaacaga taaacagccg    17880
cctggacccg ccgcccgcaa ccctggtga aatggaagtg gaggaagaac ttcctccgct    17940
ggaaaagcgg ggcgacaagc gtccgcgacc cgagctagag cagacgctgg tgacgcgcgc    18000
agacgagccc ccttcatatg aggaggcagt aaagctcgga atgcccacta ccaggcctgt    18060
agctcacatg gctaccgggg tgatgaaacc ttctcagtca catcgacccg ccaccttgga    18120
cttgcctcct cccctgcttc tgcggcgcc tgttcccaaa cctgtcgcta ccagaaagcc    18180
caccgccgta cagcccgtcg ccgtagccag accgcgtcct gggggcacac cgcgcccgaa    18240
agcaaactgg caaagtactc tgaacagcat cgtgggtctg ggcgtgcaga gtgtaaagcg    18300
ccgtcgctgc tattaattaa atatggagta gcgcttaact tgcttgtctg tgtgtatgta    18360
tcatcaccac gccgccgcag cagaggagaa aggaagaggt cgcgcgccga ggctgagttg    18420
```

```
ctttcaagat ggccacccca tcgatgatgc cccaatgggc atacatgcac atcgccggac   18480
aggatgcttc ggagtacctc agtccgggtc tggtgcagtt cgcccgtgca acagacacct   18540
acttcagtat ggggaacaaa tttagaaacc ccacagtggc gcccacccac gatgtgacca   18600
ccgaccgtag ccagcgcctg atgctgcgct tcgtgcccgt tgaccgggaa gacaatacct   18660
actcttacaa agttcgctac acgctggctg taggcgacaa cagagtgctt gacatggcca   18720
gcacattctt tgacattcgg ggggtgcttg atagaggtcc tagcttcaag ccatattccg   18780
gcacagctta caattcactc gctcctaagg gcgcgcccaa tacatctcag tggatagtta   18840
caacaaatgg ggacaatgca gtaactacca ccacaaacac atttggcatt gcttccatga   18900
agggagacaa tattactaaa gaaggtttgc aaattgggaa agacattacc actactgaag   18960
gagaagaaaa gcccatttat gccgataaaa catatcagcc agagcctcaa gttggagaag   19020
aatcatggac tgatactgat ggaacaaatg aaaagtttgg tggaagagcc cttaaaccag   19080
ctaccaacat gaagccatgc tacgggtctt ttgcaagacc tacaaacata aaagggggcc   19140
aagctaaaaa cagaaaagta aaaccaacaa ccgaaggagg ggttgaaact gaggaaccag   19200
atattgatat ggaattttc gatggtagag atgctgttgc aggagcttta gcgcctgaaa   19260
ttgtgcttta tacggaaaat gtaaatttgg aaactccaga cagtcatgtg gtatataaac   19320
cagaaacgtc taataactct catgcaaatt gggtcaaca agccatgcct aacagaccca   19380
attacattgg cttcagggat aacttcgtag gcctaatgta ctacaacagt actggaaata   19440
tgggagtttt ggctggccaa gcatcacaac tgaatgcagt ggttgacttg caggacagaa   19500
atactgaact gtcatatcag cttttgcttg attctctggg agacagaacc agatacttca   19560
gcatgtggaa tcaggctgtg gacagttacg atcccgatgt tcgcattatt gaaaatcatg   19620
gcatcgagga tgaactgcct aattactgtt ttcctctgaa tggcatagga ccagggcaca   19680
catatcaagg cattaaagtt aaaaccgatg acactaatgg atgggaaaaa gatgctaatg   19740
ttgctccagc taatgaaata accataggca acaacctggc tatggaaatt aatatccaag   19800
ctaacctttg gagaagtttt ctgtactcta atgtggcttt gtaccttcca gatgtttaca   19860
agtacacgcc acctaacatt actttgccca ctaacaccaa cacctatgag tacatgaacg   19920
ggcgagtggt atcccatcc ctggttgatt catacatcaa cattggcgcc aggtggtctc   19980
ttgacccaat ggacaatgtg aatccattca accaccaccg caatgctggt ctgcgctaca   20040
ggtccatgct tctgggaaat ggtcgttatg tgccttttca catacaagtg cctcagaaat   20100
tctttgctgt caagaaccta cttcttctac ctggctccta cacctacgag tggaacttcc   20160
gaaaggatgt gaacatggtc ctgcaaagtt ccccttggaaa tgacctcaga acggatggtg   20220
ctaccataag tttcaccagc atcaatctct atgccaccct cttccccatg gctcacaaca   20280
cagcttccac ccttgaagcc atgctgcgca acgataccaa tgatcagtca tttaacgact   20340
acctctctgc agctaacatg ctttaccccca ttcctgccaa tgcaaccaac attccaattt   20400
ccatcccatc tcgcaactgg gcagccttca ggggctggtc cttcaccaga ctcaaaacca   20460
aggagactcc atctcttgga tcagggttcg atccctactt cgtatattct ggatctattc   20520
cctacctgga tggcaccttt taccttaacc acactttcaa gaaggtctcc atcatgtttg   20580
actcctcagt cagctggcct ggcaatgaca ggctgttgag tccaaatgag tttgaaatca   20640
agcgcactgt ggacggggaa ggatacaacg tggcacaatg caacatgacc aaagactggt   20700
tcctggttca gatgcttgcc aattacaaca ttggctacca gggcttttac atccctgagg   20760
gatacaagga tcgcatgtac tccttttttca gaaacttcca gcctatgagc aggcaggtgg   20820
```

```
ttgatgaggt taattacact gactacaaag ccgtcacctt accataccaa cacaacaact    20880
ctggctttgt agggtacctt gcacctacta tgagacaagg ggaaccttac ccagccaatt    20940
atccataccc gctcatcgga actactgccg ttaagagtgt cacccagaaa aagttcctgt    21000
gcgacaggac catgtggcgc attcccttct ccagcaactt catgtccatg ggggcccta    21060
ccgacctggg acagaacatg ctctatgcca actcagccca tgcgctggac atgacttttg    21120
aggtggatcc catggatgag cccaccctgc tttatcttct tttcgaagtc ttcgacgtgg    21180
tcagagtgca ccagccacac cgcggcgtca tcgaggccgt ctacctgcgc acaccgttct    21240
cggccggcaa cgccaccaca taagaagcct cttgcttctt gcaagcagca gctgcagcca    21300
tgacatgcgg gtccggaaac ggctccagcg agcaagagct caaagccatc gtccgagacc    21360
tgggctgcgg accctatttc ctgggaacct ttgacaagcg tttcccgggg ttcatggccc    21420
ccgacaagct cgcctgcgcc atagtcaaca ctgccggacg cgagacgggg ggagagcact    21480
ggctggcttt tggttggaac ccgcgctaca cacctgcta cctttttgat ccttttgggt    21540
tctcggatga gcggctcaaa cagatttacc agtttgagta cgaggggctc ctgcgtcgca    21600
gtgcccttgc taccaaagac cgctgcatca ccctggagaa gtctacccaa agcgtgcagg    21660
gtccgcgctc agccgcctgt ggactttttt gctgtatgtt ccttcatgcc tttgtgcact    21720
ggcccgaccg ccccatggac ggaaaccca ccatgaagtt gctgactggg gtgtccaaca    21780
gcatgctcca atcaccccaa gtccagccca ccctgcgccg caaccaggag gtgctatacc    21840
gcttcctaaa cacccactca tcttactttc gttctcaccg cgcgcgcatt gaaagggcca    21900
ccgcgtttga ccgtatggat atgcaataag tcatgtaaaa ccgtgttcaa taaacagcac    21960
tttattttta catgcactga ggctctggtt ttgctcattt gtttcatcat ttactcagaa    22020
gtcgaatggg ttctggcggg agtcagagtg acccgcgggc agggatacgt tgcggaactg    22080
taacctgttc tgccacttga actcggggat taccagcttg gaactgaa tctcgggaaa    22140
ggtgtcttgc cacaactttc tggtcagttg catagcgcca agcaggtcag gagcagagat    22200
cttgaaatca cagttggggc cggcattctg gacacgggag ttgcgataca ctgggttgca    22260
acactggaac actatcaacg ctgggtgtct tacgcttgcc aacacggttg ggtcactgat    22320
ggtagtcaca tccaagtctt cagcattggc catcccaaag ggggtcatct tacatgtctg    22380
cctgcccatc acgggagcgc agcctggctt gtggttgcaa tcacaatgaa tggggatcag    22440
catcatcctg gcttggtcgg gagttatccc tgggtacaca gccttcatga aggcttcgta    22500
ctgcttaaaa gcttcctggg ccttacttcc ctcggtgtag aacatcccac aggacttgct    22560
ggaaaattga ttagtagtac agttggcatc attcacacaa cagcgggcat cgttgttggc    22620
caactgaacc acatttctgc cccagcggtt ttgggtgatc ttggctctgt ctggattctc    22680
cttcatagcg cgctgcccgt tctcgctcgc cacatccatc tcgataatgt ggtccttctg    22740
gatcatgata gtgccatgca ggcatttcac cttgccttca taatcggtgc atccatgagc    22800
ccacagagcg cacccggtgc actcccaatt attgtgggcg atctcagaat aataatgtac    22860
caatccctgc atgaatcttc ccatcattgt tgtcaaggtc ttcatgctgg taaatgtcag    22920
cgggatgcca cggtgctcct cgttcacata ctggtggcag atacgcttgt attgctcgtg    22980
ctgctctggc atcagcttga aagaggttct cagatcatta tccagcctgt accttttccat    23040
tagcacagcc atcacttcca tgcccttctc ccaggcagat accaggggca gactcaaagg    23100
attcctaaca gcaataaaag tagctccttt agctataggg tcattcttgt cgatcttctc    23160
aacacttctc ttgccatcct tctcaatgat gcgcaccggg gggtagctga agcccacggc    23220
```

```
caccaactga gcctgttctc tttcttcttc actatcctgg ctgatgtctt gcagagggac   23280
atgcttggtc ttcctgggct tcttcttggg agggatcggg ggaggactgt tgctccgctc   23340
cggagacagg gatgactgcg aagtttcgct taccaatacc acctggctct cggtagaaga   23400
accggacccc acacgacggt aggtgttcct cttcggggc agaggtggag gcgactgaga    23460
tgggctgcgg tctggccttg gaggcggatg gctggcagag ctcattccgc gttcgggggt   23520
gtgctcccgg tggcggtcgc ttgactgatt tcctccgcgg ctggccattg tgttctccta   23580
ggcagagaaa caacagacat ggaaactcag ccatcactgc caacatcgct gcaagcacca   23640
tcacacctcg cccccagcag cgacgaggag gagagcttaa ccaccccacc acccagtccc   23700
gctaccacca cctctaccct cgatgatgag gaggaggtcg acgcagccca ggagatgcag   23760
gcgcaggata atgtgaaaac ggaagagatt gaggcagatg tcgagcagga cccgggctat   23820
gtgacgccgg cggagcacca ggaggagctg aaacgctttc tagacagaga ggatgacgac   23880
cgcccagagc atcaagcaga tggcgtttac caggaggctg ggatcaggga tcatgtcgcc   23940
gactacctca ccggccttgg tggggaggac gtgctcctca aacatctagc aaggcagtcg   24000
atcatagtta aagacgcatt gctcgatctc actgaagtgc ccatcagtgt ggaagagctt   24060
agccgcgcct acgagctgaa cctcttttcg cctcaggtac cccccaagcg gcagccaaac   24120
ggcacctgcg aggccaaccc tcgactcaac ttctatccag cttttactat ccccgaagtg   24180
ttggccacct accacatctt tttcaagaac caaaagattc cagtctcctg ccgcgccaac   24240
cgcacccgcg ccgatgccct gctcaacttg ggtccgggag ctcgcttacc tgatatagct   24300
tccttggaag aggttccaaa gatctttgag ggtctgggaa gtgatgagac acgggccgca   24360
aatgctctgc aacagggaga gaatgacatg gatgaacacc acagcgctct ggtggaactg   24420
gagggtgaca atgcccggat tgcagtgctc aagcgcagta tcgtggtcac ccattttgcc   24480 tacccccgctg ttaacctgcc cccccaaagtt atgagcgctg tcatggacca tctgctcatc   24540
aaacgagcaa gacctctttc agaaaaccag aacatgcagg atccagacgc ctcggacgag   24600
ggcaagccgg tagtcagtga cgagcagcta tctcgctggc tgggtaccaa ctcccccga    24660 gatttggaag agaggcgcaa gcttatgatg gctgtagtgc tagtaactgt ggagctggag   24720
tgtctgcgcc gcttttttcac cgaccctgag accctgcgca agctagagga gaacctgcac   24780 tacacctta gacatggctt cgtgcggcag gcatgcaaga tctccaacgt ggagcttacc    24840
aacctggttt cttacatggg cattttgcat gagaaccgac tagggcagag cgtcctgcac   24900 accacccta aagggaggc ccgccgtgac tacatccgag actgtgtcta cctctacctc     24960
tgccatacct ggcaaactgg tatgggtgtg tggcaacagt gtttggaaga gcagaaccta   25020
aaagagctgg acaagctctt gcagagatcc ctcaaagccc tgtggacagg ttttgatgag   25080
cgcaccgtcg cctcggacct ggcagacatc atcttcccg agcgtctcag ggttactctg     25140
cgaaacggcc tgccagactt tatgagccag agcatgctta caactttcg ctctttcatc    25200 ctggaacgct ccggtatcct gcctgccacc tgctgtgcgc tgccctccga ctttgtgcct   25260
ctcacctacc gcgagtgccc accgccgcta tggagccact gctacctgtt ccgcctggcc   25320
aactacctct cctaccactc ggatgttata gaggatgtga gcggagacgg cctgctggaa   25380
tgccactgcc gctgcaatct ttgcacaccc caccgctccc ttgcctgcaa ccccccagttg   25440 ctgagcgaga cccagattat cggcaccttc gagctgcagg gtcccagaag taaaggcgag   25500
gggtcttctc cggggcagag tttgaaactg acaccggggc tgtggacctc cgcctacctg   25560
cgcaagtttc accccgagga ctaccatccc tatgagatca ggttctatga ggaccaatca   25620
```

```
catcctccca aagtcgagct ctcagcctgc gtcatcaccc agggagcaat tctggcccaa   25680
ttgcaagcca tccaaaaatc tcgccaagaa tttctgctaa aaaagggaaa cggggtctac   25740
cttgaccctc agaccggtga ggagctcaac acaaggttcc cccaggatgt cccatcgccg   25800
aggaagcaag aagttgaagg tgcagctgtc gcccccagag gatatgaagg aagactggga   25860
cagtcaggca gaggaggaga tggaagattg ggacagccag gcagaggagg tggacagcct   25920
ggaggaagac agtttggagg aggaagacga ggaggcagag gaggtggaag aagcaaccgc   25980
cgccaaacag ttgtcatcgg cggcggagac aagcaagtcc ccagacagca gcacggctac   26040
catctccgct ccgggtcggg gggcccagcg gcggcccaac agtagatggg acgagaccgg   26100
gcgattccca aacccgacca ccgcttccaa daccggtaag aaggagcgac agggatacaa   26160
gtcctggcgt ggacataaaa acgctatcat ctcctgcttg catgaatgcg ggggcaacat   26220
atccttcacc cggcgatacc tgctcttcca ccacggtgta aacttccccc gcaatatctt   26280
gcattactac cgtcacctcc acagcccta ctgcagtcag caagtcccgg caaccccgac   26340
agaaaaatac agcagcgaca acggtgacca gaaaaccagc agttagaaaa tccacaacaa   26400
gtgcaccagg aggaggactg aggatcacag cgaacgagcc agcgcagacc agagagctga   26460
ggaaccggat cttccaacc ctctatgcca ttttccagca gagtcggggg caagagcagg   26520
aactgaaagt aaaaaaccga tctctgcgct cgctcaccag aagttgtttg tatcacaaga   26580
gcgaagacca acttcagcgc actctcgagg acgccgaggc tctcttcaac aagtactgcg   26640
cgctgactct taaagagtag cccttgcccg cgctcatttt gaaaacggcg ggaatcacgt   26700 caccctggc acctgtcctt tgcccttgtc atgagtaaag agattcccac gccttacatg   26760
tggagctatc agccccaaat ggggttggca gcaggcgctt cccaggacta ctccaccccgc   26820 atgaattggc ttagcgccgg gccctcaatg atatcacggg ttaatgatat acgagcttat   26880
cgaaaccagt tactcctaga acagtcagct ctcaccacca caccccgtca acaccttaat   26940
ccccgaaatt ggcccgccac cctggtgtac caggaaaatc ccgctcccac caccgtacta   27000
cttcctcgag acgcccaggc cgaagttcag atgactaacg caggtgtaca gctggcgggc   27060
ggttccgccc tatgtcgtca ccgacctcaa cagagtataa aacgcctggt gattagaggc   27120
cgaggtatcc agctcaacga cgagtcggtt agctcttcgc ttggtctgcg accagacgga   27180
gtcttccaaa tcgccggctg tgggagatct tccttcactc ctcgtcaggc tgtgctgact   27240
ttggagagtt cgtcctcgca gccccgctcg ggcggcattg gaactctcca gtttgtggag   27300
gagtttactc cctctgtcta cttcaacccc ttctccggct ctcctggcca gtacccggac   27360
gagttcatac caaacttcga cgcaatcagc gagtcagtgg atggctatga ttgatgtcta   27420
atggtggtgc ggctgagcta gctcgactgc gacacctaga ccactgccgc cgctttcgct   27480
gcttcgcccg ggaactcacc gagttcatct acttcgaact ctccgaggag cacccctcagg   27540 gtccggccca cggagtgcgg attaccatcg aagggggaat agactctcgc ctgcatcgca   27600
tcttctccca gcggcccgtg ctaattgaac gcgaccaggg aaatacaacc atctccatct   27660
actgcatctg taaccacccc ggattgcatg aaagcctttg ctgtcttgtt tgtgctgagt   27720
ttaataaaaa ctgagttaag accctcctac ggactaccgc ttcttcaatc aggactttac   27780
aacaccaacc agatcttcca gaagacccag acccttcctc ctttcatcca ggactctaac   27840
tctaccttac cagcacccct cactactaac cttcccgaaa caaacaagct tgcatctcat   27900
ctgcaacacc gcctttcacg aagccttctt tctgccaata ctaccactcc caaaaccgga   27960
ggtgagctcc gcggtcttcc tactgacgac ccctgggtgg tagcgggttt tgtaacgtta   28020
```

```
ggagtagttg cgggtgggct tgtgctgatc ctttgctacc tatacacacc ttgctgtgca   28080
tatttagtca tattgtgctg ttggtttaag aaatgggggc catactagtc gtgcttgctt   28140
tactttcgct tttgggtctg ggctctgcta atctcaatcc tctcgatcac gatccatgtt   28200
tagacttcga cccagaaaac tgcacactta cttttgcacc cgacacaagc cgtctctgtg   28260
gagttcttat taagtgcgga tgggactgca ggtccgttga aattacacat aataacaaaa   28320
catggaacaa taccttatcc accacatggg agccaggagt tccccagtgg tatactgtct   28380
ctgtccgagg tcctgacggt tccatccgca ttagtaacaa cactttcatt ttttctgaaa   28440
tgtgcgatct ggccatgttc atgagcagac agtatgacct atggcctccc agcaaagaga   28500
acattgtggc attttccatt gcttattgct tggtaacatg catcatcact gctatcattt   28560
gtgtgtgcat acacttgctt atagttattc gccctagaca aagcaatgag gaaaaagaga   28620
aaatgcctta accttttttcc tcatacccttt tctttacagc atggcttctg ttacagctct   28680
aattattgcc agcattgtca ctgtcgctca cgggcaaaca attgtccata ttaccttagg   28740
acataatcac actcttgtag ggcccccaat tacttcagag gttatttgga ccaaacttgg   28800
aagtgttgat tattttgata taatttgcaa caaaactaaa ccaatatttg taatctgtaa   28860
cagacaaaat ctcacgttaa ttaatgttag caaaatttat aacggttact attatggtta   28920
tgacagatcc agtagtcaat ataaaaatta cttagttcgc ataactcagc ccaaattaac   28980
agtgccaact atgacaataa ttaaaatggc taataaagca ttagaaaatt ttacatcacc   29040
aacaacaccc aatgaaaaaa acattccaaa ttcaatgatt gcaattattg cggcggtggc   29100
attgggaatg gcactaataa taatatgcat gctcctatat gcttgttact ataaaaagtt   29160
tcaacataaa caggatccac tactaaattt taacatttaa ttttttatac agatgatttc   29220
cactacaatt tttatcatta ctagccttgc agctgtaact tatggccgtt cacacctaac   29280
tgtacctgtt ggctcaacat gtacactaca aggaccccaa gaaggctatg tcacttggtg   29340
gagaatatat gataatggag ggttcgctag accatgtgat cagcctggta caaaattttc   29400
atgcaacgga agagacttga ccattattaa cataacatca aatgagcaag cttctatta   29460 tggaaccaac tataaaaata gtttagatta caacattatt gtagtgccag ccaccacttc   29520
tgctccccgc aaatccactt tctctagcag cagtgccaaa gcaagcacaa ttcctaaaac   29580
agcttctgct atgttaaagc ttccaaaaat cgctttaagt aattccacag ccgctcccaa   29640
tacaattcct aaatcaacaa ttggcatcat tactgccgtg gtagtgggat taatgattat   29700 attttttgtgt ataatgtact acgcctgctg ctatagaaaa catgaacaaa aaggtgatgc   29760
attactaaat tttgatattt aattttttat agaattatga tattgtttca atcaaatacc   29820
actacctcct atgcatacac aaacattcag cctaaatacg ctatgcaact agaaatcaca   29880
atactaattg taattggaat tcttatacta tctgttattc tttattttat attctgccgt   29940 caaatacccca atgttcatag aaattctaaa agacgtccca tctattctcc tatgattagt   30000
cgtccccata tggctctgaa tgaaatctaa gatcttttt ttttctctt acagtatggt   30060 gaacatcaat catgatccct agaaatttct tcttcaccat actcatctgt gcttttaatg   30120
tctgtgctac tttcacagca gtagccactg caagcccaga ctgtatagga ccatttgctt   30180
cctatgcact ttttgccttc gttacttgca tctgcgtgtg tagcatagtc tgcctggtta   30240 ttaattttt ccaactggta gactggatct ttgtgcgaat tgcctaccta cgtcaccatc   30300
ccgaataccg caatcaaaat gttgcggcac ttcttaggct tatttaaaac catgcaggct   30360
atgctaccag tcattttaat tttgctacta ccctgcattc ccctagcttc caccgccact   30420
```

```
cgcgctacac ctgaacaact tagaaaatgc aaatttcaac aaccatggtc atttcttgat   30480
tgctaccatg aaaaatctga ttttcccaca tactggatag tgattgttgg aataattaac   30540
atactttcat gtacctttt  ctcaatcaca atatacccca catttaattt tgggtggaat   30600
tctcccaatg cactgggtta cccacaagaa ccagatgaac atattccact acaacacata   30660
caacaaccac tagcactggt acagtatgaa aatgagccac aaccttcact gcccctgcc    30720 attagttact tcaacctaac cggcggagat gactgaccca atcgccacat catccaccgc   30780
tgccaaggag ctgctggaca tggacggacg tgcctcagaa cagcgactca tccaactacg   30840
cattcgtcag cagcaggaac gagcagtaaa agagctaagg gatgccattg ggattcacca   30900
gtgcaaaaaa ggcatattct gcttagtaaa acaatccaaa atctcctacg agatcaccgc   30960
tactgaccat cgtctctcat acgagctcgg tccgcagcga caaaaattca cctgcatggt   31020
gggaatcaac cccatagtta tcacccagca gtctggagat actaagggtt gtatccagtg   31080
ttcctgtgat tccaccgagt gcatctacac actgctgaag accctctgcg gccttcgaga   31140
cctcctaccc atgaactaat cattgccccct accttaccca atcaaaatat taataaagac   31200
acttacttga aatcagcaat acagtctttg tcaaaacttt ctaccagcag cacctcaccc   31260
tcttcccaac tctggtactc taaacgtcgg agggtggcat actttctcca cactttgaaa   31320
gggatgtcaa attttatttc ctcttctttg cccacaatct tcatttcttt atccccagat   31380
ggccaagcga gctcggctaa gcacttcctt caacccggtg tacccttatg aagatgaaag   31440
cagctcacaa cacccattta taaatcctgg tttcatttcc cctgacgggt tcacacaaag   31500
tccaaacggg gttttaagtc ttaaatgtgt taatccactt accactgcaa gcggctccct   31560
ccaacttaaa gtgggaagtg gtcttacagt agacactact gatggatcct tagaagaaaa   31620
catcaaagtt aacacccccc taacaaagtc aaaccattct ataaatttac caataggaaa   31680
cggtttgcaa atagaacaaa acaaactttg cagtaaactc ggaaatggtc ttacatttga   31740
ctcttccaat tctattgcac tgaaaaataa cactttatgg acaggtccaa aaccagaagc   31800
caactgcata attgaatacg ggaaacaaaa cccagatagc aaaactaactt taatccttgt   31860 aaaaaatgga ggaattgtta atggatatgt aacgctaatg ggagcctcag actacgttaa   31920
caccttattt aaaaacaaaa atgtctccat taatgtagaa ctatactttg atgccactgg   31980
tcatatatta ccagactcat cttctcttaa aacagatcta gaactaaaat acaagcaaac   32040
cgctgacttt agtgcaagag gttttatgcc aagtactaca gcgtatccat tgtccttcc    32100 taatgcggga acacataatg aaaattatat ttttggtcaa tgctactaca aagcaagcga   32160
tggtgcccct tttccgttgg aagttactgt tatgcttaat aaacgcctgc cagatagtcg   32220
cacatcctat gttatgactt ttttatggtc cttgaatgct ggtctagctc cagaaactac   32280
tcaggcaacc ctcataacct ccccatttac cttttcctat attagagaag atgactgaca   32340
acaaaaataa agttcaacat ttttattga  aattcctttt acagtattcg agtagttatt   32400
ttgcctcccc cttcccattt aacagaatac accaatctct ccccacgcac agctttaaac   32460
atttggatac cattagagat agacatagtt ttagattcca cattccaaac agtttcagag   32520
cgagccaatc tggggtcagt aatacataaa aatgcatcgg atagtctttt taaagcgctt   32580
tcacagtcca actgttgcgg atgcgactcc ggagtctgaa tcacggtcat ctggaagaag   32640
aacgatggga atcataatcc gaaaacggaa tcgggcgatt tgtctcatc  aaacccacaa   32700 gcaaccgctg tctgcgtcgc tccgtgcgac tgctgtttat gggatcgggg tccgcagtgt   32760
cctgaagcat gattttaata gcccttaaca ttaactttct ggtgcgatgc gcgcagcaac   32820
```

```
gcattctgat tcacttaga ttactacagt aggtacagca cattatcaca atattgttta   32880
ataaaccata attaaaagcg ctccagccaa aactcatatc tgatataatc gccctgcat    32940
gaccatcata ccaaagttta atataaatta aatgtcgttc cctcaaaaac acactaccca   33000
catacatgat ctcttttggc atgtgcatat taacaatttg tctgtaccat ggacaacgtt   33060
ggttaatcat gcaacccaat ataaccttcc ggaaccacac tgccaacacc gctcccccag   33120
ccatgcattg aagtgaaccc tgctgattac aatgacaatg aagaacccaa ttctctcgac   33180
catgaatcac ttgagactga aaaatatcta tagtagcaca acaaagacat aaatgcatgc   33240
atcttctcat aattttttaac tcctctggat ttaaaaacat atcccaagga atgggaaact   33300
cttgcagaac agtaaagctg gcagaacaag gaagaccacg aacacaactt acactatgca   33360
tagtcatagt atcacaatct ggcaacagcg ggtggtcttc agtcatagaa gctcgggttt   33420
cattttcctc acatcgtggt aattgggctc tggtgtaagg gtgatgtctg gcgcatgatg   33480
tggagcgtgc gcgcaacctt gtcataatgg agttgcttcc tgacattctc gtattttgta   33540
tagcaaaacg ctgccctggc acaacacact cttcttcgtc ttctatcctg ccgcttagtg   33600
tgttccgtct gataattcaa gtacagccac actcttaagt tggtcaaaag aatgctggct   33660
tcagttgtaa tcaaaactcc atcatattta attgttctaa ggaaatcatc cacggtagca   33720
tatgcaaatc ccaaccaagc aatgcaactg gattgcgttt caagcagcag aggagaggga   33780
agagacggaa gaatcatgtt aatttttatt ccaaacgatc tcgcagtact tcaaattgta   33840
gatcgcgcag atggcatcta tcgccccac tgtgttggtg aaaaagcaca gctaaatcaa    33900
aagaaatgcg attttcaagg tgctcaacgg tggcttccaa caaagcctcc acgcgcacat   33960
ccaaaaacaa aagaatacca aaagaaggag cattttctaa ctcctcaaac atcatattac   34020
attcctgcac cattcccaga taattttcag cttttccagcc ttgaattatt cgtgtcagtt   34080
cttgtggtaa atccaaacca cacattacaa acaggtcccg gagggcgccc tccaccacca   34140
ttcttaaaca caccctcata atgacaaaat atcttgctcc tgtgtcacct gtagcaaatt   34200
aagaatggca tcatcaattg acatgcccctt ggctctaagt tcttctctaa gttctagttg   34260
tagatactct ctcatattat caccaaactg cttagccaga agcccccgg gaacaatagc     34320
aggggacgct acagtgcagt acaagcgcag acctccccaa ttggctccag caaaaacaag   34380
attagaataa gcatactggg aaccaccagt aatatcatca aagttgctgg aaatataatc   34440
aggcagagtt tcttgtaaaa attgaataaa agaaaaattt tccaaagaaa cattcaaaac   34500
cgttgggatg caaatacaat aggttaccgc gctgcgctcc aacattgtta gttttgaatt   34560
agtctgcaaa ataaagaaa caagcgtcat atcatagtag cctgtcgaac aggtggaaaa    34620
atcagtcttt ccatcacaag acaagccaca gggtctccag ctcgaccctc gtaaaacctg   34680
tcattgtgat taaacaacag caccgaaagt tcctcgcggt ggccagcatg aataattctt   34740
gatgaagcat acaatccaga catgttagca tcagttaaag agaaaaaaca gccaacatag   34800
cctctgggta taattatgct taattttaag tatagcaaag ccaccctcg cggatacaaa    34860
gtaaaaggca caggagaata aaaaatataa ttatttctct gctgctgttc aggcaacgtt   34920
gctcccggtc cctctaaata gacatacaaa gcctcatcag ccatggctta ccaggcaaag   34980
tacagcgggc gcacaaagca caagctctaa agaagctcta aaaacactct ccaacctctc   35040
cacaatatat acacaagccc taaactgacg taatgggagt aaagtgaaaa aaaaataccg   35100
ccaagcccaa cacacacccc gaaactgcgt cagcaggaaa aagtacagtt tcacttccgc   35160
attcccaaca agcgtaactt cctctttctc atggtacgtc acatccgatt aacttgcaac   35220
```

-continued

| | | |
|---|---|---|
| gtcattttcc cacggtcgcg ccgccccttt tagccgttaa ccccgcagcc aatcaccaca | 35280 |
| cagcgcgcac ttttttaaat tacctcattt acatgttggc accattccat ctataaggta | 35340 |
| tattatatag ataga | 35355 |

<210> SEQ ID NO 3
<211> LENGTH: 32325
<212> TYPE: DNA
<213> ORGANISM: adenovirus

<400> SEQUENCE: 3

| | | |
|---|---|---|
| ctatctatat aatatacctt atagatggaa tggtgccaat atgtaaatga ggtgatttta | 60 |
| aaaagtgtgg atcgtgtggt gattggctgt ggggttaacg gctaaaaggg gcggtgcgac | 120 |
| cgtgggaaaa tgacgttttg tgggggtgga gttttttttgc aagttgtcgc gggaaatgtg | 180 |
| acgcataaaa aggcttttttt ctcacggaac tacttagttt tcccacggta tttaacagga | 240 |
| aatgaggtag ttttgaccgg atgcaagtga aaattgttga ttttcgcgcg aaaactgaat | 300 |
| gaggaagtgt ttttctgaat aatgtggtat ttatggcagg gtggagtatt tgttcagggc | 360 |
| caggtagact ttgacccatt acgtggaggt ttcgattacc gtgtttttta cctgaatttc | 420 |
| cgcgtaccgt gtcaaagtct tctgttttta cgtaggtgtc agctgatcgc tagggtattt | 480 |
| atacctcagg gtttgtgtca agaggccact cttgagtgcc agcgagaaga gttttctcct | 540 |
| ctgcgccggc agtttaataa taaaaaaatg agagatttgc gatttctgcc tcaggaaata | 600 |
| atctctgctg agactgggaa tgaaatattg gagcttgtgg tgcacgccct gatgggagac | 660 |
| gatccggagc cacctgtgca gcttttttgag cctcctacgc ttcaggaact gtatgattta | 720 |
| gaggtagagg gatcggagga ttctaatgag gaagctgtaa atggcttttt taccgattct | 780 |
| atgctttttag ctgctaatga agggttagaa ttagatccgc ctttggacac ttttgatact | 840 |
| ccaggggtaa ttgtggaaag cggtacaggt gtaagaaaat tacctgattt gagttccgtg | 900 |
| gactgtgatt tgcactgcta tgaagacggg tttcctccga gtgatgagga ggaccatgaa | 960 |
| aaggagcagt ccatgcagac tgcagcgggt gagggagtga aggctgccaa tgttggtttt | 1020 |
| cagttggatt gcccggagct tcctggacat ggctgtaagt cttgtgaatt tcacaggaaa | 1080 |
| aatactggag taaggaact gttatgttcg ctttgttata tgagaacgca ctgccacttt | 1140 |
| atttacagta agtgtgttta agttaaaatt taaaggaata tgctgttttt cacatgtata | 1200 |
| ttgagtgtga gttttgtgct tcttattata ggtcctgtgt ctgatgctga tgaatcacca | 1260 |
| tctcctgatt ctactacctc acctcctgag attcaagcac ctgttcctgt ggacgtgcgc | 1320 |
| aagcccattc ctgtgaagct taagcctggg aaacgtccag cagtgaaaaa acttgaggac | 1380 |
| tgttacaggg gtgggacgg acctttggac ttgagtacac ggaaacgtcc aagacaataa | 1440 |
| gtgttccata tccgtgttta cttaaggtga cgtcaatatt tgtgtgacag tgcaatgtaa | 1500 |
| taaaaatatg ttaactgttc actggttttt attgcttttt gggcggggac tcaggtatat | 1560 |
| aagtagaagc agacctgtgt ggttagctca taggagctgg cttttcatcca tggaggtttg | 1620 |
| ggccattttg gaagacctta ggaagactag gcaactgtta gagaacgctt cggacggagt | 1680 |
| ctccggtttt tggagattct ggttcgctag tgaattagct agggtagttt ttaggataaa | 1740 |
| acaggactat aaacaagaat ttgaaaagtt gttggtagat tgcccaggac ttttttgaagc | 1800 |
| tcttaatttg ggccatcagg ttcactttaa agaaaaagtt ttatcagttt tagacttttc | 1860 |
| aaccccaggt agaactgctg ctgctgtggc ttttcttact tttatattag ataaatggat | 1920 |
| cccgcagact catttcagca ggggatacgt tttggatttc atagccacag cattgtggag | 1980 |

```
aacatggaag gttcgcaaga tgaggacaat cttaggttac tggccagtgc agcctttggg   2040
tgtagcggga atcctgaggc atccaccggt catgccagcg gttctggagg aggaacagca   2100
agaggacaac ccgagagccg gcctggaccc tccagtggag gaggcggagt agctgacttg   2160
tctcctgaac tgcaacgggt gcttactgga tctacgtcca ctggacggga tagggcgtt    2220 aagagggaga gggcatctag tggtactgat gctagatctg agttggcttt aagtttaatg   2280
agtcgcagac gtcctgaaac catttggtgg catgaggttc agaaagaggg aagggatgaa   2340
gtttctgtat tgcaggagaa atattcactg gaacaggtga aaacatgttg gttggagcct   2400
gaggatgatt gggaggtggc cattaaaaat tatgccaaga tagctttgag gcctgataaa   2460
cagtataaga ttactagacg gattaatatc cggaatgctt gttacatatc tggaaatggg   2520
gctgaggtgg taatagatac tcaagacaag gcagttatta tgatgctgcat gatggatatg   2580 tggcctgggg tagtcggtat ggaagcagta acttttgtaa atgttaagtt taggggagat   2640
ggttataatg aatagtgtt tatggccaat accaaactta tattgcatgg ttgtagcttt    2700
tttggtttca acaatacctg tgtagatgcc tggggacagg ttagtgtacg gggatgtagt   2760
ttctatgcgt gttggattgc cacagctggc agaaccaaga gtcaattgtc tctgaagaaa   2820
tgcatatttc aaagatgtaa cctgggcatt ctgaatgaag gcgaagcaag ggtccgccac   2880
tgcgcttcta cagatactgg atgttttatt ttgattaagg gaaatgccag cgtaaagcat   2940
aacatgattt gcggtgcttc cgatgagagg cctatcaaa tgctcacttg tgctggtggg    3000
cattgtaata tgctggctac tgtgcatatt gtttcccatc aacgcaaaaa atggcctgtt   3060
tttgatcaca atgtgatgac gaagtgtacc atgcatgcag gtgggcgtag aggaatgttt   3120
atgccttacc agtgtaacat gaatcatgtg aaagtgttgt tggaaccaga tgccttttcc   3180
agaatgagcc taacaggaat ttttgacatg aacatgcaaa tctggaagat cctgaggtat   3240
gatgatacga atcgagggt acgcgcatgc gaatgcggag gcaagcatgc caggttccag   3300
ccggtgtgtg tagatgtgac tgaagatctc agaccggatc atttggttat tgcccgcact   3360
ggagcagagt tcggatccag tggagaagaa actgactaag gtgagtattg ggaaaacttt   3420
ggggtgggat tttcagatgg acagattgag taaaaatttg ttttttctgt cttgcagctg   3480
tcatgagtgg aaacgcttct tttaaggggg gagtcttcag cccttatctg acagggcgtc   3540
tcccatcctg ggcaggagtt cgtcagaatg ttatgggatc tactgtggat ggaagacccg   3600
tccaacccgc caattcttca acgctgacct atgctacttt aagttcttca cctttggacg   3660
cagctgcagc tgccgccgcc gcttctgttg ccgctaacac tgtgcttgga atgggttact   3720
atggaagcat catggctaat tccacttcct ctaataaccc ttctaccctg actcaggaca   3780
agttacttgt ccttttggcc cagctggagg ctttgaccca acgtctgggt gaactttctc   3840
agcaggtggt cgagttgcga gtacaaactg agtctgctgt cggcacggca aagtctaaat   3900
aaaaaaatcc cagaatcaat gaataaataa acaagcttgt tgttgattta aaatcaagtg   3960
tttttatttc atttttcgcg cacggtatgc cctagaccac cgatctctat cattgagaac   4020
tcggtggatt ttttccagga tcctatagag gtgggattga atgtttagat acatgggcat   4080
taggccgtct ttggggtgga gatagctcca ttgaagggat tcatgctccg ggtagtgtt    4140 gtaaatcacc cagtcataac aaggtcgcag tgcatggtgt tgcacaatat ctttttagaag  4200 taggctgatt gccacagata agcccttggt gtaggtgttt acaaaccggt tgagctggga   4260
tgggtgcatt cggggtgaaa ttatgtgcat tttggattgg attttaagt tggcaatatt    4320 gccgccaaga tcccgtcttg ggttcatgtt atgaaggacc accaagacgg tgtatccggt   4380
```

```
acatttagga aatttatcgt gcagcttgga tggaaaagcg tggaaaaatt tggagacacc   4440
cttgtgtcct ccaagatttt ccatgcactc atccatgata atagcaatgg ggccgtgggc   4500
agcggcgcgg gcaaacacgt tccgtgggtc tgacacatca tagttatgtt cctgagttaa   4560
atcatcataa gccattttaa tgaatttggg gcggagagta ccagattggg gtatgaatgt   4620
tccttcgggc cccggagcat agttcccctc acagatttgc atttcccaag ctttcagttc   4680
cgagggtgga atcatgtcca cctgggggggc tatgaaaaac accgtttctg gggcggggt    4740 gattaattgt gatgatagca aatttctgag caattgagat ttgccacatc cggtggggcc   4800
ataaatgatt ccgattacgg gttgcaggtg gtagtttagg gaacggcaac tgccgtcttc   4860
tcgaagcaag ggggccacct cgttcatcat ttcccttaca tgcatatttt cccgcaccaa   4920
atccattagg aggcgctctc ctcctagtga tagaagttct tgtagtgagg aaaagttttt   4980
cagcggtttc agaccgtcag ccatgggcat tttggagaga gtttgctgca aaagttctag   5040
tctgttccac agttcagtga tgtgttctat ggcatctcga tccagcagac ctcctcgttt   5100
cgcgggtttg gacggctcct ggaatagggt atgagacgat gggcgtccag cgctgccagg   5160
gttcggtcct tccagggtct cagtgttcga gtcagggttg tttccgtcac agtgaagggg   5220
tgtgcgcctg cttgggcgct tgccagggtg cgcttcagac tcatcctgct ggtcgaaaac   5280
ttctgtcgct tggcgccctg tatgtcggcc aagtagcagt ttaccatgag ttcgtagttg   5340
agcgcctcgg ctgcgtggcc tttggcgcgg agcttacctt tggaagtttt cttgcatacc   5400
gggcagtata ggcatttcag cgcatacaac ttgggcgcaa ggaaaacgga ttctggggag   5460
tatgcatctg cgccgcagga ggcgcaaaca gtttcacatt ccaccagcca ggttaaatcc   5520
ggttcattgg ggtcaaaaac aagttttccg ccatatttt tgatgcgttt cttaccttg    5580 gtctccatga gttcgtgtcc tcgttgagtg acaaacaggc tgtccgtgtc cccgtagact   5640
gattttacag gcctcttctc cagtggagtg cctcggtctt cttcgtacag gaactctgac   5700
cactctgata caaaggcgcg cgtccaggcc agcacaaagg aggctatgtg ggaggggtag   5760
cgatcgttgt caaccagggg gtccacctt tccaaagtat gcaaacacat gtcaccctct    5820
tcaacatcca ggaatgtgat tggcttgtag gtgtatttca cgtgacctgg ggtccccgct   5880
gggggggtat aaaaggggge ggttctttgc tcttcctcac tgtcttccgg atcgctgtcc   5940
aggaacgtca gctgttgggg taggtattcc ctctcgaagg cgggcatgac ctctgcactc   6000
aggttgtcag tttctaagaa cgaggaggat ttgatattga cagtgccggt tgagatgcct   6060
ttcatgaggt tttcgtccat ctggtcagaa aacacaattt ttttattgtc aagtttggtg   6120
gcaaatgatc catacagggc gttggataaa agtttggcaa tggatcgcat ggtttggttc   6180
ttttccttgt ccgcgcgctc tttggcggcg atgttgagtt ggacatactc gcgtgccagg   6240
cacttccatt cggggaagat agttgttaat tcatctggca cgattctcac ttgccaccct   6300
cgattatgca aggtaattaa atccacactg gtggccacct cgcctcgaag gggttcattg   6360
gtccaacaga gcctacctcc tttcctagaa cagaaggggg gaagtgggtc tagcataagt   6420
tcatcgggag ggtctgcatc catggtaaag attcccggaa gtaaatcctt atcaaaatag   6480
ctgatgggag tggggtcatc taaggccatt tgccattctc gagctgccag tgcgcgctca   6540
tatgggttaa ggggactgcc ccatggcatg ggatgggtga gtgcagaggc atacatgcca   6600
cagatgtcat agacgtagat gggatcctca aagatgccta tgtaggttgg atagcatcgc   6660 cccctctga tacttgctcg cacatagtca tatagttcat gtgatggcgc tagcagcccc    6720
ggacccaagt tggtgcgatt gggttttct gttctgtaga cgatctggcg aaagatggcg    6780
```

```
tgagaattgg aagagatggt gggtctttga aaaatgttga aatgggcatg aggtagacct   6840
acagagtctc tgacaaagtg ggcataagat tcttgaagct tggttaccag ttcggcggtg   6900
acaagtacgt ctagggcgca gtagtcaagt gtttcttgaa tgatgtcata acctggttgg   6960
tttttctttt cccacagttc gcggttgaga aggtattctt cgcgatcctt ccagtactct   7020
tctagcggaa acccgtcttt gtctgcacgg taagatccta gcatgtagaa ctgattaact   7080
gccttgtaag ggcagcagcc cttctctacg ggtagagagt atgcttgagc agcttttcgt   7140
agcgaagcgt gagtaagggc aaaggtgtct ctgaccatga cttttgaggaa ttggtatttg   7200 aagtcgatgt cgtcacaggc tccctgttcc cagagttgga agtctacccg tttcttgtag   7260
gcggggttgg gcaaagcgaa agtaacatca ttgaagagaa tcttgccggc cctgggcatg   7320
aaattgcgag tgatgcgaaa aggctgtggt acttccgctc ggttattgat aacctgggca   7380
gctaggacga tctcgtcgaa accgttgatg ttgtgtccta cgatgtataa ttctatgaaa   7440
cgcggcgtgc ctctgacgtg aggtagctta ctgagctcat caaaggttag gtctgtgggg   7500
tcagataagg cgtagtgttc gagagcccat tcgtgcaggt gaggattcgc tttaaggaag   7560
gaggaccaga ggtccactgc cagtgctgtt tgtaactggt cccggtactg acgaaaatgc   7620
cgtccgactg ccatttttc tggggtgacg caatagaagg tttgggggtc ctgccgccag   7680
cgatcccact tgagttttat ggcgaggtca taggcgatgt tgacgagccg ctggtctcca   7740
gagagtttca tgaccagcat gaaggggatt agctgcttgc caaaggaccc catccaggtg   7800
taggtttcca catcgtaggt gagaaagagc ctttctgtgc gaggatgaga gccaatcggg   7860
aagaactgga tctcctgcca ccagttggag gaatggctgt tgatgtgatg gaagtagaac   7920
tccctgcgac gcgccgagca ttcatgcttg tgcttgtaca gacggccgca gtagtcgcag   7980
cgttgcacgg gttgtatctc gtgaatgagt tgtacctggc ttcccttgac gagaaatttc   8040
agtgggaagc cgaggcctgg cgattgtatc tcgtgcttta ctatgttgtc tgcatcggcc   8100
tgttcatctt ctgtctcgat ggtggtcatg ctgacgagcc ctcgcgggag gcaagtccag   8160
acctcggcgc ggcaggggcg gagctcgagg acgagcgcg caggctgga gctgtccagg   8220 gtcctgagac gctgcggact caggttagta ggcagtgtca ggagattaac ttgcatgatc   8280
ttttggaggg cgtgcgggag gttcagatag tacttgatct caacgggtcc gttggtggag   8340
atgtcgatgg cttgcagggt tccgtgtccc ttgggcgcta ccaccgtgcc cttgttttc   8400 attttggacg gcgtggctc tgttgcttct tgcatgttta aagcggtgt cgagggcgcg   8460 caccgggcgg caggggcggc tcgggaccg gcggcatggc tggcagtggt acgtcggcgc   8520
cgcgcgcggg taggttctgg tactgcgccc tgagaagact cgcatgcgcg acgacgcggc   8580
ggttgacatc ctggatctga cgcctctggg tgaaagctac cggccccgtg agcttgaacc   8640
tgaaagagag ttcaacagaa tcaatctcgg tatcgttgac ggcggcttgc ctaaggattt   8700
cttgcacgtc accagagttg tcctggtagg cgatctccgc catgaactgc tcgatctctt   8760
cctcttgaag atctccgcgg cccgctctct cgacggtggc cgcgaggtcg ttggagatgc   8820
gcccaatgag ttgagagaat gcattcatgc ccgcctcgtt ccagacgcgg ctgtagacca   8880
cggcccccac gggatctctc gcgcgcatga ccacctgggc gaggttgagc tccacgtggc   8940
gggtgaagac cgcatagttg cataggcgct ggaaaaggta gttgagtgtg gtggcgatgt   9000
gctcggtgac gaagaaatac atgatccatc gtctcagcgg catctcgctg acatcgccca   9060
gagcttccaa cgcgctccatg gcctcgtaga agtccacgcg aaaattaaaa aactgggagt   9120
ttcgcgcgga cacggtcaac tcctcttcca gaagacggat aagttcggcg atggtggtgc   9180
```

```
gcacctcgcg ctcgaaagcc cctgggattt cttcctcaat ctcttcttct tccactaaca   9240
tctcttcctc ttcaggtggg gctgcaggag gaggggggaac gcggcgacgc cggcggcgca   9300
cgggcagacg tcgatgaat  cttcaatga  cctctccgcg gcggcggcgc atggtttcag   9360
tgacggcgcg gccgttctcg cgcggtcgca gagtaaaaac accgccgcgc atctccttaa   9420
agtggtgact gggaggttct ccgtttggga gggagagggc gctgattata cattttatta   9480
attggcccgt agggactgca cgcagagatc tgatcgtgtc aagatccacg ggatctgaaa   9540
acctttcgac gaaagcgtct aaccagtcac agtcacaagg taggctgagt acggcttctt   9600
gtgggcgggg gtggttatgt gttcggtctg ggtcttctgt ttcttcttca tctcgggaag   9660
gtgagacgat gctgctggtg atgaaattaa agtaggcagt tctaagacgg cggatggtgg   9720
cgaggagcac caggtctttg ggtccggctt gctggatacg caggcgattg gccattcccc   9780
aagcattatc ctgacatcta gcaagatctt tgtagtagtc ttgcatgagc cgttctacgg   9840
gcacttcttc ctcacccgtt ctgccatgca tacgtgtgag tccaaatccg cgcattggtt   9900
gtaccagtgc caagtcagct acgactcttt cggcgaggat ggcttgctgt acttgggtaa   9960
gggtggcttg aaagtcatca aaatccacaa agcggtggta agctcctgta ttaatggtgt  10020
aagcacagtt ggccatgact gaccagttaa ctgtctggtg accagggcgc acgagctcgg  10080
tgtatttaag gcgcgaatag gcgcgggtgt caaagatgta atcgttgcag gtgcgcacca  10140
gatactggta ccctataaga aaatgcggcg gtggttggcg gtagagaggc catcgttctg  10200
tagctggagc gccaggggcg aggtcttcca acataaggcg gtgatagccg tagatgtacc  10260
tggacatcca ggtgattcct gcggcggtag tagaagcccg aggaaactcg cgtacgcggt  10320
tccaaatgtt gcgtagcggc atgaagtagt tcattgtagg cacggtttga ccagtgaggc  10380
gcgcgcagtc attgatgctc tatagacacg gagaaaatga aagcgttcag cgactcgact  10440
ccgtagcctg gaggaacgtg aacgggttgg gtcgcggtgt accccggttc gagacttgta  10500
ctcgagccgg ccggagccgc ggctaacgtg gtattggcac tcccgtctcg acccagccta  10560
caaaaatcca ggatacggaa tcgagtcgtt ttgctggttt ccgaatggca gggaagtgag  10620
tcctattttt ttttttttgcc gctcagatgc atcccgtgct gcgacagatg cgcccccaac  10680
aacagccccc ctcgcagcag cagcagcagc aatcacaaaa ggctgtccct gcaactactg  10740
caactgccgc cgtgagcggt gcgggacagc ccgcctatga tctggacttg gaagagggcg  10800
aaggactggc acgtctaggt gcgccttcac ccgagcggca tccgcgagtt caactgaaaa  10860
aagattctcg cgaggcgtat gtgccccaac agaacctatt tagagacaga agcggcgagg  10920
agccggagga gatgcgagct tcccgcttta acgcgggtcg tgagctgcgt cacggtttgg  10980
accgaagacg agtgttgcgg gacgaggatt tcgaagttga tgaaatgaca gggatcagtc  11040
ctgccagggc acacgtggct gcagccaacc ttgtatcggc ttacgagcag acagtaaagg  11100
aagagcgtaa cttccaaaag tctttttaata atcatgtgcg aaccctgatt gcccgcgaag  11160
aagttaccct tggtttgatg catttgtggg atttgatgga agctatcatt cagaacccta  11220
ctagcaaacc tctgaccgcc cagctgtttc tggtggtgca acacagcaga gacaatgagg  11280
cttttcagaga ggcgctgctg aacatcaccg aacccgaggg gagatggttg tatgatctta  11340
tcaacattct acagagtatc atagtgcagg agcggagcct gggcctggcc gagaaggtgg  11400
ctgccatcaa ttactcggtt ttgagcttgg gaaaatatta cgctcgcaaa atctacaaga  11460
ctccatacgt tcccatagac aaggaggtga agatagatgg gttctacatg cgcatgcgc   11520
tcaaggtctt gaccctgagc gatgatcttg gggtgtatcg caatgacaga atgcatcgcg  11580
```

```
cggttagcgc cagcaggagg cgcgagttaa gcgacaggga actgatgcac agtttgcaaa   11640
gagctctgac tggagctgga accgagggtg agaattactt cgacatggga gctgacttgc   11700
agtggcagcc tagtcgcagg gctctgagcg ccgcgacggc aggatgtgag cttccttaca   11760
tagaagaggc ggatgaaggc gaggaggaag agggcgagta cttggaagac tgatggcaca   11820
acccgtgttt tttgctagat ggaacagcaa gcaccggatc ccgcaatgcg ggcggcgctg   11880
cagagccagc cgtccggcat taactcctcg gacgattgga cccaggccat gcaacgtatc   11940
atggcgttga cgactcgcaa ccccgaagcc tttagacagc aaccccaggc caaccgtcta   12000
tcggccatca tggaagctgt agtgccttcc cgctctaatc ccactcatga aaggtcctg    12060 gccatcgtga acgcgttggt ggagaacaaa gctattcgtc cagatgaggc cggactggta   12120
tacaacgctc tcttagaacg cgtggctcgc tacaacagta gcaatgtgca aaccaatttg   12180
gaccgtatga taacagatgt acgcgaagcc gtgtctcagc gcgaaaggtt ccagcgtgat   12240
gccaacctgg gttcgctggt ggcgttaaat gctttcttga gtactcagcc tgctaatgtg   12300
ccgcgtggtc aacaggatta tactaacttt ttaagtgctt tgagactgat ggtatcagaa   12360
gtacctcaga gcgaagtgta tcagtccggt cctgattact tctttcagac tagcagacag   12420
ggcttgcaga cggtaaatct gagccaagct tttaaaaacc tttaaaggtt tgtggggagt   12480
gcatgccccg gtaggagaaa gagcaaccgt gtctagcttg ttaactccga actcccgcct   12540
attattactg ttggtagctc cttcaccga cagcggtagc atcgaccgta ttcctatt     12600 gggttaccta ctaaacctgt atcgcgaagc cataggggcaa agtcaggtgg acgagcagac   12660
ctatcaagaa attacccaag tcagtcgcgc tttgggacag gaagacactg gcagtttgga   12720
agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca cgcgcaaata tggagcccag   12900
catgtatgcc agtaaccgac cttttcattaa caaactgctg gactacttgc acagagctgc   12960
cgctatgaac tctgattatt tcaccaatgc catcttaaac ccgcactggc tgcccccacc   13020
tggtttctac acgggcgaat atgacatgcc cgaccctaat gacggatttc tgtgggacga   13080
cgtggacagc gatgtttttt cacctctttc tgatcatcgc acgtggaaaa aggaaggcgg   13140
cgatagaatg cattcttctg catcgctgtc cggggtcatg ggtgctaccg cggctgagcc   13200
cgagtctgca gtcctttttc ctagtctacc cttttctcta cacagtgtac gtagcagcga   13260
agtgggtaga ataagtcgcc cgagtttaat gggcgaagag gagtatctaa acgattcctt   13320
gctcagaccg gcaagagaaa aaaatttccc aaacaatgga atagaaagtt tggtggataa   13380
aatgagtaga tggaagactt atgctcagga tcacagagac gagcctggga tcatggggat   13440
tacaagtaga gcgagcgcta gacgccagcc ccatgacaga cagaggggtc ttgtgtggga   13500
cgatgaggat tcggccgatg atagcagcgt gctggacttg ggtgggagag aagggggcaa   13560
cccgtttgct catttgcgcc ctcgcttggg tggtatgttg taaaaaaaaa taaaaaaaaa   13620
actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800
cctttgtgcc tccgcgatac ctggcaccta cggagggcag aaacagcatt cgttattcgg   13860
aactggcacc tcagtacgat accaccaggt tgtatctggt ggacaacaag tcggcggaca   13920
ttgcttctct gaactatcag aatgaccaca gcaacttctt gaccacggtg gtgcaaaaca   13980
```

```
atgactttac ccctacggaa gccagcaccc agaccattaa cttttgatgaa cgatcgcggt   14040 ggggcggtca gctaaagacc atcatgcata ctaacatgcc aaacgtgaac gagtatatgt   14100
ttagtaacaa gttcaaagcg cgtgtgatgg tgtccagaaa acctcccgac ggtgctgcag   14160
ttggggatac ttatgatcac aagcaggata ttttgaaata tgagtggttc gagtttactt   14220
tgccagaagg caacttttca gttactatga ctattgattt gatgaacaat gccatcatag   14280
ataattactt gaaagtgggt agacagaatg gagtgcttga aagtgacatt ggtgttaagt   14340
tcgacaccag gaacttcaag ctgggatggg atcccgaaac caagttgatc atgcctggag   14400
tgtatacgta tgaagccttc catcctgaca ttgtcttact gcctggctgc ggagtggatt   14460
ttaccgagag tcgtttgagc aaccttcttg gtatcagaaa aaaacagcca tttcaagagg   14520
gttttaagat tttgtatgaa gatttagaag gtggtaatat tccggccctc ttggatgtag   14580
atgcctatga gaacagtaag aaagaacaaa aagccaaaat agaagctgct acagctgctg   14640
cagaagctaa ggcaaacata gttgccagcg actctacaag ggttgctaac gctggagagg   14700
tcagaggaga caattttgcg ccaacacctg ttccgactgc agaatcatta ttggccgatg   14760
tgtctgaagg aacggacgtg aaactcacta ttcaacctgt agaaaagat agtaagaata   14820 gaagctataa tgtgttggaa gacaaaatca acacagccta tcgcagttgg tatctttcgt   14880
acaattatgg cgatcccgaa aaaggagtgc gttcctggac attgctcacc acctcagatg   14940
tcacctgcgg agcagagcag gtctactggt cgcttccaga catgatgaag gatcctgtca   15000
cttcccgctc cactagacaa gtcagtaact accctgtggt gggtgcagag cttatgcccg   15060
tcttctcaaa gagcttctac aacgaacaag ctgtgtactc ccagcagctc cgccagtcca   15120
cctcgcttac gcacgtcttc aaccgctttc ctgagaacca gattttaatc cgtccgccgg   15180
cgcccaccat taccaccgtc agtgaaaacg ttcctgctct cacagatcac gggaccctgc   15240
cgttgcgcag cagtatccgg ggagtccaac gtgtgaccgt tactgacgcc agacgccgca   15300
cctgtcccta cgtgtacaag gcactgggca tagtcgcacc gcgcgtcctt tcaagccgca   15360
ctttctaaaa aaaaaaaaaa tgtccattct tatctcgccc agtaataaca ccggttgggg   15420
tctgcgcgct ccaagcaaga tgtacggagg cgcacgcaaa cgttctaccc aacatcctgt   15480
ccgtgttcgc ggacatttc gcgctccatg gggcgccctc aagggccgca ctcgcgttcg   15540
aaccaccgtc gatgatgtaa tcgatcaggt ggttgccgac gcccgtaatt atactcctac   15600
tgcgcctaca tctactgtgg atgcagttat tgacagtgta gtggctgacg ctcgcaacta   15660
tgctcgacgt aagagccggc gaaggcgcat tgccagacgc caccgagcta ccactgccat   15720
gcgagccgca agagctctgc tacgaagagc tagacgcgtg gggcgaagag ccatgcttag   15780
ggcggccaga cgtgcagctt cgggcgccag cgccggcagg tcccgcaggc aagcagccgc   15840
tgtcgcagcg gcgactattg ccgacatggc ccaatcgcga agaggcaatg tatactgggt   15900
gcgtgacgct gccaccggtc aacgtgtacc cgtgcgcacc cgtcccctc gcacttagaa   15960 gatactgagc agtctccgat gttgtgtccc agcggcgagg atgtccaagc gcaaatacaa   16020
ggaagaaatg ctgcaggtta tcgcacctga agtctacggc caaccgttga aggatgaaaa   16080 aaacccgc aaatcaagc gggttaaaaa ggacaaaaaa gaagaggaag atggcgatga   16140
tgggctggcg gagtttgtgc gcgagtttgc cccacgcgca cgcgtgcaat ggcgtgggcg   16200
caaagttcga catgtgttga gacctggaac ttcggtggtc tttacacccg gcgagcgttc   16260
aagcgctact tttaagcgtt cctatgatga ggtgtacggg gatgatgata ttcttgagca   16320
ggcggctgac cgattaggcg agtttgctta tggcaagcgt agtagaataa cttccaagga   16380
```

```
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg ggggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gttttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aattttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaattttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaaccccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccggggggcg ctcctcgtcc  18060 aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
ttgcagaagg tgtaaaaaat acaactggtg aggaacacg aacagaagag gaaaccaata  18720
ctactactta cacttttggc aatgctcctg taaaagctga agctgaaatt acaaaagaag  18780
```

```
gactcccagt aggtttggaa gtttcagatg aagaaagtaa accgatttat gctgataaaa   18840
catatcagcc agaacctcag ctgggagatg aaacttggac tgaccttgat ggaaaaaccg   18900
aaaagtatgg aggcagggct ctcaaacccg atactaagat gaaaccatgc tacgggtcct   18960
ttgccaaacc tactaatgtg aaaggcggtc aggcaaaaca aaaacaacg gagcagccaa    19020 atcagaaagt cgaatatgat atcgacatgg agttttttga tgcggcatcg cagaaaacaa   19080
acttaagtcc taaaattgtc atgtatgcag aaaatgtaaa tttggaaact ccagacactc   19140
atgtagtgta caaacctgga acagaagaca caagttccga agctaatttg ggacaacaat   19200
ctatgcccaa cagacccaac tacattggct tcagagataa ctttattgga cttatgtact   19260
ataacagtac tggtaacatg ggggtgctgg ctggtcaagc gtctcagtta aatgcagtgg   19320
ttgacttgca ggacagaaac acagaacttt cttaccaact cttgcttgac tctctgggcg   19380
acagaaccag atactttagc atgtggaatc aggctgtgga cagttatgat cctgatgtac   19440
gtgttattga aaatcatggt gtggaagatg aacttcccaa ctactgtttt ccactggacg   19500
gcataggtgt tccaacaacc agttacaaat caatagttcc aaatggagac aatgcgccta   19560
attggaagga acctgaagta aatgaacaa gtgagatcgg acagggtaat ttgtttgcca     19620
tggaaattaa ccttcaagcc aatctatggc gaagtttcct ttattccaat gtggctctat   19680
atctcccaga ctcgtacaaa tacacccgt ccaatgtcac tcttccagaa acaaaaaca     19740 cctacgacta catgaacggg cgggtggtgc cgccatctct agtagacacc tatgtgaaca   19800
ttggtgccag gtggtctctg gatgccatgg acaatgtcaa cccattcaac caccaccgta   19860
acgctggctt gcgttaccga tccatgcttc tgggtaacgg acgttatgtg cctttccaca   19920
tacaagtgcc tcaaaaattc ttcgctgtta aaaacctgct gcttctccca ggctcctaca   19980
cttatgagtg gaactttagg aaggatgtga acatggttct acagagttcc ctcggtaacg   20040
acctgcgggt agatggcgcc agcatcagtt tcacgagcat caacctctat gctactttt    20100 tcccccatggc tcacaacacc gcttccaccc ttgaagccat gctgcggaat gacaccaatg   20160
atcagtcatt caacgactac ctatctgcag ctaacatgct ctaccccatt cctgccaatg   20220
caaccaatat tcccatttcc attccttctc gcaactgggc ggctttcaga ggctggtcat   20280
ttaccagact gaaaaccaaa gaaactccct ctttggggtc tggatttgac ccctactttg   20340
tctattctgg ttctattccc tacctggatg gtaccttcta cctgaccac acttttaaga    20400 aggtttccat catgtttgac tcttcagtga gctggcctgg aaatgacagg ttactatctc   20460
ctaacgaatt tgaaataaag cgcactgtgg atggcgaagg ctacaacgta gcccaatgca   20520
acatgaccaa agactggttc ttggtacaga tgctcgccaa ctacaacatc ggctatcagg   20580
gcttctacat tccagaagga tacaaagatc gcatgtattc attttcaga aacttccagc    20640 ccatgagcag gcaggtggtt gatgaggtca attacaaaga cttcaaggcc gtcgccatac   20700
cctaccaaca caacaactct ggctttgtgg gttacatggc tccgaccatg cgccaaggtc   20760
aaccctatcc cgctaactat ccctatccac tcattggaac aactgccgta aatagtgtta   20820
cgcagaaaaa gttcttgtgt gacagaacca tgtggcgcat accgttctcg agcaacttca   20880
tgtctatggg ggcccttaca gacttgggac agaatatgct ctatgccaac tcagctcatg   20940
ctctggacat gaccttgag gtggatccca tggatgagcc caccctgctt tatcttctct     21000
tcgaagtttt cgacgtggtc agagtgcatc agccacaccg cggcatcatc gaggcagtct   21060
acctgcgtac accgttctcg gccggtaacg ctaccacgta agaagcttct tgcttcttgc   21120
aaatagcagc tgcaaccatg gcctgcggat cccaaaacgg ctccagcgag caagagctca   21180
```

```
gagccattgt ccaagacctg ggttgcggac cctattttt gggaacctac gataagcgct    21240
tcccggggtt catggcccc gataagctcg cctgtgccat tgtaaatacg gccggacgtg    21300
agacgggggg agagcactgg ttggctttcg gttggaaccc acgttctaac acctgctacc    21360
tttttgatcc tttttggattc tcggatgatc gtctcaaaca gatttaccag tttgaatatg    21420
agggtctcct gcgccgcagc gctcttgcta ccaaggaccg ctgtattacg ctggaaaaat    21480
ctacccagac cgtgcagggt ccccgttctg ccgcctgcgg acttttctgc tgcatgttcc    21540
ttcacgcctt tgtgcactgg cctgaccgtc ccatggacgg aaaccccacc atgaaattgc    21600
taactggagt gccaaacaac atgcttcatt ctcctaaagt ccagcccacc ctgtgtgaca    21660
atcaaaaagc actctaccat tttcttaata cccattcgcc ttattttcgc tcccatcgta    21720
cacacatcga aagggccact gcgttcgacc gtatggatgt tcaataatga ctcatgtaaa    21780
caacgtgttc aataaacatc actttatttt tttacatgta tcaaggctct gcattactta    21840
tttatttaca agtcgaatgg gttctgacga gaatcagaat gacccgcagg cagtgatacg    21900
ttgcggaact gatacttggg ttgccacttg aattcgggaa tcaccaactt gggaaccggt    21960
atatcgggca ggatgtcact ccacagcttt ctggtcagct gcaaagctcc aagcaggtca    22020
ggagccgaaa tcttgaaatc acaattagga ccagtgcttt gagcgcgaga gttgcggtac    22080
accggattgc agcactgaaa caccatcagc gacggatgtc tcacgcttgc cagcacggtg    22140
ggatctgcaa tcatgcccac atccagatct tcagcattgg caatgctgaa cggggtcatc    22200
ttgcaggtct gcctacccat ggcgggcacc caattaggct tgtggttgca atcgcagtgc    22260
aggggatca gtatcatctt ggcctgatcc tgtctgattc ctggatacac ggctctcatg    22320
aaagcatcat attgcttgaa agcctgctgg gctttactac cctcggtata aacatcccg    22380
caggacctgc tcgaaaactg gttagctgca cagccggcat cattcacaca gcagcgggcg    22440
tcattgttag ctatttgcac cacacttctg ccccagcggt tttgggtgat tttggttcgc    22500
tcgggattct cctttaaggc tcgttgtccg ttctcgctgg ccacatccat ctcgataatc    22560
tgctccttct gaatcataat attgccatgc aggcacttca gcttgccctc ataatcattg    22620
cagccatgag gccacaacgc acagcctgta cattcccaat tatggtgggc gatctgagaa    22680
aaagaatgta tcattccctg cagaaatctt cccatcatcg tgctcagtgt cttgtgacta    22740
gtgaaagtta actggatgcc tcggtgctcc tcgtttacgt actggtgaca gatgcgcttg    22800
tattgttcgt gttgctcagg cattagttta aaagaggttc taagttcgtt atccagcctg    22860
tacttctcca tcagcagaca catcacttcc atgcctttct cccaagcaga caccaggggc    22920
aagctaatcg gattcttaac agtgcaggca gcagctcctt tagccagagg gtcatcttta    22980
gcgatcttct caatgcttct tttgccatcc ttctcaacga tgcgcacggg cgggtagctg    23040
aaacccactg ctacaagttg cgcctcttct ctttcttctt cgctgtcttg actgatgtct    23100
tgcatgggga tatgtttggt cttccttggc ttcttttgg ggggtatcgg aggaggagga    23160
ctgtcgctcc gttccggaga cagggaggat tgtgacgttt cgctcaccat taccaactga    23220
ctgtcggtag aagaacctga ccccacacgg cgacaggtgt ttctcttcgg gggcagaggt    23280
ggaggcgatt gcgaagggct gcggtccgac ctggaaggcg gatgactgg agaaccccctt    23340
ccgcgttcgg gggtgtgctc cctgtggcgg tgcttaact gatttccttc gcggctggcc    23400
attgtgttct cctaggcaga gaaacaacag acatggaaac tcagccattg ctgtcaacat    23460
cgccacgagt gccatcacat ctcgtcctca gcgacgagga aaaggagcag agcttaagca    23520
ttccaccgcc cagtcctgcc accacctcta ccctagaaga taaggaggtc gacgcatctc    23580
```

```
atgacatgca gaataaaaaa gcgaaagagt ctgagacaga catcgagcaa gacccgggct   23640
atgtgacacc ggtggaacac gaggaagagt tgaaacgctt tctagagaga gaggatgaaa   23700
actgcccaaa acaacgagca gataactatc accaagatgc tggaaatagg gatcagaaca   23760
ccgactacct catagggctt gacggggaag acgcgctcct taaacatcta gcaagacagt   23820
cgctcatagt caaggatgca ttattggaca gaactgaagt gcccatcagt gtggaagagc   23880
tcagccgcgc ctacgagctt aacctctttt cacctcgtac tcccccaaa cgtcagccaa    23940 acggcacctg cgagccaaat cctcgcttaa acttttatcc agcttttgct gtgccagaag   24000
tactggctac ctatcacatc ttttttaaaa atcaaaaaat tccagtctcc tgccgcgcta   24060
atcgcacccg cgccgatgcc ctactcaatc tgggacctgg ttcacgctta cctgatatag   24120
cttccttgga agaggttcca aagatcttcg agggtctggg caataatgag actcgggccg   24180
caaatgctct gcaaaaggga gaaaatggca tggatgagca tcacagcgtt ctggtggaat   24240
tggaaggcga taatgccaga ctcgcagtac tcaagcgaag catcgaggtc acacacttcg   24300
catatcccgc tgtcaacctg cccctaaag tcatgacggc ggtcatggac cagttactca    24360
ttaagcgcgc aagtccccctt tcagaagaca tgcatgaccc agatgcctgt gatgagggta   24420
aaccagtggt cagtgatgag cagctaaccc gatggctggg caccgactct cccagggatt   24480
tggaagagcg tcgcaagctt atgatggccg tggtgctggt taccgtagaa ctagagtgtc   24540
tccgacgttt ctttaccgat tcagaaacct tgcgcaaact cgaagagaat ctgcactaca   24600
cttttagaca cggctttgtg cggcaggcat gcaagatatc taacgtggaa ctcaccaacc   24660
tggtttccta catgggtatt ctgcatgaga atcgcctagg acaaagcgtg ctgcacagca   24720
ccctgaaggg ggaagcccgc cgtgattaca tccgcgattg tgtctatctg tacctgtgcc   24780
acacgtggca aaccggcatg ggtgtatggc agcaatgttt agaagaacag aacttgaaag   24840
agcttgacaa gctcttacag aaatctctta aggttctgtg gacagggttc gacgagcgca   24900
ccgtcgcttc cgacctggca gacctcatct tcccagagcg tctcagggtt actttgcgaa   24960
acggattgcc tgactttatg agccagagca tgcttaacaa ttttcgctct ttcatcctgg   25020
aacgctccgg tatcctgccc gccacctgct gcgcactgcc ctccgacttt gtgcctctca   25080
cctaccgcga gtgcccccg ccgctatgga gtcactgcta cctgttccgt ctggccaact    25140
atctctccta ccactcggat gtgatcgagg atgtgagcgg agacggcttg ctggagtgtc   25200
actgccgctg caatctgtgc acgcccacc ggtccctagc ttgcaacccc cagttgatga    25260
gcgaaaccca gataataggc acctttgaat tgcaaggccc cagcagccaa ggcgatgggt   25320
cttctcctgg gcaaagttta aaactgaccc cgggactgtg gacctccgcc tacttgcgca   25380
agtttgctcc ggaagattac caccctatg aaatcaagtt ctatgaggac caatcacagc    25440
ctccaaaggc cgaactttcg gcctgcgtca tcacccaggg ggcaattctg gcccaattgc   25500
aagccatcca aaaatcccgc caagaatttc tactgaaaaa gggtaagggg gtctaccttg   25560 accccccagac cggcgaggaa ctcaacacaa ggttccctca ggatgtccca acgacgagaa   25620
aacaagaagt tgaaggtgca gccgccgccc ccagaagata tggaggaaga ttgggacagt   25680
caggcagagg aggcggagga ggacagtctg gaggacagtc tggaggaaga cagtttggag   25740
gaggaaaacg aggaggcaga ggaggtgaa gaagtaaccg ccgacaaaca gttatcctcg    25800 gctgcgggaga caagcaacag cgctaccatc tccgctccga gtcgaggaac ccggcggcgt   25860
cccagcagta gatgggacga gaccggacgc ttcccgaacc caaccagcgc ttccaagacc   25920
ggtaagaagg atcggcaggg atacaagtcc tggcgggggc ataagaatgc catcatctcc   25980
```

```
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgcccgcc  26700 aacaccttaa tcccagaaat tggcccgccg ccctagtgta ccaggaaagt cccgctccca  26760
ccactgtatt acttcctcga gacgccagg ccgaagtcca aatgactaat gcaggtgcg  26820 agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120 attaccccgga cgagttcata ccgaacttcg acgcgattag cgagtcagtg gacggctacg  27180
attgatgtct ggtgacgcgg ctgagctatc tcggctgcga catctagacc actgccgccg  27240
cttccgctgc tttgcccggg aactcattga gttcatctac ttcgaactcc caaggatca  27300 ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaactttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aaccctggg  27720 tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaaccccca tagttatcac ccagcaaagt ggagatacta aggggttgcat  28080 tcactgctcc tgcgattcca tcgagtgcac ctacaccctg ctgaagaccc tatgcggcct  28140
aagagacctc taccaatga attaaaaaat gattaataaa aaatcactta cttgaaatca  28200
gcaataaggt ctctgttgaa attttctccc agcagcacct cacttccctc ttcccaactc  28260
tggtattcta aaccccgttc agcggcatac tttctccata ctttaaaggg gatgtcaaat  28320
tttagctcct ctcctgtacc cacaatcttc atgtctttct tcccagatga ccaagagagt  28380
```

```
ccggctcagt gactccttca accctgtcta cccctatgaa gatgaaagca cctcccaaca    28440
cccctttata aacccagggt ttatttcccc aaatggcttc acacaaagcc caaacggagt    28500
tcttacttta aaatgtttaa ccccactaac aaccacaggc ggatctctac agctaaaagt    28560
gggaggggga cttacagtgg atgacaccaa cggttttttg aaagaaaaca taagtgccac    28620
cacaccactc gttaagactg gtcactctat aggtttacca ctaggagccg gattgggaac    28680
gaatgaaaat aaactttgta tcaaattagg acaaggactt acattcaatt caaacaacat    28740
ttgcattgat gacaatatta acaccttatg gacaggagtc aaccccaccg aagccaactg    28800
tcaaatcatg aactccagtg aatctaatga ttgcaaatta attctaacac tagttaaaac    28860
tggagcacta gtcactgcat ttgtttatgt tataggagta tctaacaatt ttaatatgct    28920
aactacacac agaaatataa attttactgc agagctgttt ttcgattcta ctggtaattt    28980
actaactaga ctctcatccc tcaaaactcc acttaatcat aaatcaggac aaaacatggc    29040
tactggtgcc attactaatg ctaaaggttt catgcccagc acgactgcct atcctttcaa    29100
tgataattct agagaaaaag aaaactacat ttacggaact tgttactaca cagctagtga    29160
tcgcactgct tttcccattg acatatctgt catgcttaac cgaagagcaa taaatgacga    29220
gacatcatat tgtattcgta aacttggtc ctggaacaca ggagatgccc cagaggtgca    29280
aacctctgct acaaccctag tcacctcccc atttaccttt tactcatca gagaagacga    29340 ctgacaaata aagtttaact tgtttatttg aaaatcaatt cacaaaatcc gagtagttat    29400
tttgcctccc ccttcccatt taacagaata caccaatctc tccccacgca cagctttaaa    29460
catttggata ccattagata tagacatggt tttagattcc acattccaaa cagtttcaga    29520
gcgagccaat ctggggtcag tgatagataa aaatccatcg ggatagtctt ttaaagcgct    29580
ttcacagtcc aactgctgcg gatgcgactc cggagtctgg atcacggtca tctggaagaa    29640
gaacgatggg aatcataatc cgaaaacggt atcggacgat tgtgtctcat caaacccaca    29700
agcagccgct gtctgcgtcg ctccgtgcga ctgctgttta tgggatcagg gtccacagtg    29760
tcctgaagca tgatttaat agcccttaac atcaactttc tggtgcgatg cgcgcagcaa    29820
cgcattctga tttcactcaa atctttgcag taggtacaac acattattac aatattgttt    29880
aataaaccat aattaaaagc gctccagcca aaactcatat ctgatataat cgcccctgca    29940
tgaccatcat accaaagttt aatataaatt aaatgacgtt ccctcaaaaa cacactaccc    30000
acatacatga tctcttttgg catgtgcata ttaacaatct gtctgtacca tggacaacgt    30060
tggttaatca tgcaacccaa tataaccttc cggaaccaca ctgccaacac cgctcccca    30120 gccatgcatt gaagtgaacc ctgctgatta caatgacaat gaagaaccca attctctcga    30180
ccgtgaatca cttgagaatg aaaaatatct atagtggcac aacatagaca taaatgcatg    30240
catcttctca taattttaa ctcctcagga tttagaaaca tatcccaggg aataggaagc    30300
tcttgcagaa cagtaaagct ggcagaacaa ggaagaccac gaacacaact tacactatgc    30360
atagtcatag tatcacaatc tggcaacagc gggtggtctt cagtcataga agctcgggtt    30420
tcattttcct cacaacgtgg taactgggct ctggtgtaag ggtgatgtct ggcgcatgat    30480
gtcgagcgtg cgcgcaacct tgtcataatg gagttgcttc ctgacattct cgtattttgt    30540
atagcaaaac gcggccctgg cagaacacac tcttcttcgc cttctatcct gccgcttagc    30600
gtgttccgtg tgatagttca agtacaacca cactcttaag ttggtcaaaa gaatgctggc    30660
ttcagttgta atcaaaactc catcgcatct aatcgttctg aggaaatcat ccaagcaatg    30720
caactggatt gtgtttcaag caggagagga gagggaagag acggaagaac catgttaatt    30780
```

```
tttattccaa acgatctcgc agtacttcaa attgtagatc gcgcagatgg catctctcgc    30840
ccccactgtg ttggtgaaaa agcacagcta gatcaaaaga aatgcgattt tcaaggtgct    30900
caacggtggc ttccagcaaa gcctccacgc gcacatccaa gaacaaaaga ataccaaaag    30960
aaggagcatt ttctaactcc tcaatcatca tattacattc ctgcaccatt cccagataat    31020
tttcagcttt ccagccttga attattcgtg tcagttcttg tggtaaatcc aatccacaca    31080
ttacaaacag gtcccggagg gcgccctcca ccaccattct taaacacacc ctcataatga    31140
caaaatatct tgctcctgtg tcacctgtag cgaattgaga atggcaacat caattgacat    31200
gcccttggct ctaagttctt ctttaagttc tagttgtaaa aactctctca tattatcacc    31260
aaactgctta gccagaagcc ccccgggaac aagagcaggg gacgctacag tgcagtacaa    31320
gcgcagacct ccccaattgg ctccagcaaa aacaagattg gaataagcat attgggaacc    31380
gccagtaata tcatcgaagt tgctggaaat ataatcaggc agagtttctt gtaaaaattg    31440
aataaaagaa aaatttgcca aaaaaacatt caaaacctct gggatgcaaa tgcaataggt    31500
taccgcgctg cgctccaaca ttgttagttt tgaattagtc tgcaaaaata aaaaaaaaaa    31560
caagcgtcat atcatagtag cctgacgaac agatggataa atcagtcttt ccatcacaag    31620
acaagccaca gggtctccag ctcgaccctc gtaaaacctg tcatcatgat taaacaacag    31680
caccgaaagt tcctcgcggt gaccagcatg aataattctt gatgaagcat acaatccaga    31740
catgttagca tcagttaacg agaaaaaaca gccaacatag cctttgggta taattatgct    31800
taatcgtaag tatagcaaag ccaccccctcg cggatacaaa gtaaaaggca caggagaata    31860
aaaaatataa ttatttctct gctgctgttc aggcaacgtc gccccggtc cctctaaata    31920 cacatacaaa gcctcatcag ccatggctta ccagacaaag tacagcgggc acacaaagca    31980
caagctctaa agtgactctc caacctctcc acaatatata tatacacaag ccctaaactg    32040
acgtaatggg agtaaagtgt aaaaaatccc gccaaaccca acacacaccc cgaaactgcg    32100
tcaccaggga aaagtacagt ttcacttccg caatcccaac aggcgtaact tcctctttct    32160
cacggtacgt gatatcccac taacttgcaa cgtcattttc ccacggtcgc accgcccctt    32220
ttagccgtta accccacagc caatcaccac acgatccaca cttttttaaaa tcacctcatt    32280 tacatattgg caccattcca tctataaggt atattatata gatag                    32325
```

<210> SEQ ID NO 4
<211> LENGTH: 35345
<212> TYPE: DNA
<213> ORGANISM: adenovirus

<400> SEQUENCE: 4

```
ctatctatat aatataccct atagatggaa tggtgccaac atgtaaatga ggtaatttaa      60
aaaagtgcgc gctgtgtggt gattggctgc ggggttaacg gctaaaaggg gcggcgcgac     120
cgtgggaaaa tgacgtgact tatgtgggag gagttatgtt gcaagttatt acggtaaatg     180
tgacgtaaaa cgaggtgtgg tttgaacacg gaagtagaca gttttcccac gcttactgac     240
aggatatgag gtagttttgg gcggatgcaa gtgaaaattc tccattttcg cgcgaaaact     300
aaatgaggaa gtgaatttct gagtcatttc gcggttatgc cagggtggag tatttgccga     360
gggccgagta gactttgacc gtttacgtgg aggtttcgat taccgtgttt ttcacctaaa     420 ttttccgcgta cggtgtcaaa gttctgtgtt tttacgtagg tgtcagctga tcgctagggt     480
atttaaacct gacgagttcc gtcaagaggc cactcttgag tgccagcgag aagagttttc     540
tcctccgcgc cgcaagtcag ttctgcgctt tgaaaatgag acacctgcgc ttcctgccac     600
```

```
aggaggttat ctccagtgag accgggatcg aaatactgga gtttgtggta aatacccctaa    660
tgggagacga cccggaaccg ccagtgcagc ctttcgatcc acctacgctg cacgatctgt    720
atgatttaga gatagacggg ccggaggatc ccaatgagga agctgtgaat gggtttttta    780
ctgattctat gctgctagct gctgatgaag gattggacat aaaccctcct cctgagacac    840
ttgttacccc aggggtggtt gtggaaagcg gcataggtgg gaaaaaattg cctgatctgg    900
gagcagctga aatggacttg cgttgttatg aagagggttt tcctcccagt gatgatgaag    960
atggggaaac tgagcagtcc atccataccg cagtaaatga gggagtaaaa gctgccagcg   1020
atgtttttaa gttggactgt ccggagctgc ctggacatgg ctgtaagtct tgtgaatttc   1080
acaggaataa cactggaatg aaagaactat tgtgctcgct ttgctatatg agaatgcact   1140
gccactttat ttacagtaag tgtatttaag tgaaatttaa aggaatagtg tagctattta   1200
ataactgttg aatggtagat ttatgttttt ttcttgcgat tttttgtagg tcctgtgtct   1260
gatgatgagt caccttctcc tgattcaact acctcacctc ctgaaattca ggcgcccgca   1320
cctgcaaacg tatgcaagcc cattcctgtg aagcctaagc ctgggaaacg ccctgctgtg   1380
gataagcttg aggacttgtt ggagggtggg gatggacctt tggaccttag tacccggaaa   1440
ctgccaaggc aatgagtgcc ctgcagctgt gtttatttaa tgtgacgtca tgtaataaaa   1500
ttatgtcagc tgctgagtgt tttattactt cttgggtggg gacttggata tataagtagg   1560
agcagatctg tgtggttagc tcacagcaac ctgctgccat ccatggaggt ttgggctatc   1620
ttggaagacc tcagacagac taagctactg ctagaaaacg cctcggacgg agtctctggc   1680
ctttggagat tctggttcgg tggtgatcta gctaggctag tgtttaggat aaaacaggac   1740
tacagggaag aatttgaaaa gttattggac gatagtccgg gactttttga agctcttaac   1800
ttgggtcatc aggctcattt taaggagaag gttttatcag ttttagattt ttctactcct   1860
ggtagaactg ctgctgctgt agcttttctt acttттtatat tggataaatg gatccgccaa   1920
actcacttca gcaagggata cgttttggat ttcatagcag cagctttgtg gagaacatgg   1980
aaggctcgca ggatgaggac aatcttagat tactggccag tgcagcctct gggagtagca   2040
gggatactga gacacccacc gaccatgcca gcggttctgc aggaggagca gcaggaggac   2100
aatccgagag ccggcctgga ccctccggtg gaggagtagc tgacctgttt cctgaactgc   2160
gacgggtgct tactaggtct acgaccagtg gacagaacag gggaattaag agggagagga   2220
atcctagtgg gaataattca agaaccgagt tggctttaag tttaatgagc cgcaggcgtc   2280
ctgaaactgt ttggtggcat gaggttcaga gcgaaggcag ggatgaagtt tcaatattgc   2340
aggagaaata ttcactagaa caacttaaga cctgttggtt ggaacctgag gatgattggg   2400
aggtggccat taggaattat gctaagatat ctctgaggcc tgataaacaa tatagaatta   2460
ctaagaagat taatattaga aatgcatgct acatatcagg gaatgggca gaggttataa   2520
tagatacaca agataaagca gtttttagat gttgtatgat gggtatgtgg ccaggggttg   2580
tcggcatgga agcagtaaca cttatgaata ttaggtttaa agggggatgg tataatggca   2640
ttgtatttat ggctaacact aagctgattc tacatggttg tagctttttt gggtttaata   2700
atacgtgtgt agaagcttgg gggcaagtta gtgtgagggg ttgtagtttt tatgcatgct   2760
ggattgcaac atcaggtagg gtcaagagtc agttgtctgt gaagaaatgc atgtttgaga   2820
gatgtaatct tggcatactg aatgaaggtg aagcaagggt ccgccactgc gcagctacag   2880
aaactggctg cttcattcta ataaagggaa atgccagtgt gaagcataat atgatctgtg   2940
gacattcgga tgagaggcct tatcagatgc tgacctgcgc tggtggacat tgcaatattc   3000
```

```
ttgctaccgt gcatatcgtt tcacatgcac gcaaaaaatg gcctgtattt gaacataatg    3060
tgattaccaa gtgcaccatg cacataggtg gtcgcagggg aatgtttatg ccttaccagt    3120
gtaacatgaa tcatgtgaag gtaatgttgg aaccagatgc cttttccaga gtgagcttaa    3180
caggaatctt tgatatgaat attcaactat ggaagatcct gagatatgat gacactaaac    3240
caagggtgcg cgcatgcgaa tgcggaggca agcatgctag attccagccg gtgtgcgtgg    3300
atgtgactga agacttgaga cccgatcatt tggtgcttgc ctgcactgga gcggagttcg    3360
gttctagtgg tgaagaaact gactaaagtg agtagtgggg caagatgtgg atggggactt    3420
tcaggttggt aaggtgggca gattgggtaa attttgttaa tttctgtctt gcagctgcca    3480
tgagtggaag cgcttctttt gaggggggag tatttagccc ttatctgacg ggcaggctcc    3540
caccatgggc aggagttcgt cagaatgtca tgggatccac tgtggatggg agaccgtcc    3600
agcccgccaa ttcctcaacg ctgacctatg ccactttgag ttcgtcacca ttggatgcag    3660
ctgcagccgc cgccgctact gctgccgcca acaccatcct tggaatgggc tattatggaa    3720
gcatcgttgc caattccagt tcctctaata acccttcaac cctggctgag acaagctac    3780
ttgttctctt ggcgcagctc gaggccttaa cccaacgctt aggcgaactg tctaagcagg    3840
tggcccagtt gcgtgagcaa actgagtctg ctgttgccac agcaaagtct aaataaagat    3900
ctcaaatcaa taaataaaga aatacttgat ataaacaaa tgaatgttta tttgattttt    3960
cgcgcgcggt atgccctgga ccatcggtct cgatcattga gaacgcggtg gatcttttcc    4020
agtaccctgt aaaggtggga ttgaatgttt agatacatgg gcattagtcc gtctcggggg    4080
tggagatagc tccattgaag agcctcttgc tccggggtag tgttataaat cacccagtca    4140
tagcaaggtc ggagtgcatg gtgttgcaca atatcttta ggagcagact aattgcaacg    4200
gggaggccct tagtgtaggt gtttacaaat ctgttgagct gggacgggtg catccgggt    4260
gaaattatat gcattttgga ctggatcttg aggttgcaa tgttgccgcc tagatcccgt    4320
ctcgggttca tattgtgcag gaccaccaag acagtgtatc cggtgcactt gggaaattta    4380
tcatgcagct tagagggaaa agcatgaaaa aatttggaga cgcctttgtg accccccaga    4440
ttctccatgc actcatccat aatgatagcg atggggccgt gggcagcggc acgggcgaac    4500
acgttccggg ggtctgaaac atcatagtta tgctcctgag tcaggtcatc ataagccatt    4560
ttaataaact ttgggcggag ggtgccagat tgggggatga agttccctc tggcccggga    4620
gcatagtttc cctcacatat ttgcatttcc caggctttca gttcagaggg ggggatcatg    4680
tccacctgcg gggctataaa aaataccgtt tctggagccg gggtgattaa ctgggacgag    4740
agcaaattcc taagcagctg agacttgccg cacccagtgg gaccgtaaat gaccccaatt    4800
acgggttgca gatggtagtt tagggaacga cagctgccgt cctcccggag cagggggccc    4860
acttcgttca tcatttccct tacatggata ttttcccgca ccaagtccgt taggaggcgc    4920
tctcccccaa gggatagaag ctcctggagc gaggagaagt ttttcagcgg cttcagcccg    4980
tcagccatgg gcattttgga aagagtctgt tgcaagagct cgagccggtc ccagagctcg    5040
gtgatgtgct ctatggcatc tcgatccagc agacctcctc gttcgcgggg ttgggacggc    5100
tcctggagta gggaatcaga cgatgggcgt ccagcgctgc cagggtccga tccttccatg    5160
gtcgcagcgt ccgagtcagg gttgtttccg tcacggtgaa ggggtgcgcg cctggttggg    5220
cgcttgcgag ggtgcgcttc agactcatcc tgctggtcga gaaccgctgc cgattggcgc    5280
cctgcatgtc ggccaggtag cagtttacca tgagttcgta gttgagcgcc tcggccgcgt    5340
ggcctttggc acggagctta cctttggaag ttttatggca ggcggggcag tagatacatt    5400
```

```
tgagggcata caacttgggc gcgaggaaaa tggattcggg ggagtatgca tccgcaccgc   5460
aggaggcgca gacggtttcg cactccacga gccaggtcag atccggctca tcgggtcaa    5520 aaacaagttt tccgccatgt tttttgatgc gtttcttacc tttggtttcc atgagttcgt   5580
gtccccgctg ggtgacaaag aggctgtccg tgtccccgta gaccgacttt atgggcctgt   5640
cctcgagcgg agtgcctcgg tcctcttcgt agaggaaccc agcccactct gatacaaaag   5700
cgcgtgtcca ggccagcaca aaggaggcca cgtgggaggg gtagcggtcg ttgtcaacca   5760
gggggtccac cttctctacg gtatgtaaac acatgtcccc ctcctccaca tccaagaatg   5820
tgattggctt gtaagtgtag gccacgtgac caggggtccc cgccgggggg gtataaaagg   5880
gggcgggcct ctgttcgtcc tcactgtctt ccggatcgct gtccaggagc gccagctgtt   5940
ggggtaggta ttccctctcg aaggcgggca tgacctctgc actcaggttg tcagtttcta   6000
ggaacgagga ggatttgata ttgacagtac cagcagagat gcctttcata agactctcgt   6060
ccatctggtc agaaaacaca atcttcttgt tgtccagctt ggtggcaaat gatccataga   6120
gggcattgga tagaagcttg gcgatggagc gcatggtttg gttcttttcc ttgtccgcgc   6180
gctccttggc ggtgatgtta agctggacgt actcgcgcgc cacacatttc cattcaggaa   6240
agatggttgt cagttcatcc ggaactattc tgattcgcca tccctattg tgcagggtta    6300 tcagatccac actggtggcc acctcgcctc ggaggggctc attggtccag cagagtcgac   6360
ctccttttct tgaacagaaa gggggagggg ggtctagcat gaactcatca gggggtccg    6420 catctatggt aaatattccc ggtagcaaat ctttgtcaaa atagctgatg gtggcgggat   6480
catccaaggt catctgccat tctcgaactg ccagcgcgcg ctcatagggg ttaagagggg   6540
tgccccaggg catggggtgg gtgagcgcgg aggcatacat gccacagata tcgtagacat   6600 agagggctc ttcgaggatg ccgatgtaag tgggataaca tcgccccct ctgatgcttg      6660 ctcgcacata gtcatagagt tcatgtgagg gggcaagaag acccgggccc agattggtgc   6720
ggttgggttt ttccgccctg taaacgatct ggcgaaagat ggcatgggaa ttggaagaga   6780
tagtaggtct ctggaatatg ttaaaatggg catgaggtaa gcctacagag tcccttatga   6840
agtgggcata tgactcttgc agcttggcta ccagctcggc ggtgatgagt acatccaggg   6900
cacagtagtc gagagtttcc tggatgatgt cataacgcgg ttggcttttc ttttcccaca   6960
gctcgcggtt gagaaggtat tcttcgtgat ccttccagta ctcttcgagg ggaaacccgt   7020
cttttcctgc acggtaagag cccaacatgt agaactgatt gactgccttg tagggacagc   7080
atcccttctc cactgggaga gagtatgctt gggctgcatt gcgcagcgag gtatgagtga   7140
gggcaaaagt gtccctgacc atgactttga ggaattgata cttgaagtcg atgtcatcac   7200 aggcccctg ttcccagagt tggaagtcca cccgcttctt gtaggcgggg ttgggcaaag    7260
cgaaagtaac atcattgaag aggatcttgc cggccctggg catgaaattt cgggtgattt   7320
tgaaaggctg aggaacctct gctcggttat tgataacctg agcggccaag acgatctcat   7380
caaagccatt gatgttgtgc cccactatgt acagttctaa gaatcgaggg gtgcccctga   7440
catgaggcag cttcttgagt tcttcaaaag tgagatctgt agggtcagtg agagcatagt   7500
gttcgagggc ccattcgtgc acgtgagggt tcgctttaag gaaggaggac cagaggtcca   7560
ctgccagtgc tgtttgtaac tggtcccggt actgacgaaa atgctgtccg actgccatct   7620
tttctggggt gacgcaatag aaggtttggg ggtcctgccg ccagcgatcc cacttgagtt   7680
ttatggcgag gtcataggcg atgttgacga gccgctggtc tccagagagt ttcatgacca   7740
gcatgaaggg gattagctgc ttgccaaagg accccatcca ggtgtaggtt tccacatcgt   7800
```

```
aggtgagaaa gagcctttct gtgcgaggat gagagccaat cgggaagaac tggatctcct   7860
gccaccagtt ggaggaatgg ctgttgatgt gatggaagta gaactccctg cgacgcgccg   7920
agcattcatg cttgtgcttg tacagacggc cgcagtactc gcagcgattc acgggatgca   7980
ccttatgaat gagttgtacc tgacttcctt tgacgagaaa tttcagtgga aaattgaggc   8040
ctggcgcttg tacctcgcgc tttactatgt tgtctgcatc ggcatgacca tcttctgtct   8100
cgatggtggt catgctgacg agccctcgcg ggaggcaagt ccagacctcg gcgcggcagg   8160
ggcggagctc gaggacgaga gcgcgcaggc cggagctgtc cagggtcctg agacgctgcg   8220
gagtcaggtt agtaggcagt gtcaggagat taacttgcat gatcttttgg agggcgtgag   8280
ggaggttcag atagtacttg atctcaacgg gtccgttggt ggagatgtcg atggcttgca   8340
gggttccgtg tcccttgggc gctaccaccg tgcccttgtt tttcattttg gacggcggtg   8400
gctctgttgc ttcttgcatg tttagaagcg gtgtcgaggg cgcgcaccgg gcggcagggg   8460
cggctcggga cccggcggca tggctggcag tggtacgtcg gcgccgcgcg cgggtaggtt   8520
ctggtactgc gccctgagaa gactcgcatg cgcgacgacg cggcggttga catcctggat   8580
ctgacgcctc tgggtgaaag ctaccggccc cgtgagcttg aacctgaaag agagttcaac   8640
agaatcaatc tcggtatcgt tgacggcggc ttgcctaagg atttcttgca cgtcgccaga   8700
gttgtcctgg taggcgatct cggccatgaa ctgctcgatc tcttcctctt gaagatctcc   8760
gcggcccgct ctctcgacgg tggccgcgag gtcgttggag atgcgcccaa tgagttgaga   8820
gaatgcattc atgcccgcct cgttccagac gcggctgtag accacagccc ccacgggatc   8880
tctcgcgcgc atgaccacct gggcgaggtt gagctccacg tggcgggtga agaccgcata   8940
gttgcatagg cgctggaaaa ggtagttgag tgtggtggcg atgtgctcgg tgacgaagaa   9000
atacatgatc catcgtctca gcggcatctc gctgacatcg cccagcgctt ccaagcgctc   9060
catggcctcg tagaagtcca cggcaaagtt aaaaaactgg gagttacgcg cggacacggt   9120
caactcctct tccagaagac ggataagttc ggcgatggtg gtgcgcacct cgcgctcgaa   9180
agccctgggg attcttcct caatctcttc ttcttccact aacatctctt cctcttcagg   9240
tggggctgca ggaggagggg gaacgcggcg acgccggcgg cgcacgggca gacggtcgat   9300
gaatctttca atgacctctc cgcggcgcgc gcgcatggtc tcggtgacgg cacgaccgtt   9360
ctccctgggt ctcagagtga agacgcctcc gcgcatctcc ctgaagtggt gactgggagg   9420
ctctccgttg ggcagggaca ccgcgctgat tatgcatttt atcaattgcc ccgtaggtac   9480
tccgcgcaag gacctgatcg tctcaagatc cacgggatct gaaaacctt cgacgaaagc   9540 gtctaaccag tcgcaatcgc aaggtaggct gagcactgtt tcttgcgggc ggggcggct   9600 agacgctcgg tcggggttct ctctttcttc tccttcctcc tcttgggagg gtgagacgat   9660
gctgctggtg atgaaattaa aataggcagt tttgagacgg cggatggtgg cgaggagcac   9720
caggtctttg ggtccggctt gttggatacg caggcgatga gccattcccc aagcattatc   9780
ctgacatctg gccagatctt tatagtagtc ttgcatgagt cgttccacgg gcacttcttc   9840
ttcgcccgct ctgccatgca tgcgagtgat cccgaacccg cgcatgggct ggacaagtgc   9900
caggtccgct acaaccctt cggcgaggat ggcttgctgc acctgggtga gggtggcttg   9960
gaagtcgtca aagtccacga agcggtggta ggccccggtt ttgattgtgt aggagcagtt   10020
ggccatgact gaccagttga ctgtctggtg cccagggcgc acgagctcgg tgtacttgag   10080
gcgcgagtat gcgcgggtgt caagatgta atcgttgcag gtgcgcacca ggtactggta   10140
gccaatgaga aagtgtggcg gtggctggcg gtacaggggc catcgctctg tagccggggc   10200
```

```
tccgggggcg aggtcttcca gcatgaggcg gtggtagccg tagatgtacc tggacatcca   10260
ggtgataccg gaggcggtgg tggatgcacg tgggaactcg cgcacgcggt tccagatgtt   10320
gcgcagcggc atgaagtagt tcatggtagg cacggtctgg ccagtgaggc gcgcgcagtc   10380
attgacgctc tgtagacacg gagaaaacga aagcgatgag cggctcgact ccgtggtctg   10440
ggggaacgtg aacgggttgg gtcgcggtgt accccggttc gagtccaaag ctaagcgatc   10500
acgctcggat cggccggagc cgcggctaac gtggtattgg ctatcccgtc tcgacccagc   10560
cgacgaatat ccagggtacg gagtagagtc gttttttgctg cttttttcctg gacgtgtgcc   10620 attgccacgt caagctttag aacgctcagt tctcgggccg tgagtggctc gcgcccgtag   10680
tctggagaat cagtcgccag ggttgcgttg cggtatgccc cggttggagc ctaagcgcgg   10740
ctcgtatcgg ccggtttccg cgacaagcga gggtttggca gccccgttat ttccaagacc   10800
ccgccagccg acttctccag tttacgggag cgagcccttt tttttttttt tttgtttttg   10860
tcgcccagat gcatccagtg ctgcgacaga tgcgccccca gcaacaggcc ccttctcagc   10920
aacagccaca aaaggctctt cttgctcctg caactactgc agctgcagcc gtgagcggcg   10980
cgggacagcc cgcctatgat ctggacttgg aagagggcga gggattggcg cgcctggggg   11040
ctccatcgcc cgagcggcac ccgcgggtgc aactaaaaaa ggactctcgc gaggcgtacg   11100
tgccccagca gaacctgttc agggacagga gcggcgagga gccagaggag atgcgagcat   11160
ctcgatttaa cgcgggtcgc gagctgcgcc acggtctgga tcgaagacgg gtgctgcaag   11220
acgaggattt tgaggtcgat gaagtcacag ggatcagccc agctagggca catgtggccg   11280
cggccaacct agtctcggcc tacgagcaga ccgtgaagga ggagcgcaac ttccaaaaat   11340
cttttaacaa ccatgtgcgc accctgatcg cccgcgagga agtgaccctg ggtctgatgc   11400
atctgtggga cctgatggag gctatcgccc aaaacccac tagcaaacca ctgacagctc   11460 agctgttttct ggtggttcaa catagcaggg acaacgaggc attcaggag gcgttgttga   11520 acatcaccga gcctgatggg agatggctgt atgatctgat caacatcctg caaagtatta   11580
tagtgcagga acgtagcctg ggtttggctg agaaagtggc agctatcaac tactcggtct   11640
tgagcctggg caaatactac gctcgcaaga tctacaagac cccctacgta cccatagaca   11700
aggaggtgaa gatagatggg ttttacatgc gcatgactct gaaggtgctg actctgagcg   11760
acgatctggg ggtgtatcgc aatgacagga tgcaccgcgc ggtgagcgcc agcaggaggc   11820
gcgagctgag cgacagagaa cttatgcaca gcttgcaaag agctctaacg ggggccggga   11880
ctgatgggga gaactacttt gacatgggag cggatttgca atggcaaccc agtcgcaggg   11940
ccatggaggc tgcagggtgt gagcttcctt acatagaaga ggtggatgaa gtcgaggacg   12000
aggagggcga gtacttggaa gactgatggc gcgacccgta ttttttgctag atggaacagc   12060 agcaggcacc ggaccccgca atgcgggcgg cgctgcagag ccagccgtcc ggcattaact   12120
cctcggacga ttggacccag gccatgcaac gcataatggc gctgacgacc cgcaaccccg   12180
aagcctttag acagcaaccc caggccaacc gcctttctgc catactggag gccgtagtgc   12240
cctcccgctc caaccccacc cacgagaagg tcctggctat cgtgaacgcg ctggtggaga   12300
acaaggccat ccgtcccgat gaggccgggc tggtatacaa tgctctcttg gagcgcgtgg   12360
cccgttacaa cagcagcaac gtgcaaacca acctggaccg gatggtgacc gatgtgcgcg   12420
aggccgtgtc tcagcgcgag cgattccagc gcgacgccaa cttggggtcg ttggtagcgc   12480
taaacgcttt cctcagcacc cagcccgcca acgtgccccg tggtcagcaa gactatacaa   12540 acttttttgag tgcattgaga ctcatggtag ctgaggtgcc ccagagcgag gtgtaccagt   12600
```

```
ccgggccaga ttacttcttc cagaccagca gacagggctt gcagacagtg aacctgactc   12660
aggctttcaa gaacctgaag ggtctgtggg gagtgcacgc cccagtaggg gatcgcgcga   12720
ccgtgtctag cttgctgact cccaactccc gcctgctgct gctgctggta tcccccttta   12780
ctgacagcgg tagcattgac cgcaactcgt acttgggcta cctgcttaac ctgtatcgcg   12840
aggccatagg acagagccag gtggacgagc agacctatca agaaatcacc caagtgagcc   12900
gcgccctggg tcaggaagac acgggcagtt tggaagccac cctgaacttc ttgctaacca   12960
accggtcaca gaagatccct cctcagtatg cgcttaccgc tgaggaggag cggatcctca   13020
gatacgtgca acagagcgtt ggactgttcc tgatgcagga gggggcgaca cctaccgccg   13080
cgctggacat gacagctcga aacatggagc ccagcatgta tgctagtaac aggccttttca   13140 ttaacaaact gctggactac ctgcacaggg cggccgccat gaactctgat tatttcacca   13200
atgctatcct gaaccacac tggctgcccc cacctggttt ctacactggc gagtacgaca   13260
tgcccgaccc caatgacggg ttcctgtggg acgatgtgga cagcagcata ttttccccgc   13320
ctcccggtta tacagtttgg aagaaggaag ggggcgatag aagacactct tccgtgtcgc   13380
tatccggaac ggctggtgct gccgcgaccg tgcccgaagc tgcaagtcct ttccctagct   13440 tgccctttttc actaaacagc gttcgcagca gtgaactggg gagaataacc cgcccgcgct   13500
tgatgggcga ggatgagtac ttgaatgact ctttgctgag gccagagagg gaaaagaact   13560
tccccaacaa tggaatagag agtctggtgg ataagatgag tagatggaag acctatgcgc   13620
aggatcacag agacgagccc aggatcttgg gggctacaag cagaccgatc cgtagacgcc   13680
agcgccacga caggcagatg ggtcttgtgt gggacgatga ggactctgcc gatgatagca   13740
gcgtgttgga cttgggtgga agaggagggg gcaacccgtt cgctcatctg cgtcccagat   13800
tcgggcgcat gttgtaaaag tgaaagtaaa ataaaaggc aactcaccaa ggccatggcg   13860
accgagcgtg cgttcgttct ttttttgttat ctgtgtctag tacgatgagg agacgagccg   13920
tgctaggcgg agcggtggtg tatccggagg gtcctcctcc ttcttacgag agcgtgatgc   13980
agcaacaggc ggcgatgata cagcccccac tggaggctcc cttcgtaccc ccacggtacc   14040
tggcgcctac ggaagggaga aacagcattc gttactcgga gctgtcgccc ctgtacgata   14100
ccaccaagtt gtatctggtg gacaacaagt cggcggacat cgcctccctg aactatcaga   14160
acgaccacag caacttcctg accacggtgg tgcagaacaa tgactttacc cccacggagg   14220
ctagcaccca gaccatcaac tttgacgagc ggtcgcgatg gggcggtcag ctgaagacca   14280
tcatgcacac caacatgccc aacgtgaacg agtacatgtt cagcaacaag ttcaaggcga   14340
gggtgatggt gtccagaaaa gctcctgaag gtgttacagt aaatgacacc tatgatcata   14400
aagaggatat cttgaagtat gagtggtttg agttcatttt accagaaggc aactttttcag   14460 ccaccatgac gatcgacctg atgaacaatg ccatcattga caactacctg gaaattggca   14520
gacagaatgg agtgctggaa agtgacattg gtgttaagtt tgacactaga aatttcaggc   14580
tcgggtggga ccccgaaact aagttgatta tgccaggtgt ctacacttat gaggcattcc   14640
atcctgacat tgtattgctg cctggttgcg gggtagactt tactgaaagc cgacttagca   14700
acttgcttgg catcaggaag agacatccat tccaggaggg tttcaaaatc atgtatgaag   14760
atcttgaagg gggtaatatt cctgcccttt tggatgtcac tgcctatgag gaaagcaaaa   14820
aggataccac tactgaaaca accacactgg ctgttgcaga ggaaactagt gaagatgatg   14880
atataactag aggagatacc tatataactg aaaaacaaaa acgtgaagct gcagctgctg   14940
aagttaaaaa agagttaaag atccaacctc tagaaaaaga cagcaagagt agaagctaca   15000
```

```
atgtcttgga agacaaaatc aacacagcct accgcagttg gtacctgtcc tacaattacg   15060
gtaaccctga gaaggaata aggtcttgga cactgctcac cacttcagat gtcacctgtg   15120
gggcagagca ggtctactgg tcgctccctg acatgatgca agacccagtc accttccgct   15180
ccacaagaca agtcaacaac tacccagtgg tgggtgcaga gcttatgccc gtcttctcaa   15240
agagtttcta caatgagcaa gccgtgtact ctcagcagct ccgacaggcc acttcgctca   15300
cgcacgtctt caaccgcttc cctgagaacc agatcctcat ccgcccgccg gcgcccacaa   15360
ttaccaccgt cagtgaaaac gttcctgctc tcacagatca cgggaccctg ccgttacgca   15420
gcagtatccg gggagtccag cgcgtgaccg ttactgacgc cagacgccgc acctgtccct   15480
acgtttacaa ggccctgggc atagtcgcgc gcgcgttct ttcaagccgc actttctaaa   15540
aaaaaaaaaa aaatgtccat tctcatctcg cccagtaata ataccggttg gggactgtat   15600
gcgcccacca agatgtatgg aggcgcccg aagcgctcta cccagcatcc tgtgcgcgtt   15660
cgcggtcatt tccgcgctcc ctggggcgca ctcaagggtc gtaccgcac tcggaccacg   15720
gtcgatgatg tgatcgacca ggtggtcgcc gatgctcgta attatactcc tactgcgcct   15780
acatctactg tggatgcagt tattgacagt gtggtggcag acgcccgcgc ctatgctcgc   15840
cggaagagcc gaaggaggcg catcgccagg cgccacaggg ctactcccgc catgcgagcc   15900
gcaaaagcta ttctgcggag ggccaaacgt gtggggcgaa gagccatgct tagagcggcc   15960
agacgcgcgg cttcaggtgc cagcagcggc aggtcccgca ggcgcgcggc cacggcggca   16020
gcagcggcca ttgccaacat ggcccaaccg cgaagaggca atgtgtactg ggtgcgtgat   16080
gccactaccg gccagcgcgt gcccgtgcgc acccgccccc ctcgcactta agagatactg   16140
agcagtctcc gatgttgtgt cccagcggca agtatgtcca agcgcaaata caaggaagag   16200
atgctccagg tcatcgcgcc tgaaatctac ggtccgccgg tgaaggatga aaaaaagccc   16260
cgcaaaatca agcgggtcaa aaataacaaa aaggaagaag atgacgatga tgggctggtg   16320
gagtttgtgc gcgagttcgc cccaagacgg cgcgtgcagt ggcgcgggcg caaagtgcgt   16380
caagtgctca gacccgggac cactgtggtt tttacacctg cgagcgttc cagcactact   16440
tttaaacggt cctatgatga ggtgtacggg gatgacgata ttcttgagca ggcggcagac   16500
cgccttgacg agtttgctta tggcaagcgc actagatcca gtcccaaaga ggaggctgtg   16560
tccattcctt tggatcatgg aaatcccacc cccagcctca aaccagtcac cctgcagcaa   16620
gtgctgcccg tgcctgcgcg gagaggcgta aagcgcgagg gtgaggacct atatcccacc   16680
atgcagctaa tggtgcccaa gcgccagagg ctagaagacg tactggagaa aatgaaagtg   16740
gatgccgata tccagcctga ggtcaaagta agacctatca aggaagtggc gccaggtttg   16800
ggagtacaaa ccttcgacat caagattccc accgagtcca tggaagtgca gaccgaacct   16860
gcaaaaccca ccacctcaat tgaggtgcaa acggaaccct ggatgccgc gcccgttgcc   16920
gcccccagca ccactcgaag atcacgacga agtacggcc cagcaagtct gctaatgccc   16980
aactatgctc tgcacccatc catcattccc actccgggtt acagaggcac tcgctactat   17040
cgaaaccgga gcaacacctc tcgccgccgc aaaccacctg caagtcgcac tcgccgtcgc   17100
cgccgccgca acactgccag caaattgact cccgccgccc tggtgcggag agtgtaccgc   17160
gatggtcgcg ctgaacctct gacgctgccg cgcgcgcgct accatccaag catcaccact   17220
taatgactgt tgacgctgcc tccttgcaga tatggccctc acttgccgcc ttcgcgtccc   17280
cattactggc taccgaggaa gaaactgcgc ccgtagaagg atgttgggc gagggatgcg   17340
ccgccacaga cgaaggcgcg ctatcagcag acgattaggg ggtggctttt tgccagctct   17400
```

```
tatacccatc atcgccgcag cgatcggggc gataccaggc atagcttcag tggcggttca   17460
ggcctcgcag cgccactaac attggaaaaa acttataaat aaaaaataga atggactctg   17520
acgctcctgg tcctgtgact atgttttttgt agagatggaa gacatcaatt tttcatccct   17580
ggctccgcga cacggcacga ggccgtacat gggcacctgg agcgacatcg gcacgagcca   17640
actgaacggg ggcgccttca attggagcag tatctggagc gggcttaaaa attttggctc   17700
gaccgtaaaa acctatggga acaaagcttg gaacagcagc acagggcagg ctctgagaaa   17760
taagcttaag gaacaaaact tccaacagaa ggtggtcgat gggatcgcct ctggtattaa   17820
cggcgtagtg gatctggcca accaggctgt acaaaaacag ataaacagcc gcctggaccc   17880
gccgcccgca acccctggtg aaatggaagt ggaggaagaa cttcctccgc tggaaaagcg   17940
gggcgacaag cgtccgcgac ccgagctaga gcagacgctg gtgacgcgcg cagacgagcc   18000
cccttcatat gaggaggcag taaagctcgg aatgcccact accaggcctg tagctcacat   18060
ggctaccggg gtgatgaaac cttctcagtc acatcgaccc gccaccttgg acttgcctcc   18120 tcccctgct tctgcggcgc ctgttcccaa acctgtcgct accagaaagc ccaccgccgt   18180
acagcccgtc gccgtagcca gaccgcgtcc tgggggcaca ccgcgcccga aagcaaactg   18240
gcaaagtact ctgaacagca tcgtgggtct gggcgtgcag agtgtaaagc gccgtcgctg   18300
ctattaatta aatatggagt agcgcttaac ttgcttgtct gtgtgtatgt atcatcacca   18360
cgccgccgca gcagaggaga aaggaagagg tcgcgcgccg aggctgagtt gctttcaaga   18420
tggccacccc atcgatgatg ccccaatggg catacatgca catcgccgga caggatgctt   18480
cggagtacct cagtccgggt ctggtgcagt tcgcccgtgc aacagacacc tacttcagta   18540
tggggaacaa atttagaaac cccacagtgg cgcccaccca cgatgtgacc accgaccgta   18600
gccagcgcct gatgctgcgc ttcgtgcccg ttgaccggga agacaatacc tactcttaca   18660
aagttcgcta cacgctggct gtaggcgaca acagagtgct tgacatggcc agcacattct   18720
ttgacattcg gggggtgctt gatagaggtc ctagcttcaa gccatattcc ggcacagctt   18780
acaattcact cgctcctaag ggcgcgccca atacatctca gtggatagtt acaacaaatg   18840
gggacaatgc agtaactacc accacaaaca catttggcat tgcttccatg aagggagaca   18900
atattactaa agaaggtttg caaattggga aagacattac cactactgaa ggagaagaaa   18960 agcccatttta tgccgataaa acatatcagc cagagcctca agttggagaa gaatcatgga   19020
ctgatactga tggaacaaat gaaaagtttg gtggaagagc ccttaaacca gctaccaaca   19080
tgaagccatg ctacgggtct tttgcaagac ctacaaacat aaaaggggc caagctaaaa   19140 acagaaaagt aaaaccaaca accgaaggag gggttgaaac tgaggaacca gatattgata   19200 tggaatttttt cgatggtaga gatgctgttg caggagcttt agcgcctgaa attgtgcttt   19260
atacggaaaa tgtaaatttg gaaactccag acagtcatgt ggtatataaa ccagaaacgt   19320
ctaataactc tcatgcaaat ttgggtcaac aagccatgcc taacagaccc aattacattg   19380 gcttcagggga taacttcgta ggcctaatgt actacaacag tactggaaat atgggagttt   19440
tggctggcca agcatcacaa ctgaatgcag tggttgactt gcaggacaga aatactgaac   19500
tgtcatatca gcttttgctt gattctctgg gagacagaac cagatacttc agcatgtgga   19560
atcaggctgt ggacagttac gatcccgatg ttcgcattat tgaaaatcat ggcatcgagg   19620
atgaactgcc taattactgt tttcctctga atggcatagg accagggcac acatatcaag   19680
gcattaaagt taaaaccgat gacactaatg gatgggaaaa agatgctaat gttgctccag   19740
ctaatgaaat aaccataggc aacaacctgg ctatggaaat taatatccaa gctaaccttt   19800
```

```
ggagaagttt tctgtactct aatgtggctt tgtaccttcc agatgtttac aagtacacgc  19860
cacctaacat tactttgccc actaacacca acacctatga gtacatgaac gggcgagtgg  19920
tatccccatc cctggttgat tcatacatca acattggcgc caggtggtct cttgacccaa  19980
tggacaatgt gaatccattc aaccaccacc gcaatgctgg tctgcgctac aggtccatgc  20040
ttctgggaaa tggtcgttat gtgcctttcc acatacaagt gcctcagaaa ttctttgctg  20100
tcaagaacct acttcttcta cctggctcct acacctacga gtggaacttc cgaaaggatg  20160
tgaacatggt cctgcaaagt tcccttggaa atgacctcag aacgatggt gctaccataa   20220
gtttcaccag catcaatctc tatgccacct tcttccccat ggctcacaac acagcttcca  20280
cccttgaagc catgctgcgc aacgatacca atgatcagtc atttaacgac tacctctctg  20340
cagctaacat gctttacccc attcctgcca atgcaaccaa cattccaatt tccatcccat  20400
ctcgcaactg ggcagccttc aggggctggt ccttcaccag actcaaaacc aaggagactc  20460
catctcttgg atcagggttc gatccctact tcgtatattc tggatctatt ccctacctgg  20520
atggcacctt ttaccttaac cacactttca gaaggtctc catcatgttt gactcctcag   20580
tcagctggcc tggcaatgac aggctgttga gtccaaatga gtttgaaatc aagcgcactg  20640
tggacgggga aggatacaac gtggcacaat gcaacatgac caaagactgg ttcctggttc  20700
agatgcttgc caattacaac attggctacc agggctttta catccctgag ggatacaagg  20760
atcgcatgta ctcctttttc agaaacttcc agcctatgag caggcaggtg gttgatgagg  20820
ttaattacac tgactacaaa gccgtcacct taccatacca acacaacaac tctggctttg  20880
tagggtacct tgcacctact atgagacaag gggaaccta cccagccaat tatccatacc   20940
cgctcatcgg aactactgcc gttaagagtg tcacccagaa aaagttcctg tgcgacagga  21000
ccatgtggcg cattcccttc tccagcaact tcatgtccat gggggccctt accgacctgg  21060
gacagaacat gctctatgcc aactcagccc atgcgctgga catgactttt gaggtggatc  21120
ccatggatga gcccacctg ctttatcttc ttttcgaagt cttcgacgtg gtcagagtgc   21180
accagccaca ccgcggcgtc atcgaggccg tctacctgcg cacaccgttc tcggccggca  21240
acgccaccac ataagaagcc tcttgcttct tgcaagcagc agctgcagcc atgacatgcg  21300
ggtccggaaa cggctccagc gagcaagagc tcaaagccat cgtccgagac ctgggctgcg  21360
gaccctattt cctgggaacc tttgacaagc gtttcccggg gttcatggcc cccgacaagc  21420
tcgcctgcgc catagtcaac actgccggac gcgagacggg gggagagcac tggctggctt  21480
ttggttggaa cccgcgctac aacacctgct accttttga tccttttggg ttctcggatg   21540
agcggctcaa acagatttac cagtttgagt acgaggggct cctgcgtcgc agtgcccttg  21600
ctaccaaaga ccgctgcatc accctggaga agtctaccca aagcgtgcag ggtccgcgct  21660
cagccgcctg tggactttt tgctgtatgt tccttcatgc ctttgtgcac tggcccgacc   21720
gccccatgga cggaaacccc accatgaagt tgctgactgg ggtgtccaac agcatgctcc  21780
aatcacccca gtccagccc accctgcgcc gcaaccagga ggtgctatac cgcttcctaa   21840
acacccactc atcttacttt cgttctcacc gcgcgcgcat tgaaagggcc accgcgtttg  21900
accgtatgga tatgcaataa gtcatgtaaa accgtgttca ataaacagca ctttattttt  21960
acatgcactg aggctctggt tttgctcatt tgtttcatca tttactcaga agtcgaatgg  22020
gttctggcgg gagtcagagt gacccgcggg cagggatacg ttgcggaact gtaacctgtt  22080
ctgccacttg aactcgggga ttaccagctt gggaactgga atctcgggaa aggtgtcttg  22140
ccacaacttt ctggtcagtt gcatagcgcc aagcaggtca ggagcagaga tcttgaaatc  22200
```

```
acagttgggg ccggcattct ggacacggga gttgcgatac actgggttgc aacactggaa   22260
cactatcaac gctgggtgtc ttacgcttgc caacacggtt gggtcactga tggtagtcac   22320
atccaagtct tcagcattgg ccatcccaaa ggggtcatc ttacatgtct gcctgcccat    22380
cacgggagcg cagcctggct tgtggttgca atcacaatga atggggatca gcatcatcct   22440
ggcttggtcg ggagttatcc ctgggtacac agccttcatg aaggcttcgt actgcttaaa   22500
agcttcctgg gccttacttc cctcggtgta gaacatccca caggacttgc tggaaaattg   22560
attagtagta cagttggcat cattcacaca acagcgggca tcgttgttgg ccaactgaac   22620
cacatttctg ccccagcggt tttgggtgat cttggctctg tctggattct ccttcatagc   22680
gcgctgcccg ttctcgctcg ccacatccat ctcgataatg tggtccttct ggatcatgat   22740
agtgccatgc aggcatttca ccttgccttc ataatcggtg catccatgag cccacagagc   22800
gcacccggtg cactcccaat tattgtgggc gatctcagaa taataatgta ccaatccctg   22860
catgaatctt cccatcattg ttgtcaaggt cttcatgctg gtaaatgtca gcgggatgcc   22920
acggtgctcc tcgttcacat actggtggca gatacgcttg tattgctcgt gctgctctgg   22980
catcagcttg aaagaggttc tcagatcatt atccagcctg tacctttcca ttagcacagc   23040
catcacttcc atgcccttct cccaggcaga taccagggc agactcaaag gattcctaac    23100
agcaataaaa gtagctcctt tagctatagg gtcattcttg tcgatcttct caacacttct   23160
cttgccatcc ttctcaatga tgcgcaccgg ggggtagctg aagcccacgg ccaccaactg   23220
agcctgttct ctttcttctt cactatcctg gctgatgtct gcagaggga catgcttggt    23280 cttcctgggc ttcttcttgg gagggatcgg gggaggactg ttgctccgct ccggagacag   23340
ggatgactgc gaagtttcgc ttaccaatac cacctggctc tcggtagaag aaccggaccc   23400
cacacgacgg taggtgttcc tcttcggggg cagaggtgga ggcgactgag atgggctgcg   23460
gtctggcctt ggaggcggat ggctggcaga gctcattccg cgttcggggg tgtgctcccg   23520
gtggcggtcg cttgactgat ttcctccgcg gctggccatt gtgttctcct aggcagagaa   23580
acaacagaca tggaaactca gccatcactg ccaacatcgc tgcaagcacc atcacacctc   23640
gcccccagca gcgacgagga ggagagctta accacccac acccagtcc cgctaccacc     23700 acctctaccc tcgatgatga ggaggaggtc gacgcagccc aggagatgca ggcgcaggat   23760
aatgtgaaaa cggaagagat tgaggcagat gtcgagcagg acccgggcta tgtgacgccg   23820
gcggagcacc aggaggagct gaaacgcttt ctagacagag aggatgacga ccgcccagag   23880
catcaagcag atggcgttta ccaggaggct gggatcaggg atcatgtcgc cgactacctc   23940
accggccttg gtggggagga cgtgctcctc aaacatctag caaggcagtc gatcatagtt   24000
aaagacgcat tgctcgatct cactgaagtg cccatcagtg tggaagagct tagccgcgcc   24060
tacgagctga acctcttttc gcctcaggta cccccaagc ggcagccaaa cggcacctgc     24120
gaggccaacc ctcgactcaa cttctatcca gcttttacta tccccgaagt gttggccacc   24180
taccacatct ttttcaagaa ccaaaagatt ccagtctcct gccgcgccaa ccgcacccgc   24240
gccgatgccc tgctcaactt gggtccggga gctcgcttac ctgatatagc ttccttggaa   24300
gaggttccaa agatctttga gggtctggga agtgatgaga cacgggccgc aaatgctctg   24360
caacagggag agaatgacat ggatgaacac cacagcgctc tggtggaact ggagggtgac   24420
aatgcccgga ttgcagtgct caagcgcagt atcgtggtca cccattttgc ctaccccgct   24480
gttaacctgc cccccaaagt tatgagcgct gtcatggacc atctgctcat caacgcagca   24540
agacctcttt cagaaaacca gaacatgcag gatccagacg cctcggacga gggcaagccg   24600
```

```
gtagtcagtg acgagcagct atctcgctgg ctgggtacca actccccccg agatttggaa   24660
gagaggcgca agcttatgat ggctgtagtg ctagtaactg tggagctgga gtgtctgcgc   24720 cgcttttttca ccgaccctga gaccctgcgc aagctagagg agaacctgca ctacaccttt   24780
agacatggct tcgtgcggca ggcatgcaag atctccaacg tggagcttac caacctggtt   24840
tcttacatgg gcattttgca tgagaaccga ctagggcaga gcgtcctgca caccacccttt   24900 aaagggagg cccgccgtga ctacatccga gactgtgtct acctctacct ctgccatacc   24960
tggcaaactg gtatgggtgt gtggcaacag tgttttggaag agcagaacct aaaagagctg   25020
gacaagctct tgcagagatc cctcaaagcc ctgtggacag gttttgatga gcgcaccgtc   25080
gcctcggacc tggcagacat catcttcccc gagcgtctca gggttactct gcgaaacggc   25140
ctgccagact ttatgagcca gagcatgctt aacaactttc gctctttcat cctggaacgc   25200
tccggtatcc tgcctgccac ctgctgtgcg ctgccctccg actttgtgcc tctcacctac   25260
cgcgagtgcc caccgccgct atggagccac tgctacctgt tccgcctggc caactacctc   25320
tcctaccact cggatgttat agaggatgtg agcggagacg gcctgctgga atgccactgc   25380
cgctgcaatc tttgcacacc ccaccgctcc cttgcctgca ccccagtt gctgagcgag   25440 acccagatta tcggcacctt cgagctgcag ggtcccagaa gtaaaggcga ggggtcttct   25500
ccggggcaga gtttgaaact gacaccgggg ctgtggacct ccgcctacct gcgcaagttt   25560
caccccgagg actaccatcc ctatgagatc aggttctatg aggaccaatc acatcctccc   25620
aaagtcgagc tctcagcctg cgtcatcacc caggagcaa ttctggccca attgcaagcc   25680
atccaaaaat ctcgccaaga atttctgcta aaaaagggaa acggggtcta ccttgaccct   25740
cagaccggtg aggagctcaa cacaaggttc ccccaggatg tcccatcgcc gaggaagcaa   25800
gaagttgaag gtgcagctgt cgcccccaga ggatatgaag gaagactggg acagtcaggc   25860
agaggaggag atggaagatt gggacagcca ggcagaggag gtggacagcc tggaggaaga   25920
cagtttggag gaggaagacg aggaggcaga ggaggtggaa gaagcaaccg ccgccaaaca   25980
gttgtcatcg gcgcggaga caagcaagtc cccagacagc agcacggcta ccatctccgc   26040
tccgggtcgg ggggcccagc ggcggcccaa cagtagatgg gacgagaccg ggcgattccc   26100
aaacccgacc accgcttcca agaccggtaa gaaggagcga cagggataca agtcctggcg   26160
tggacataaa aacgctatca tctcctgctt gcatgaatgc gggggcaaca tatccttcac   26220
ccggcgatac ctgctcttcc accacggtgt aaacttcccc cgcaatatct tgcattacta   26280
ccgtcacctc cacagcccct actgcagtca gcaagtcccg gcaaccccga cagaaaaata   26340
cagcagcgac aacggtgacc agaaaaccag cagttagaaa atccacaaca agtgcaccag   26400
gaggaggact gaggatcaca gcgaacgagc cagcgcagac cagagagctg aggaaccgga   26460
tctttccaac cctctctatgcc attttccagc agagtcgggg gcaagagcag gaactgaaag   26520
taaaaaaccg atctctgcgc tcgctcacca gaagttgttt gtatcacaag agcgaagacc   26580
aacttcagcg cactctcgag gacgccgagg ctctcttcaa caagtactgc gcgctgactc   26640
ttaaagagta gcccttgccc gcgctcattt tgaaaacggc gggaatcacg tcacccttgg   26700
cacctgtcct ttgcccttgt catgagtaaa gagattccca cgccttacat gtggagctat   26760
cagccccaaa tggggttggc agcaggcgct tcccaggact actccacccg catgaattgg   26820
cttagcgccg ggccctcaat gatatcacgg gttaatgata tacgagctta tcgaaaccag   26880
ttactcctag aacagtcagc tctcaccacc acaccccgtc aacaccttaa tccccgaaat   26940
tggcccgcca ccctggtgta ccaggaaaat cccgctccca ccaccgtact acttcctcga   27000
```

```
gacgcccagg ccgaagttca gatgactaac gcaggtgtac agctggcggg cggttccgcc   27060
ctatgtcgtc accgacctca acagagtata aaacgcctgg tgattagagg ccgaggtatc   27120
cagctcaacg acgagtcggt tagctcttcg cttggtctgc gaccagacgg agtcttccaa   27180
atcgccggct gtgggagatc ttccttcact cctcgtcagg ctgtgctgac tttggagagt   27240
tcgtcctcgc agccccgctc gggcggcatt ggaactctcc agtttgtgga ggagtttact   27300
ccctctgtct acttcaaccc cttctccggc tctcctggcc agtacccgga cgagttcata   27360
ccaaacttcg acgcaatcag cgagtcagtg gatggctatg attgatgtct aatggtggtg   27420
cggctgagct agctcgactg cgacacctag accactgccg ccgctttcgc tgcttcgccc   27480
gggaactcac cgagttcatc tacttcgaac tctccgagga gcaccctcag ggtccggccc   27540
acggagtgcg gattaccatc gaaggggggaa tagactctcg cctgcatcgc atcttctccc   27600
agcggcccgt gctaattgaa cgcgaccagg gaaatacaac catctccatc tactgcatct   27660
gtaaccaccc cggattgcat gaaagccttt gctgtcttgt ttgtgctgag tttaataaaa   27720
actgagttaa gaccctccta cggactaccg cttcttcaat caggacttta caacaccaac   27780
cagatcttcc agaagaccca gacccttcct cctttcatcc aggactctaa ctctaccttc   27840
ccagcaccct ccactactaa ccttcccgaa acaaacaagc ttgcatctca tctgcaacac   27900
cgcctttcac gaagccttct ttctgccaat actaccactc ccaaaaccgg aggtgagctc   27960
cgcggtcttc ctactgacga cccctgggtg gtagcgggtt ttgtaacgtt aggagtagtt   28020
gcgggtgggc ttgtgctgat cctttgctac ctatacacac cttgctgtgc atatttagtc   28080
atattgtgct gttggtttaa gaaatggggg ccatactagt cgtgcttgct ttactttcgc   28140
ttttgggtct gggctctgct aatctcaatc ctctcgatca cgatccatgt ttagacttcg   28200
acccagaaaa ctgcacactt acttttgcac ccgacacaag ccgtctctgt ggagttctta   28260
ttaagtgcgg atgggactgc aggtccgttg aaattacaca taataacaaa acatggaaca   28320
ataccttatc caccacatgg gagccaggag ttccccagtg gtatactgtc tctgtccgag   28380
gtcctgacgg ttccatccgc attagtaaca acactttcat tttttctgaa atgtgcgatc   28440
tggccatgtt catgagcaga cagtatgacc tatggcctcc cagcaaagag aacattgtgg   28500
cattttccat tgcttattgc ttggtaacat gcatcatcac tgctatcatt tgtgtgtgca   28560
tacacttgct tatagttatt cgccctagac aaagcaatga ggaaaaagag aaaatgcctt   28620 aaccttttc ctcataccctt ttctttacag catggcttct gttacagctc taattattgc   28680
cagcattgtc actgtcgctc acgggcaaac aattgtccat attaccttag gacataatca   28740
cactcttgta gggcccccaa ttacttcaga ggttatttgg accaaacttg gaagtgttga   28800
ttattttgat ataatttgca acaaaactaa accaatattt gtaatctgta acagacaaaa   28860
tctcacgtta attaatgtta gcaaaattta taacggttac tattatggtt atgacagatc   28920
cagtagtcaa tataaaaatt acttagttcg cataactcag cccaaattaa cagtgccaac   28980
tatgacaata attaaaatgg ctaataaagc attagaaaat tttacatcac caacaacacc   29040
caatgaaaaa aacattccaa attcaatgat tgcaattatt gcggcggtgg cattgggaat   29100
ggcactaata ataatatgca tgctcctata tgcttgttac tataaaaagt ttcaacataa   29160
acaggatcca ctactaaatt ttaacattta attttttata cagatgattt ccactacaat   29220
ttttatcatt actagccttg cagctgtaac ttatggccgt tcacacctaa ctgtacctgt   29280
tggctcaaca tgtacactac aaggaccccca agaaggctat gtcacttggt ggagaatata   29340
tgataatgga gggttcgcta gaccatgtga tcagcctggt acaaaatttt catgcaacgg   29400
```

```
aagagacttg accattatta acataacatc aaatgagcaa ggcttctatt atggaaccaa   29460
ctataaaaat agtttagatt acaacattat tgtagtgcca gccaccactt ctgctccccg   29520
caaatccact ttctctagca gcagtgccaa agcaagcaca attcctaaaa cagcttctgc   29580
tatgttaaag cttccaaaaa tcgctttaag taattccaca gccgctccca atacaattcc   29640
taaatcaaca attggcatca ttactgccgt ggtagtggga ttaatgatta tattttgtg    29700 tataatgtac tacgcctgct gctatagaaa acatgaacaa aaaggtgatg cattactaaa   29760
ttttgatatt taattttta tagaattatg atattgtttc aatcaaatac cactacctcc    29820
tatgcataca caaacattca gcctaaatac gctatgcaac tagaaatcac aatactaatt   29880
gtaattggaa ttcttatact atctgttatt ctttatttta tattctgccg tcaaataccc   29940
aatgttcata gaaattctaa aagacgtccc atctattctc ctatgattag tcgtcccat    30000 atggctctga atgaaatcta agatcttttt ttttttctct tacagtatgg tgaacatcaa   30060
tcatgatccc tagaaatttc ttcttcacca tactcatctg tgcttttaat gtctgtgcta   30120
ctttcacagc agtagccact gcaagcccag actgtatagg accatttgct tcctatgcac   30180
tttttgcctt cgttacttgc atctgcgtgt gtagcatagt ctgcctggtt attaattttt    30240
tccaactggt agactggatc tttgtgcgaa ttgcctacct acgtcaccat cccgaatacc   30300
gcaatcaaaa tgttgcggca cttcttaggc ttatttaaaa ccatgcaggc tatgctacca   30360
gtcattttaa ttttgctact accctgcatt cccctagctt ccaccgccac tcgcgctaca   30420
cctgaacaac ttagaaaatg caaatttcaa caaccatggt catttcttga ttgctaccat   30480
gaaaaatctg attttcccac atactggata gtgattgttg aataattaa catactttca     30540 tgtacctttt tctcaatcac aatataccc acatttaatt ttgggtggaa ttctcccaat    30600
gcactgggtt acccacaaga accagatgaa catattccac tacaacacat acaacaacca   30660
ctagcactgg tacagtatga aaatgagcca caaccttcac tgcccctgc cattagttac    30720 ttcaacctaa ccggcggaga tgactgaccc aatcgccaca tcatccaccg ctgccaagga   30780
gctgctggac atggacggac gtgcctcaga acagcgactc atccaactac gcattcgtca   30840
gcagcaggaa cgagcagtaa aagagctaag ggatgccatt gggattcacc agtgcaaaaa   30900
aggcatattc tgcttagtaa aacaatccaa aatctcctac gagatcaccg ctactgacca   30960
tcgtctctca tacgagctcg gtccgcagcg acaaaaattc acctgcatgg tgggaatcaa   31020
ccccatagtt atcacccagc agtctggaga tactaagggt tgtatccagt gttcctgtga   31080
ttccaccgag tgcatctaca cactgctgaa gaccctctgc ggccttcgag acctcctacc   31140
catgaactaa tcattgcccc taccttaccc aatcaaaata ttaataaaga cacttacttg   31200
aaatcagcaa tacagtcttt gtcaaaactt tctaccagca gcacctcacc ctcttcccaa   31260
ctctggtact ctaaacgtcg gagggtggca tactttctcc acactttgaa agggatgtca   31320
aattttattt cctcttcttt gcccacaatc ttcatttctt tatccccaga tggccaagcg   31380
agctcggcta agcacttcct tcaacccggt gtacccttat gaagatgaaa gcagctcaca   31440
acacccattt ataaatcctg gtttcatttc ccctgacggg ttcacacaaa gtccaaacgg   31500
ggttttaagt cttaaatgtg ttaatccact taccactgca agcggctccc tccaacttaa   31560
agtgggaagt ggtcttacag tagacactac tgatggatcc ttagaagaaa acatcaaagt   31620
taacaccccc ctaacaaagt caaaccattc tataaattta ccaataggaa acggtttgca   31680
aatagaacaa aacaaacttt gcagtaaaact cggaaatggt cttacatttg actcttccaa   31740
ttctattgca ctgaaaaata acactttatg gacaggtcca aaaccagaag ccaactgcat   31800
```

```
aattgaatac gggaaacaaa acccagatag caaactaact ttaatccttg taaaaaatgg    31860
aggaattgtt aatggatatg taacgctaat gggagcctca gactacgtta acaccttatt    31920
taaaaacaaa aatgtctcca ttaatgtaga actatacttt gatgccactg gtcatatatt    31980
accagactca tcttctctta aaacagatct agaactaaaa tacaagcaaa ccgctgactt    32040
tagtgcaaga ggttttatgc caagtactac agcgtatcca tttgtccttc ctaatgcggg    32100
aacacataat gaaaattata ttttggtca atgctactac aaagcaagcg atggtgccct    32160
ttttccgttg gaagttactg ttatgcttaa taaacgcctg ccagatagtc gcacatccta    32220
tgttatgact tttttatggt ccttgaatgc tggtctagct ccagaaacta ctcaggcaac    32280
cctcataacc tccccattta cctttcccta tattagagaa gatgactgac aacaaaaata    32340
aagttcaaca ttttttattg aaattccttt tacagtattc gagtagttat tttgcctccc    32400
ccttcccatt taacagaata caccaatctc tccccacgca cagctttaaa catttggata    32460
ccattagaga tagacatagt tttagattcc acattccaaa cagtttcaga gcgagccaat    32520
ctggggtcag taatacataa aaatgcatcg ggatagtctt ttaaagcgct ttcacagtcc    32580
aactgttgcg gatgcgactc cggagtctga atcacggtca tctggaagaa gaacgatggg    32640
aatcataatc cgaaaacgga atcgggcgat tgtgtctcat caaacccaca agcaaccgct    32700
gtctgcgtcg ctccgtgcga ctgctgttta tgggatcggg gtccgcagtg tcctgaagca    32760
tgattttaat agcccttaac attaactttc tggtgcgatg cgcgcagcaa cgcattctga    32820
tttcacttag attactacag taggtacagc acattatcac aatattgttt aataaaccat    32880
aattaaaagc gctccagcca aaactcatat ctgatataat cgcccctgca tgaccatcat    32940
accaaagttt aatataaatt aaatgtcgtt ccctcaaaaa cacactaccc acatacgaa     33000 tctcttttgg catgtgcata ttaacaattt gtctgtacca tggacaacgt tggttaatca    33060
tgcaacccaa tataaccttc cggaaccaca ctgccaacac cgctccccca gccatgcatt    33120
gaagtgaacc ctgctgatta caatgacaat gaagaaccca attctctcga ccatgaatca    33180
cttgagactc aaaaatatct atagtagcac aacaaagaca taaatgcatg catcttctca    33240 taattttttaa ctcctctgga tttaaaaaca tatcccaagg aatgggaaac tcttgcagaa    33300
cagtaaagct ggcagaacaa ggaagaccac gaacacaact tacactatgc atagtcatag    33360
tatcacaatc tggcaacagc gggtggtctt cagtcataga agctcgggtt tcattttcct    33420
cacatcgtgg taattgggct ctggtgtaag ggtgatgtct ggcgcatgat gtggagcgtg    33480
cgcgcaacct tgtcataatg gagttgcttc ctgacattct cgtattttgt atagcaaaac    33540
gctgccctgg cacaacacac tcttcttcgt cttctatcct gccgcttagt gtgttccgtc    33600
tgataattca agtacagcca cactcttaag ttggtcaaaa gaatgctggc ttcagttgta    33660
atcaaaactc catcatattt aattgttcta aggaaatcat ccacggtagc atatgcaaat    33720
cccaaccaag caatgcaact ggattgcgtt tcaagcagca gaggagaggg aagagacgga    33780
agaatcatgt taattttttat tccaaacgat ctcgcagtac ttcaaattgt agatcgcgca    33840
gatggcatct atcgccccca ctgtgttggt gaaaagcac agctaaatca aaagaaatgc    33900
gattttcaag gtgctcaacg gtggcttcca acaaagcctc cacgcgcaca tccaaaaaca    33960 aagaatacc aaaagaagga gcattttcta actcctcaaa catcatatta cattcctgca    34020
ccattcccag ataattttca gctttccagc cttgaattat tcgtgtcagt tcttgtggta    34080
aatccaaacc acacattaca aacaggtccc ggagggcgcc ctccaccacc attcttaaac    34140
acaccctcat aatgacaaaa tatcttgctc ctgtgtcacc tgtagcaaat taagaatggc    34200
```

```
atcatcaatt gacatgccct tggctctaag ttcttctcta agttctagtt gtagatactc    34260
tctcatatta tcaccaaact gcttagccag aagcccccg ggaacaatag caggggacgc    34320
tacagtgcag tacaagcgca gacctcccca attggctcca gcaaaaacaa gattagaata    34380
agcatactgg gaaccaccag taatatcatc aaagttgctg gaaatataat caggcagagt    34440
ttcttgtaaa aattgaataa agaaaaaatt ttccaaagaa acattcaaaa ccgttgggat    34500
gcaaatacaa taggttaccg cgctgcgctc caacattgtt agttttgaat tagtctgcaa    34560
aataaaagaa acaagcgtca tatcatagta gcctgtcgaa caggtggaaa aatcagtctt    34620
tccatcacaa gacaagccac agggtctcca gctcgaccct cgtaaaacct gtcattgtga    34680
ttaaacaaca gcaccgaaag ttcctcgcgg tggccagcat gaataattct tgatgaagca    34740
tacaatccag acatgttagc atcagttaaa gagaaaaaac agccaacata gcctctgggt    34800
ataattatgc ttaattttaa gtatagcaaa gccacccctc gcggatacaa agtaaaaggc    34860
acaggagaat aaaaaatata attatttctc tgctgctgtt caggcaacgt tgctcccggt    34920
ccctctaaat agacatacaa agcctcatca gccatggctt accaggcaaa gtacagcggg    34980
cgcacaaagc acaagctcta aagaagctct aaaaacactc tccaacctct ccacaatata    35040
tacacaagcc ctaaactgac gtaatgggag taaagtgaaa aaaaaatacc gccaagccca    35100
acacacaccc cgaaactgcg tcagcaggaa aaagtacagt ttcacttccg cattcccaac    35160
aagcgtaact tcctctttct catggtacgt cacatccgat taacttgcaa cgtcattttc    35220
ccacggtcgc gccgcccctt ttagccgtta accccgcagc caatcaccac acagcgcgca    35280 ctttttttaaa ttacctcatt tacatgttgg caccattcca tctataaggt atattatata    35340
gatag                                                               35345

<210> SEQ ID NO 5
<211> LENGTH: 17
<212> TYPE: DNA
<213> ORGANISM: artificial
<220> FEATURE:
<223> OTHER INFORMATION: forward primer

<400> SEQUENCE: 5
gtaaaacgac ggccagt                                                         17

<210> SEQ ID NO 6
<211> LENGTH: 17
<212> TYPE: DNA
<213> ORGANISM: artificial
<220> FEATURE:
<223> OTHER INFORMATION: reverse primer

<400> SEQUENCE: 6
caggaaacag ctatgac                                                         17
```